(12) United States Patent
Kondo et al.

(10) Patent No.: US 9,546,376 B2
(45) Date of Patent: Jan. 17, 2017

(54) GENE FOR INCREASING THE PRODUCTION OF PLANT BIOMASS AND/OR SEEDS AND METHOD FOR USE THEREOF

(75) Inventors: Satoshi Kondo, Miyoshi (JP); Chikara Ohto, Toyota (JP); Kenichi Ogawa, Kyoto (JP); Norihiro Mitsukawa, Miyoshi (JP); Nobuhiko Muramoto, Ichinomiya (JP); Tomoko Tanaka, Nagoya (JP); Hiroki Sugimoto, Aichi-gun (JP)

(73) Assignees: TOYOTA JIDOSHA KABUSHIKI KAISHA, Aichi-ken (JP); OKAYAMA PREFECTURE, Okayama-shi (JP)

( * ) Notice: Subject to any disclaimer, the term of this patent is extended or adjusted under 35 U.S.C. 154(b) by 697 days.

(21) Appl. No.: 13/256,190

(22) PCT Filed: Mar. 10, 2010

(86) PCT No.: PCT/JP2010/053939
§ 371 (c)(1),
(2), (4) Date: Sep. 12, 2011

(87) PCT Pub. No.: WO2010/104092
PCT Pub. Date: Sep. 16, 2010

(65) Prior Publication Data
US 2012/0005787 A1    Jan. 5, 2012

(30) Foreign Application Priority Data
Mar. 12, 2009    (JP) ................... 2009-060154

(51) Int. Cl.
C12N 15/82    (2006.01)

(52) U.S. Cl.
CPC ................... *C12N 15/8261* (2013.01)

(58) Field of Classification Search
None
See application file for complete search history.

(56) References Cited

U.S. PATENT DOCUMENTS

| | | | |
|---|---|---|---|
| 7,176,351 B2 | 2/2007 | Kisaka et al. | |
| 8,575,428 B2 | 11/2013 | Kondo et al. | |
| 2002/0040490 A1 | 4/2002 | Gorlach et al. | |
| 2003/0135870 A1* | 7/2003 | Cheikh et al. | 800/8 |
| 2005/0114925 A1 | 5/2005 | Kisaka et al. | |
| 2006/0123505 A1 | 6/2006 | Kikuchi et al. | |
| 2006/0183137 A1 | 8/2006 | Harper et al. | |
| 2006/0236419 A1 | 10/2006 | LaRosa et al. | |
| 2007/0136839 A1 | 6/2007 | Cook et al. | |
| 2009/0300797 A1* | 12/2009 | Ogawa | C12N 9/88 800/279 |
| 2010/0016166 A1 | 1/2010 | Ogawa et al. | |
| 2010/0083404 A1 | 4/2010 | Ogawa et al. | |
| 2011/0078818 A1 | 3/2011 | Kondo et al. | |
| 2012/0005787 A1 | 1/2012 | Kondo et al. | |
| 2012/0159666 A1 | 6/2012 | Yonekura et al. | |

FOREIGN PATENT DOCUMENTS

| | | |
|---|---|---|
| JP | 9-503389 A | 4/1997 |
| JP | 2000-515020 A | 11/2000 |
| JP | 2001-505410 A | 4/2001 |
| JP | 2001-519659 A | 10/2001 |
| JP | 2005-130770 A | 5/2005 |
| JP | 2005-185101 A | 7/2005 |
| JP | 2007-530063 A | 11/2007 |
| WO | 95/09911 A1 | 4/1995 |
| WO | 98/03631 A | 1/1998 |
| WO | 98/10082 A1 | 3/1998 |
| WO | 98/42851 A1 | 10/1998 |
| WO | 0210210 | 2/2002 |
| WO | WO02/10210 * | 2/2002 |
| WO | 2005/094562 A1 | 10/2005 |
| WO | WO 2006/076423 * | 7/2006 |
| WO | 2007/091634 A1 | 8/2007 |
| WO | WO 2008/034648 A1 | 3/2008 |
| WO | 2008/072602 A1 | 6/2008 |
| WO | 2008/087932 A1 | 7/2008 |
| WO | 2008082602 | 7/2008 |
| WO | WO2008/087932 * | 7/2008 |
| WO | 2009/113684 A1 | 9/2009 |

OTHER PUBLICATIONS

Saez et al., PLant J 37:354-69 (2004).*
Rizhsky_Plant Physiol_134_1683_2004.*
Saez_Plant J 37 354_2004.*
Rizhsky_Plant Phys 134 1683_2004.*
Guo Proc Natl Acad Sci 101 9205 2004.*
Zhang_Curr Opin Plant Biol_6_430_2003.*
Whisstock_Q Rev Biophys_36_307_2003.*
Schweighofer_Trends Plant Sci 9 236_2004.*
Kasuga et al., Plant Cell Physiol 45(3)346-50 (2004).*
Schweighofer et al., Trends Plant Sci 9(5):236-43 (2004).*
Rizhsky et al., Plant Physiol 134:1683-96 (2004).*
Soporya & Munshib, Crit Rev Plant Sci 17(3):245-318 (1998).*
Leung et al., Plant Cell 9:759-71 (1997).*
Guo et al., Proc Natl Acad Sci USA 101:9205-10 (2004).*
Zhang et al., Curr Opin Plant Biol 6:430-40 (2003).*
Sugimoto et al., 21st Int'l Conf Arab Res (2010).*
Fourgoux-Nicol et al., Plant Mol Biol 40:857-72 (1999).*
Ken'ichi Ogawa, "Function of glutathione in improvement in crop yield and quality", Research journal of food and agriculture, Mar. 1, 2009, pp. 44-47, vol. 32, No. 3.

(Continued)

*Primary Examiner* — Medina A Ibrahim
*Assistant Examiner* — Russell Boggs
(74) *Attorney, Agent, or Firm* — Sughrue Mion, PLLC

(57) ABSTRACT

A technique by which the production of plant biomass can be significantly increased is provided. A gene encoding protein phosphatase 2C having 3 consensus sequences comprising the amino acid sequences shown in SEQ ID NOS: 1-3 from the N-terminal side in such order and a gene encoding glutathione-binding plastid-type fructose 1,6-bisphosphate aldolase is introduced, or an expression control region of endogenous genes corresponding to the genes are modified.

6 Claims, 14 Drawing Sheets

(56) References Cited

OTHER PUBLICATIONS

U.S. Appl. No. 12/922,432, filed Dec. 3, 2010, Satoshi Kondo.
Saez et al., "Gain-of-function and loss-of-function phenotypes of the protein phosphatase 2C HAB1 reveal its role as a negative regulator of abscisic acid signalling", The Plant Journal, 37:354-369 (2004).
Reyes et al., "Overexpression of a Protein Phosphatase 2C from Beech Seeds in Arabidopsis Shows Phenotypes Related to Abscisic Acid Responses and Gibberellin Biosynthesis", Plant Physiology, 141:1414-1424 (2006).
Gonzalez-Garcia et al., "Negative Regulation of Abscisic Acid Signaling by the Fagus sylvatica FsPP2C1 Plays a Role in Seed Dormancy Regulation and Promotion of Seed Germination", Plant Physiology, 133:135-144 (2003).
Koesema et al., "Arabidopsis cDNA Clones", Accession No. AAK91405, dated Aug. 20, 2001 (Unpublished), ncbi.nlm.nih.gov/sviewer/viewer.fcgi?tool=portal&sendto=on&log$-seqv . . . (dated Jan. 20, 2012).
Kim et al., "Arabidopsis ORF Clones", Accession No. AAM10415, dated Apr. 13, 2002 (Unpublished), ncbi.nlm.nih.gov/sviewer/viewer.fcgi?tool=portal&sendto=on&log$-seqv . . . (dated Jan. 20, 2012).
Lin et al., "Arabidopsis thaliana chromosome III BAC F18C1 Genomic Sequence", Accession No. AAF26133, dated Oct. 30, 2002 (Unpublished), ncbi.nlm.nih.gov/sviewer/viewer.fcgi?tool=portal&sendto=on&log$-seqv . . . (dated Jan. 20, 2012).
Totoki et al., "Large-Scale Analysis of RIKEN Arabidopsis Full-length (RAFL) cDNAs", Accession No. BAF00337, dated Jul. 27, 2006 (Unpublished), ncbi.nlm.nih.gov/sviewer/viewer.fcgi?tool=portal&sendto=on&log$-seqv . . . (dated Jan. 20, 2012).
Sato et al., "Structural Analysis of Arabidopsis Thaliana Chromosomes 3. I. Sequence Features of the Regions of 4,504,864 bp Covered by Sixty P1 and TAC Clones", Accession No. BAA95773, dated Feb. 14, 2004, DNA Res, 7(2):131-135, ncbi.nlm.nih.gov/sviewer/viewer.fcgi?tool=portal&sendto=on&log$-seqv . . . (dated Jan. 20, 2012).
Meinkoth et al., "Hybridization of Nucleic Acids Immobilized on Solid Supports", Analytical Biochemistry, 138:267-284 (1984).
Office Action issued in U.S. Appl. No. 12/922,432, dated Jan. 31, 2014.
Kenji Komatsu, et al., "An analysis of ABA-signal transduction via protein phosphtase 2C in Physcomitrella patens", Japanese Society for Plant Cell and Molecular Biologi Talkai Symposium Koen Yoshishu, Aug. 8, 2007, p. 143.
Kenji Komatsu, et al., "An analysis of ABA-signal transduction via protein phosphtase 2C in Physcomitrella patens", The Japanese Society of Plant Physiologists Nenkai Yoshishu, Mar. 15, 2007, pp. 131, 1pD03 (166).
Hiroki Sugimoto, et al., "Functional analysis of a novel isoform of Arabidopsis PP2C, AtPP2CF1", Annual Meeting of the Molecular Biology Society of Japan Koen Yoshishu, Nov. 20, 2009, 3P-0501 poster.
Restriction Requirement issued in U.S. Appl. No. 12/922,432, dated Nov. 14, 2013.
Hu et al., "The Structure and Function of Protein Phosphatase 2Cs in Higher Plants", Chinese Journal of Cell Biology, 27:29-34 (2005).
Schafleitner et al., "Field Screening for Variation of Drought Tolerance in Solanum tuberosum L. By Agronomical, Physiological and Genetic Analysis", Potato Research, 2007, pp. 71-85, vol. 50.
Julija Umbrasaite et al., "Substrate Analysis of Arabidopsis PP2C-Type Protein Phosphatases", N. Dissmeyer and A. Schnittger (eds.), Plant Kinases: Methods and Protocols, Methods in Molecular Biology, vol. 779, 2011, pp. 149-161.
Michael Meinhard et al., "Hydrogen peroxide is a regulator of ABI1, a protein phosphatase 2C from Arabidopsis", FEBS Letters, 2001, 508:443-446.
Office Action, dated Jan. 15, 2016, issued by the United States Patent and Trademark Office in U.S. Appl. No. 12/922,432.
Communication from the United States Patent and Trademark Office, issued Jun. 8, 2016, in U.S. Appl. No. 12/922,432.
Sinclair et al., "Crop transformation and the challenge to increase yield potential", Trends in Plant Science, Feb. 2004, vol. 9, No. 2, pp. 70-75.
Radke et al., "Transformation and regeneration of Brassica rapa using Agrobacterium tumefaciens", Plant Cell Reports, 1992, vol. 11, pp. 499-505.
Bower et al., "Transgenic sugarcane plants via microprojectile bombardment", The Plant Journal, 1992, vol. 2, No. 3, pp. 409-416.

* cited by examiner

Fig. 1-1

CLUSTAL W (1.83) multiple sequence alignment

```
AT5G26010      MGHCFSLPS-------SQSEIHEDNEHGDGNVVCYGEEFGLDQDLPVH----------------
AT4G32950      MGFCFCLSSG---GSTDKSQIYEITDYGQENAVLYSDHHVVPQN--------------------
AT1G16220      MGLCHSKIDKTTRKETG-ATSTATT--TVERQS-SGRLRRPRDLYSGG----------------
AT1G79630      MGLCYS-VDRTTGKEPGEASSTATTAETVEERSGSGRWRRPRDLKGGG----------------
At1g03590      ------------MHRPCLGMGCCGS---KMGKRGFSDRMVSLHNLVS-----------------
AT3G02750      MGSCLSAE-----SRSPRPGSPCSPAFSVRKRKNSKKRPGSRNSSFDYR---------------
AT5G36250      MGSCLSSSGGGGSRRSLHGSPHVPGPGRRKRP-PKRRPGSCSSSFDNT----------------
AT5G01700      MGVCCS------------KGTGIIVEHGADDGNECGDGEAEVRDTNDG----------------
AT3G05640      MGHFSS-------MFNGIARSFSIKKAKNINSSKSYAKEATDEMAREAK---------------
AT5G27930      MGHFSS-------MFNGLARSFSIKKVKNNNGN-CDAKEAADEMASEAK---------------
AT3G16800      MVLLPA-------FLDGLARTVSTKKGKKLSEDEDGGREIAKSMIKDSK---------------
AT2G20050      MGCAYSKTCIGQICATKENSIRQTHQQAPSRGGTRATAAAAAVEEDNPVFNFSSDAVDDV
AT3G06270      MGCVQCKCCS------------RYPSSSDGDSRGPLEANGVLK---------------------

AT5G26010      ----------------------------------RLGSVCSIQGTKV------
AT4G32950      ----------------------------------LGSVSSLAGGKG-------
AT1G16220      -------------------EISEIQQVVGRLVGNGSSEIACLYTQQGKKG----
AT1G79630      -------------------DIEGIPQVLGRLVSNGSSKIACLYTQQGKKG----
At1g03590      ----------------------IPNRIIGNGKSRSSCIFTQQGRKG--------
AT3G02750      -------------------REEPLNQVPGRMFLNGSTEVACIYTQQGKKG----
AT5G36250      -------------------EEPLLHRIPGRMFLNGSTDVSLFSQQGKKG-----
AT5G01700      ------------------------AVVRTRGSSKHVSMSIKQGKKG--------
AT3G05640      -------------------KKELILRSSGCINADGSNNLASVFSRRGEKG----
AT5G27930      -------------------KKELILKSSGYVNVQGSNNLASLFSKRGEKG----
AT3G16800      -------------------KNSTLLGTSGFVSSESSKRFTSICSNRGEKG----
AT2G20050      DNDEIHQLGLSRDQEWGITRLSRVSSQFLPPDGSRVVKVPSCNYELRCSFLSQRGYYPDA
AT3G06270      ----------GKDQ------------KPLGS---IHVPSPNFDMVYSVLSQRGYYPDS
                                                       |              |

AT5G26010      ----LNQDHAVLYQGYGTR-DTELCGVFDGHGKNGHMVSKMVRNRLPSVLLALKEELNQES
AT4G32950      ----LNQDAAILHLGYGTE-EGALCGVFDGHGPRGAFVSKNVRNQLPSILLG----HMNNHS
AT1G16220      ----TNQDAMLVWENFCSRSDTVLCGVFDGHGPFGHMVSKRVRDMLPFTLSTQLKTTSGTE
AT1G79630      ----TNQDAMLVFENFCSRDDTVFCGVFDGHGPFGHMVAKKVRDTLPFTLLTQLKMTSESD
At1g03590      ----INQDAMIVWEDFMSK-DVTFCGVFDGHGPHGHLVARKVRDSLPVKLLSLLNSIK-SK
AT3G02750      ----PNQDAMVVWENFGSRTDTIFCGVFDGHGPYGHMVAKRVRDNLPLKLSAYWEAKVPVE
AT5G36250      ----PNQDAMIVWENFGSMEDTVFCGVFDGHGPYGHIVAKRVRDLLPLKLGSHLESYVSPE
AT5G01700      ----INQDAMTVWENFGGEEDTIFCGVFDGHGPMGHKISRHVCENLPSRVHSKIRSSKSAG
AT3G05640      ----VNQDCAIVWEGYGCQEDMIFCGIFDGHGPWGHFVSKQVRNSMPISLLCNWKETLSQT
AT5G27930      ----VNQDCALVWEGFGCQEDMIFCGIFDGHGPWGHYVAKQVRNSMPLSLLCNWQKILAQA
AT3G16800      ----INQDRAIVWEGFGCQEDITFCGMFDGHGPWGHVIAKRVKKSFPSSLLCQWQQTLASL
AT2G20050      LDKANQDSFAIHTPFGSNSDDHFFGVFDGHGEFGAQCSQFVKRRLCENLLRHGRFRVDPA
AT3G06270      PDKENQDTYCIKTELQGNPNVHFFGVFDGHGVLGTQCSNFVKERVVEMLSEDPTLLEDPE
                   ***     :       :  *:*****  *    ..   *   .     :

AT5G26010      NVCEEEAS------------------------------------------------------K
AT4G32950      -VTRDWKL------------------------------------------------------I
AT1G16220      QSSSKNGLNSAPTCVDEE------------------QWCELQLCEKDEKLFPEMYLP
AT1G79630      QSSLVGANGFQIKCTEEEEVQTTESEQVQKTESVTTMDEQWCELNPVNND-ELPEMYLP
At1g03590      QNGPIGTRASKSDSLEAE------------------------KEESTEED-----KLNFL
AT3G02750      GVLKAITTDTVNNVTNINNPEDAAAAAAFVTAE-----EEPRTSADMEEENTETQPELFQT
AT5G36250      EVLKEISLNTDD----------RKISEDLVHISAN-----GESRVYN-----KDYVKDQ-DMIQM
AT5G01700      DENIENNSSQSQE------------------------------------------------ELFRE
AT3G05640      TIA--------EPDKELQR-------------------------------------------FAI
AT5G27930      TLEPELDLEGSNKKISR---------------------------------------------FDI
AT3G16800      SSS--------PECSSP---------------------------------------------FDL
AT2G20050      -------------------------------------------------------------------
AT3G06270      -------------------------------------------------------------------
```

Fig. 1-2

```
                                                      II
AT5G26010    WEKACFTAFRLIDRELNL--QVFNCSFSGSTGVVAITQGDDLVIANLGDSRAVLGTMTEDG
AT4G32950    CETSCLEMDKRILKVK----KIHDCSASGTTAVLAVKHGNQVMVANLGDSRAVMIGTSEDG
AT1G16220    LKRALLKTCQQMDKELKMHPTINCFCSGTTSVTVIKQGKDLVVGNIGDSRAVLATRDQDN
AT1G79630    LKHAMLKSCQQIDKELKMHPTIDCFCSGTTSVTLIKQGEDLVVGNIGDSRAVLATRDEDN
At1g03590    WEEAFLKSFNAMDKELRSHPNLECFCSGCTAVTIIKQGSNLYMGNIGDSRAILGSKDSND
AT3G02750    LKESFLKAFKVMDRELKFHGSVDCFCSGTTAVTLIKQGQYLVVGNVGDSRAVMGTRDSEN
AT5G36250    LIGSIVKAYRFMDKELKMQVDVDCFCSGTTAVTMVKQGQHLVIGNIGDSRAVLGVRNKDN
AT5G01700    FEDILVTFFKQIDSELGLDSPYDSFCSGTTAVTVFKQADCLVIANLGHSRAVLGTR-SKN
AT3G05640    WKYSFLKTCEAVDLELEHHRKIDSFNSGTTALTIVRQGDVIYIANVGDSRAVLATVSDEG
AT5G27930    WKQSYLKTCATVDQELEHHRKIDSYYSGTTALTIVRQGEVIYVANVGDSRAVLAMESDEG
AT3G16800    WKQACLKTFSIIDLDLKISPSIDSYCSGCTALTAVLQGDHLVIANAGDSRAVIATTSDDG
AT2G20050    ---EACNSAFLTTNSQLH-ADLVDDSMSGTTAITVMVRGRTIYVANAGDSRAVLAEKRDGD
AT3G06270    ---KAYKSAFLRVNEELH-DSEIDDSMSGTTAITVLVVGDKIYVANVGDSRAVLAVKDRNR
                         :  ** *.:  .  . :  .:..*   *,.***::

AT5G26010    E-IKAVQLTSDLTPDVP-----------------------------------SEAERIRM
AT4G32950    E-TKVAQLTNDLKPSVP-----------------------------------SEAERIRK
AT1G16220    A-LVAVQLTIDLKPDLP-----------------------------------SESARIHR
AT1G79630    A-LLAVQLTIDLKPDLP-----------------------------------GESARIQK
At1g03590    S-MIAVQLTVDLKPDLP-----------------------------------REAERIKQ
AT3G02750    T-LVAVQLTVDLKPNLPGWIILCECMMLSCGCMMDPLIMFIGFFFIPSIELAAEAERIRK
AT5G36250    K-LVPFQLTEDLKPDVP---------------------------------------AEAERIKR
AT5G01700    S-FKAVQLTVDLKPCVQ-----------------------------------REAERIVS
AT3G05640    S-LVAVQLTVDFKPNLP-----------------------------------QEEERIIG
AT5G27930    S-LVAVQLTLDFKPNLP-----------------------------------QEKERIIG
AT3G16800    NGLVPVQLSVDFKPNIP-----------------------------------EEAERIKQ
AT2G20050    L---VAVDLSIDQTPFRP----------------------------------DELERVKL
AT3G06270    I---LAEDLSYDQTPFRK----------------------------------DECERVKA
                  :*   *  .*                                     III              * *:

AT5G26010    CKGRVFAMKTEPSSQ----------------------RVWLPNQNIPGLAMSRAFGDFRLKDHG
AT4G32950    RNGRVLALESEPHIL----------------------RVWLPTENRPGLAMSRAFGDFLLKSYG
AT1G16220    CKGRVFALQDEPEVA----------------------RVWLPNSDSPGLAMARAFGDFCLKDYG
AT1G79630    CKGRVFALQDEPEVA----------------------RVWLPNSDSPGLAMARAFGDFCLKDYG
At1g03590    CKGRVFALQDEPEVS----------------------RVWLPFDNAPGLAMARAFGDFCLKDYG
AT3G02750    CRGRVFALRDEPEVC----------------------RVWLPNCDSPGLAMARAFGDFCLKDFG
AT5G36250    CRGRIFALRDEPGVA----------------------RLWLPNHNSPGLAMARAFGDFCLKDFG
AT5G01700    CKGRVFAMEEEPDVY----------------------RVWMPDDDCPGLAMSRAFGDFCLKDYG
AT3G05640    CNGRVFCLQDEPGVH----------------------RVWQPVDESPGLAMSRAFGDYCIKDYG
AT5G27930    CKGRVFCLDDEPGVH----------------------RVWQPDAETPGLAMSRAFGDYCIKEYG
AT3G16800    SDGRLFCLDDEPGVY----------------------RVGMPNGGSLGLAVSRAFGDYCLKDFG
AT2G20050    CGARVLTLDQIEGLKNPDVQCWGTEEDDDGDPPRLWVPNGMYPGTAFTRSIGDSIAETIG
AT3G06270    CGARVLSVDQVEGLKDPNIQTWANEESEGGDPPRLWVQNGMYPGTAFTRSVGDFTAESIG
             .*::  :                              *:            * *:.**   : *

AT5G26010    VIAVPEISQHRITSKDQFLVLATDGVWDMLSNDEVVSLIWSSGKKQASAAKMVAEAAEAA
AT4G32950    VIATPQVSTHQITSSDQFLLLASDGVWDVLSNEEVATVVMKSAS-EAGAANEVAEAATNA
AT1G16220    LISVPDINYHRLTERDQYIILATDGVWDVLSNKEAVDIVASAPS-RDTAARAVVDTAVRA
AT1G79630    LISVPDINYRRLTERDQFIILASDGVWDVLSNKEAVDIVASAPS-RSTAARALVDTAVRS
At1g03590    VISIPEFSHRVLTDRDQFIVLASDGVWDVLSNEEVVEVVASATS-RASAARLVVDSAVRE
AT3G02750    LISVPDVSFRQLTEKDEFIVLATDGIWDVLSNEDVVAIVASAPS-RSSAARALVESAVRA
AT5G36250    LISVPDVSYRRLTEKDEFVVLATDGIWDALTNEEVVKIVAKAPT-RSSAGRALVEAAVRN
AT5G01700    LVCIPDVFCRKVSREDEFVVLATDGIWDVLSNEEVVKVVGSCKD-RSVAAEMLVQRAART
AT3G05640    LVSVPEVTQRHISIRDQFIILATDGVWDVISNQEAIDIVSSTAE-RAKAAKRLVQQAVRA
AT5G27930    LVSVPEVTQRHISTKDHFIILASDGIWDVISNQEAIEIVSSTAE-RPKAAKRLVEQAVRA
AT3G16800    LVSEPEVTYRKITDKDQFLILATDGMWDVMTNNEAVEIVRGVKE-RRKSAKRLVERAVTL
AT2G20050    VVANPEIAVVELTPDNPFFVVASDGVFEFISSQTVVDMVAKHKD-PRDACAAIVAESYRL
AT3G06270    VIAEPEVSMVHLSPNHLFFVVASDGIFEFLPSQAVVDMVGRYAD-PRDGCAAAAAESYKL
             ::.  *:.   ::   .   :.:*.**::   :...  ::.         .  .    :
```

Fig. 1-3

```
AT5G26010   WKKRLKYTKVDDITVICLFLQNKEQPS---------------------------------
AT4G32950   WIQKFPTVKIDDISVVCLSLNKKHNPQPQI-------------------------------
AT1G16220   WRLKYPTSKNDDCAVVCLFLEDTSAGGTVEVSETVNHSHEESTESVTITSSKDADKKEEA
AT1G79630   WRIKYPTSKNDDCTVVCLFLQDSSVAMEVSTNVKKDSPKEESIESVTNSTSKEED------
At1g03590   WKLKYPTSKMDDCAVVCLFLDG----RMDSETSDNEEQCFSSATNAVESDESQGAEP----
AT3G02750   WRYKYPTSKVDDCAAVCLYLDSSNTNAISTASSISKLEDGEEEELKATTEDDDASG----
AT5G36250   WRWKFPTSKVDDCAVVCLFLDS-EPNRLSTAS----------------------------
AT5G01700   WRTKFPASKADDCAVVVLYLNHRPYPREGNVS----------------------------
AT3G05640   WNRKRRGIAMDDISAVCLFFHSSSSSPSL-------------------------------
AT5G27930   WKKKRRGYSMDDMSVVCLFLHSSSSS-SLSQHHHAMTILK--------------------
AT3G16800   WRRKRRSIAMDDISVLCLFFRPS-------------------------------------
AT2G20050   WLQY--ETRTDDITIIVVHIDGLKDDAPRQLSSTGTQLQPPIPQVVELTGSESPSTFGWN
AT3G06270   WLEH---ENRTDDITIIIVQIKKLSNE---------------------------------
            *       **  : : :

AT5G26010   ------------------------------------------------------------
AT4G32950   ------------------------------------------------------------
AT1G16220   STETNETVPVWEIKEEKTPESCRIESKKT---TLAECISVK-DDEEWSALEGLTRVNSLLS
AT1G79630   -------EIVP----VKDEKIPESCGIESKMMTMTLAECISVAQDDEEWSALEGLTRVNSLLS
At1g03590   --CLQRNVTVRSLSTDQENNSYGKVIAEA---DNAEKEKTREGEQNWSGLEGVTRVNSLVQ
AT3G02750   -PSGLGRSSTVRSGKEIALDESETEKLIK------EADNLDSEPGTEYSALEGVARVNTLLN
AT5G36250   ---------------FSKEKHINNGVTEPEPD------TASSSTPDSGTGSPELNGVNRIDTLVN
AT5G01700   ------------------RAISTISWRSNKS--------NNECYGAAPLSPLGLSQRVS----
AT3G05640   ------------------------------------------------------------
AT5G27930   ------------------------------------------------------------
AT3G16800   ------------------------------------------------------------
AT2G20050   SKNQRVRHDLSRARIRAIENSLENGHAWVPPSPAHRKTWEEEVRVLVCFVFAQPIRNASS
AT3G06270   ------------------------------------------------------------

AT5G26010   ------------------
AT4G32950   ------------------
AT1G16220   IPRFFSGELRSSSWRKWL
AT1G79630   IPRFLSGELRSTSWRKWL
At1g03590   LPRFPGEEPKT-------
AT3G02750   LPRFVPGK----------
AT5G36250   LPVYVPTKE---------
AT5G01700   ------------------
AT3G05640   ------------------
AT5G27930   ------------------
AT3G16800   ------------------
AT2G20050   HSYIRRLNAGFSRAGTH-
AT3G06270   ------------------
```

Fig. 2-1

CLUSTAL W (1.83) multiple sequence alignment

```
AT1G16220    MGLCHSKIDKTTRKETG-ATSTATT--TVERQS-SGRLRRPRDLYSGGEISEIQQVVGRL
AT1G79630    MGLCYS-VDRTTGKEPGEASSTATTAETVEERSGSGRWRRPRDLKGGGDIEGIPQVLGRL
At1g03590    ------------MHRPCLGMGCCGS--KMGKRGFSDRMVSLHNLVS----------IPNRI
AT3G02750    MGSCLSAE----SRSPRPGSPCSPAFSVRKRKNSKKRPGSRNSSFDYRREEPLNQVPGRM
AT5G36250    MGSCLSSSGGGGSRRSLHGSPHVPGPGRRKRP-PKRRPGSCSSSFDNTEEPLLHRIPGRM
AT5G26010    MGHCFSLPS-----SQSEIHEDNEHGDG-NVVCYGEEFGLDQDLPVH-------------
AT4G32950    MGFCFCLSSGGSTDKSQIYEITDYGQE-NAVLYSDHHVVPQN------------------
AT5G01700    MGVCCSKGTG-IIVEHGADDGNECGDGEAEVRDTNDGAVVRTRGSS--------------
AT3G05640    MGHFSSMFNGIARSFSIKKAKNINSSKSYAKEATDEMAREAKKKELILR-------SSGCI
AT5G27930    MGHFSSMFNGLARSFSIKKVKNNNGN-CDAKEAADEMASEAKKKELILK-------SSGYV
AT3G16800    MVLLPAFLDGLARTVSTKKGKKLSEDEDGGREIAKSMIKDSKKNSTLLG-------TSGFV
                                                              I
                                                         ┌─────────┐
AT1G16220    VGNGSSEIACLYTQQGKKGTNQDAMLVWENFCSRSDTVLCGVFDGHGPFGHMVSKRVRDM
AT1G79630    VSNGSSKIACLYTQQGKKGTNQDAMLVFENFCSRDDTVFCGVFDGHGPFGHMVAKKVRDT
At1g03590    IGNGKSRSSCIFTQQGRKGINQDAMIVWEDFMSK-DVTFCGVFDGHGPHGHLVARKVRDS
AT3G02750    FLNGSTEVACIYTQQGKKGPNQDAMVVWENFGSRTDTIFCGVFDGHGPYGHMVAKRVRDN
AT5G36250    FLNGSTDTVSLFSQQGKKGPNQDAMIVWENFGSMEDTVFCGVFDGHGPYGHIVAKRVRDL
AT5G26010    --------RLGSVCSIQGTKVLNQDHAVLYQGYG-TRDTELCGVFDGHGKNGHMVSKMVRNR
AT4G32950    ---------LGSVSSLAGGKGLNQDAAILHLGYG-TEEGALCGVFDGHGPRGAFVSKNVRNQ
AT5G01700    --------KHVSMSIKQGKKGINQDAMTVWENFGGEEDTIFCGVFDGHGPMGHKISRHVCEN
AT3G05640    NADGSNNLASVFSRRGEKGVNQDCAIVWEGYGCQEDMIFCGIFDGHGPWGHFVSKQVRNS
AT5G27930    NVQGSNNLASLFSKRGEKGVNQDCALVWEGFGCQEDMIFCGIFDGHGPWGHYVAKQVRNS
AT3G16800    SSESSKRFTSICSNRGEKGINQDRAIVWEGFGCQEDITFCGMFDGHGPWGHVIAKRVKKS
              .:   * * ***   :  .:    : :**:*****  *   ::: * .
                                           └────────────┘

AT1G16220    LPFTLSTQLKTTSGTEQSSSKNGLNSAPTCVDEE---------------------QWCEL
AT1G79630    LPFTLLTQLKMTSESDQSSLVGANGFQIKCTEEEEVQTTESEQVQKTESVTTMDEQWCEL
At1g03590    LPVKLLSLLNSIK-SKQNGPIGTRASKSDSLEAE----------------------K
AT3G02750    LPLKLSAYWEAKVPVEGVLKAITTDTVNNVTNINNPEDAAAAAAFVTAEEEPRTSADMEE
AT5G36250    LPLKLGSHLESYVSPEEVLKEISLNTDD---------RKISEDLVHISANGESRVYN---K
AT5G26010    LPSVLLALK----------EELNQESNVCE------------------------
AT4G32950    LPSILLG-------------HMNNHS-VTR------------------------
AT5G01700    LPSRVHSKIRSSKSAGDENIENNSSQSE--------------------------
AT3G05640    MPISLLCNWK---------ETLSQTTIA--------------------------
AT5G27930    MPLSLLCNWQ---------KILAQATLEPE------------------------
AT3G16800    FPSSLLCQWQ---------QTLASLSSS--------------------------
              :*  :                                      II
                                                       ┌─────────┐
AT1G16220    QLCEKDEKLFPEMYLPLKRALLKTCQQMDKELKMHPTINCFCSGTTSVTVIKQGKDLVVG
AT1G79630    NPNVNND-ELPEMYLPLKHAMLKSCQQIDKELKMHPTIDCFCSGTTSVTLIKQGEDLVVG
At1g03590    EESTEED----KLNFLWEEAFLKSFNAMDKELRSHPNLECFCSGCTAVTIIKQGSNLYMG
AT3G02750    ENTETQP----ELFQTLKESFLKAFKVMDRELKFHGSVDCFCSGTTAVTLIKQGQYLVVG
AT5G36250    DYVKDQ-------DMIQMLIGSIVKAYRFMDKELKMQVDVDCFCSGTTAVTMVKQGQHLVIG
AT5G26010    ------------EEASKWEKACFTAFRLIDRELNL-QVFNCSFSGTGVVAITQGDDLVIA
AT4G32950    ------------DWKLICETSCLEMDKRILKVK----KIHDCSASGTTAVLAVKHGNQVMVA
AT5G01700    ------------ELFREFEDILVTFFKQIDSELGLDSPYDSFCSGTTAVTVFKQADCLVIA
AT3G05640    -----EPDKELQRFAIWKYSFLKTCEAVDLELEHHRKIDSFNSGTTALTIVRQGDVIYIA
AT5G27930    -LDLEGSNKKISRFDIWKQSYLKTCATVDQELEHHRKIDSYYSGTTALTIVRQGEVIYVA
AT3G16800    ------------PECSSPFDLWKQACLKTFSIIDLDLKISPSIDSYCSGCTALTAVLQGDHLVIA
                 .     .         :   ** *.: . ,   .  :
```

Fig. 2-2

```
AT1G16220    NIGDSRAVLATRDQDNA-LVAVQLTIDLKPDLP--------------------------------
AT1G79630    NIGDSRAVLATRDEDNA-LLAVQLTIDLKPDLP--------------------------------
At1g03590    NIGDSRAILGSKDSNDS-MIAVQLTVDLKPDLP--------------------------------
AT3G02750    NVGDSRAVMGTRDSENT-LVAVQLTVDLKPNLPGWIILCECMMLSCGCMMDPLIMFIGFF
AT5G36250    NIGDSRAVLGVRNKDNK-LVPFQLTEDLKPDVP--------------------------------
AT5G26010    NLGDSRAVLGTMTEDGE-IKAVQLTSDLTPDVP--------------------------------
AT4G32950    NLGDSRAVMIGTSEDGE-TKVAQLTNDLKPSVP--------------------------------
AT5G01700    NLGHSRAVLGTRSKNS--FKAVQLTVDLKPCVQ--------------------------------
AT3G05640    NVGDSRAVLATVSDEGS-LVAVQLTVDFKPNLP--------------------------------
AT5G27930    NVGDSRAVLAMESDEGS-LVAVQLTLDFKPNLP--------------------------------
AT3G16800    NAGDSRAVIATTSDDGNGLVPVQLSVDFKPNIP--------------------------------
             * *.***::   .:.    **: *:.* :                          III

AT1G16220    ------------SESARIHRCKGRVFALQDEPEVARVWLPNSDSPGLAMARAFGDFCLKDYGLI
AT1G79630    ------------GESARIQKCKGRVFALQDEPEVARVWLPNSDSPGLAMARAFGDFCLKDYGLI
At1g03590    ------------REAERIKQCKGRVFALQDEPEVSRVWLPFDNAPGLAMARAFGDFCLKDYGVI
AT3G02750    FIPSIELAAEAERIRKCRGRVFALRDEPEVCRVWLPNCDSPGLAMARAFGDFCLKDFGLI
AT5G36250    ------------AEAERIKRCRGRIFALRDEPGVARLWLPNHNSPGLAMARAFGDFCLKDFGLI
AT5G26010    ------------SEAERIRMCKGRVFAMKTEPSSQRVWLPNQNIPGLAMSRAFGDFRLKDHGVI
AT4G32950    ------------SEAERIRKNGRVLALESEPHILRVWLPTENRPGLAMSRAFGDFLLKSYGVI
AT5G01700    ------------REAERIVSCKGRVFAMEEEPDVYRVWMPDDDCPGLAMSRAFGDFCLKDYGLV
AT3G05640    ------------QEEERIIGCNGRVFCLQDEPGVHRVWQPVDESPGLAMSRAFGDYCIKDYGLV
AT5G27930    ------------QEKERIIGCKGRVFCLDDEPGVHRVWQPDAETPGLAMSRAFGDYCIKEYGLV
AT3G16800    ------------EEAERIKQSDGRLFCLDDEPGVYRVGMPNGGSLGLAVSRAFGDYCLKDFGLV
                         *  **    **::.: **  *:  *    ***:.*****: :*..*::

AT1G16220    SVPDINYHRLTERDQYIILATDGVWDVLSNKEAVDIVASAPS-RDTAARAVVDTAVRAWR
AT1G79630    SVPDINYRRLTERDQFIILASDGVWDVLSNKEAVDIVASAPS-RSTAARALVDTAVRSWR
At1g03590    SIPEFSHRVLTDRDQFIVLASDGVWDVLSNEEVVEVVASATS-RASAARLVVDSAVREWK
AT3G02750    SVPDVSFRQLTEKDEFIVLATDGIWDVLSNEDVVAIVASAPS-RSSAARALVESAVRAWR
AT5G36250    SVPDVSYRRLTEKDEFVVLATDGIWDALTNEEVVKIVAKAPT-RSSAGRALVEAAVRNWR
AT5G26010    AVPEISQHRITSKDQFLVLATDGVWDMLSNDEVVSLIWSSGKKQASAAKMVAEAAEAAWK
AT4G32950    ATPQVSTHQITSSDQFLLLASDGVWDVLSNEEVATVVMKSAS-EAGAANEVAEAATNAWI
AT5G01700    CIPDVFCRKVSREDEFVVLATDGIWDVLSNEEVVKVVGSCKD-RSVAAEMLVQRAARTWR
AT3G05640    SVPEVTQRHISIRDQFIILATDGVWDVISNQEAIDIVSSTAE-RAKAAKRLVQQAVRAWN
AT5G27930    SVPEVTQRHISTKDHFIILASDGIWDVISNQEAIEIVSSTAE-RPKAAKRLVEQAVRAWK
AT3G16800    SEPEVTYRKITDKDQFLILATDGMWDVMTNNEAVEIVRGVKE-RRKSAKRLVERAVTLWR
             . *:.    : :: *.:::**:**:**    ::*.:.  ::        . :.. .:* *

AT1G16220    LKYPTSKNDDCAVVCLFLEDTSAGGTVEVSETVNHSHEESTESVTITSSKDADKKEEAST
AT1G79630    IKYPTSKNDDCTVVCLFLQDSSVAMEVSTNVKKDSPKEESIESVTNSTSKEED---------
At1g03590    LKYPTSKMDDCAVVCLFLDG---RMDSETSDNEEQCFSSATNAVESDESQGAEP---------
AT3G02750    YKYPTSKVDDCAAVCLYLDSSNTNAISTASSISKLEDGEEEELKATTEDDDASG------P
AT5G36250    WKFPTSKVDDCAVVCLFLDS-EPNRLSTAS----------------------------
AT5G26010    KRLKYTKVDDITVICLFLQN----------------------------
AT4G32950    QKFPTVKIDDISVVCLSLNK----------------------------
AT5G01700    TKFPASKADDCAVVVLYLNH----------------------------
AT3G05640    RKRRGIAMDDISAVCLFFHSSSSSPSL----------------------------
AT5G27930    KKRRGYSMDDMSVVCLFLHSSSSS-SLSQHHHAMTILK----------------------------
AT3G16800    RKRRSIAMDDISVLCLFFRPS----------------------------
             :    **  :  *  :
```

Fig. 2-3

| | |
|---|---|
| AT1G16220 | ETNETVPVWEIKEEKTPESCRIESKKT--TLAECISVK-DDEEWSALEGLTRVNSLLSIP |
| AT1G79630 | ---EIVP----VKDEKIPESCGIESKMMTMTLAECISVAQDDEEWSALEGLTRVNSLLSIP |
| At1g03590 | CLQRNVTVRSLSTDQENNSYGKVIAEA--DNAEKEKTREGEQNWSGLEGVTRVNSLVQLP |
| AT3G02750 | SGLGRSSTVRSGKEIALDESETEKLIK----EADNLDSEPGTEYSALEGVARVNTLLNLP |
| AT5G36250 | -----------FSKEKHINNGVTEPEPD------TASSSTPDSGTGSPELNGVNRIDTLVNLP |
| AT5G26010 | --------------KEQPS--------------------------------------- |
| AT4G32950 | --------------KHNPQPQI----------------------------------- |
| AT5G01700 | --------------RPYPREGNVSRAIS---------TISWRSNKSNNECYGAAPLSPLGLSQ |
| AT3G05640 | --------------------------------------------------------- |
| AT5G27930 | --------------------------------------------------------- |
| AT3G16800 | --------------------------------------------------------- |

| | |
|---|---|
| AT1G16220 | RFFSGELRSSSWRKWL |
| AT1G79630 | RFLSGELRSTSWRKWL |
| At1g03590 | RFPGEEPKT-------- |
| AT3G02750 | RFVPGK----------- |
| AT5G36250 | VYVPTKE---------- |
| AT5G26010 | ----------------- |
| AT4G32950 | ----------------- |
| AT5G01700 | RVS-------------- |
| AT3G05640 | ----------------- |
| AT5G27930 | ----------------- |
| AT3G16800 | ----------------- |

Fig. 3-1

CLUSTAL W (1.83) multiple sequence alignment

```
EEF02079      ---MACANLVKLNAASSSWIGQKSPFGQRSQGS----STRRVSFSIRANSYTDELVQTAKT
ABK94899      ---MACANLVKLNAASSSWIGQKSPFGQRSQGS----STRRVSFSIRANSYTDELVQTAKT
EEE88847      ---MACASFVKLNAASSSWTGQKSSFGKRSPGS----STRRVSFSIRASSYTDELVQTAKL
EEF36097      ---MACASFAKLNAASSTWIGQQS-FGQRPGSSSARFATRRVSLPIRASSYKDELVQTAKT
CA042215      ---MASVTFAKFNASSSQWIGQQS-FSQRQGSS-ARFPARRVSVPIRAGSYSEELVQTAKT
At2g01140     ---MASASFVKPNTLSSPWIGQRS-FAHTSASS---SPPPRVSFAIRAGAYSDELVKTAKS
ABK24286      -MAASVLKAGVRLGSSQWTGQSLTQNIDSHKQ----PKAQRVSMPIRAGSYAEELVQTAKT
ABK25226      -MAASVLKAGVRLGSSQWTGQSLTQNIDSHKQ----PKAQRVSMPIRAGSYAEELVQTAKT
ABK24568      -MAASVIKAGVRLGSSQWTGQSLTQNIDSHKQ----PKAQRVSMPIRAGSYAEELVQTAKT
ACG47464      MAMATAKLNSP---ATSLVAGGLTRRSAPARCT----------TVIRAAAGSYSDELISTAKS
ACG47669      MAMATAKLNSP---ATSLVAGGRTRRSAPARCT----------TVIRAAAGSYSDELISTAKS
Os01g0118000  MAMLTAKLTSPPAATTWLPGG-GRRSAPPRRA----------TVIRAAAVSYADELVSTAKS
                ::  *                               .  . * :* :**:.***

EEF02079      IASPGRGILAIDESNATCGKRLASIGLDNTETNRQAYRQLLLTTPSLGEYISGAILFEET
ABK94899      IASPGRGILAIDESNATCGKRLASIGLDNTETNRQAYRQLLLTTPSLGEYISGAILFEET
EEE88847      IASPGRGILAIDESNATCGKRLASIGLDNTETNRQAYRQLLLTTPGLGEYISGAILFEET
EEF36097      VASPGRGILAIDESNATCGKRLASIGLDNNETNRQAYRQLLLTTPGLGEYISGAILFEET
CA042215      VASPGRGILAIDESNATCGKRLASIGLDNTEPNRQAYRQLLLTTPGLGEYISGAILFEET
At2g01140     IASPGRGILAIDESNATCGKRLASIGLDNTEDNRQAYRQLLLTTPGLGDYISGSILFEET
ABK24286      VASPGRGILAIDESNATCGKRLASIGLENNETNRQAYRQLLLTTPGLGEYISGSILFEET
ABK25226      VASPGRGILAIDESNATCGKRLASIGLENNETNRQAYRQLLLTTPGLGEYISGSILFEET
ABK24568      VASPGRGILAIDESNATCGKRLASIGLENNETNRQAYRQLLLTTPGLGEYISGSILFEET
ACG47464      VASPGRGILAIDESNATCGKRLSSIGLDNTEVNRQAYRQLLLTTAGLGEYISGAILFEET
ACG47669      VASPGRGILAIDESNATCGKRLSSIGLDNTEVNRQAYRQLLLTTAGLGEYISGAILFEET
Os01g0118000  VASPGRGILAIDESNATCGKRLASIGLDNTEVNRQAYRQLLLTTAGLGEYISGAILFEET
              :********************:****:*.* ************..**:****:******

EEF02079      LYQSTTDGKKFVDCLRDENIVPGIKVDKGLVPLPGSNNESWCQGLDGLASRSAEYYKQGA
ABK94899      LYQSTTDGKKFVDCLRDENIVPGIKVDKGLVPLPGSNNESWCQGLDGLASRSAEYYKQGA
EEE88847      LYQSTTDGRKFVDCLRDENIVPGIKVDKGLVPLPGSNNESWCQGLDGLASRSAEYYKQGA
EEF36097      LYQSTTDGKKFVDCLRDQNIVPGIKVDKGLVPLPGSNNESWCQGLDGLASRSAEYYKQGA
CA042215      LYQSTTDGKKFVDCLREKKIVPGIKVDKGLVPLPGSNNESWCQGLDGLASRSAEYYKQGA
At2g01140     LYQSTKDGKTFVDCLRDANIVPGIKVDKGLSPLAGSNEESWCQGLDGLASRSAEYYKQGA
ABK24286      LYQSTTDGRKFVDCLREQNIMPGIKVDKGLVPLPGSNNESWCQGLDGLASRSAEYYKQGA
ABK25226      LYQSTTDGRKFVDCLREQNIMPGIKVDKGLVPLPGSNNESWCQGLDGLASRSAEYYKQGA
ABK24568      LYQSTTDGRKFVDCLREQNIMPGIKVDKGLVPLPGSNNESWCQGLDGLASRSAEYYKQGA
ACG47464      LYQSTTDGKKFVDCLKDQNIMPGIKVDKGLVPLPGSNNESWCQGLDGLASRCAEYYKQGA
ACG47669      LYQSTTDGKKFVDCLKDQNIMPGIKVDKGLVPLPGSNNESWCQGLDGLASRCAEYYKQGA
Os01g0118000  LYQSTTDGKKFVDCLKDQNIMPGIKVDKGLVPLPGSNNESWCQGLDGLASRCAEYYKQGA
              *****.**:.*****:.  :*:********* **.**:***********.*******
```

Fig. 3-2

```
EEF02079      RFAKWRTVVSIPCGPSALAVKEAAWGLARYAAISQDNGLVPIVEPEILLDGDHPIDRTLE
ABK94899      RFAKWRTVVSIPCGPSALAVKEAAWGLARYAAISQDNGLVPIVEPEILLDGDHPIDRTLE
EEE88847      RFAKWRTVVSIPCGPSALAVKEAAWGLARYAAISQDNGLVPIVEPEILLDGDHPIDRTLE
EEF36097      RFAKWRTVVSIPCGPSALAVKEAAWGLARYAAISQDNGLVPIVEPEILLDGDHGIERTLE
CA042215      RFAKWRTVVSIPCGPSALAVKEAAWGLARYAAISQDNGLVPIVEPEILLDGDHPIDRTLE
At2g01140     RFAKWRTVVSVPCGPSALAVKEAAWGLARYAAISQDNGLVPIVEPEILLDGDHPIERTLE
ABK24286      RFAKWRTVVSIPNGPSDLAVKEAAWGLARYAAISQDNGLVPIVEPEILLDGDHSIDRTLE
ABK25226      RFAKWRTVVSIPNGPSDLAVKEAAWGLARYAAISQDNGLVPIVEPEILLDGDHSIDRTLE
ABK24568      RFAKWRTVVSIPNGPSDLAVKEAAWGLARYAAISQDNGLVPIVEPEILLDGDHSIDRTLE
ACG47464      RFAKWRTVVSIPCGPSALAVKEAAWGLARYAAIAQDNGLVPIVEPEILLDGDHGIEGALE
ACG47669      RFAKWRTVVSIPCGPSALAVKEAAWGLARYAAIAQDNGLVPIVEPEILLDGDHGIEGALE
Os01g0118000  RFAKWRTVVSIPCGPSALAVKEAAWGLARYAAIAQDNGLVPIVEPEILLDGDHAIERTLE
              **********:* *** ****************:****************** *: :**

EEF02079      VAEKVWSEVFYYLAENNVVFEGILLKPSMVTPGAEHKEKASADTIAKYTLTMLKRRVPPA
ABK94899      VAEKVWSGVFYYLAENNVVFEGILLKPSMVTPGAEHKEKASADTIAKYTLTMLKRRVPPA
EEE88847      VAEKVWAEVFYYLAENNVVFEGILLKPSMVTPGAEHKEKASPDTIAKYTLTMLRRRVPPA
EEF36097      VAEKVWAEVFFYLAENNVVFEGILLKPSMVTPGAEHKEKASPDTIAKYTLTMLRRRVPPA
CA042215      VAEKVWSEVFFYLAQNNVLFEGILLKPSMVTPGAEHKEKASPETIAKYTLTMLRRRVPPA
At2g01140     VAEKVWSEVFFYLAQNNVMFEGILLKPSMVTPGAEHKNKASPETVADFTLTMLKRRVPPA
ABK24286      VAEKVWAEVFFYLAENNVFFEGILLKPSMVTPGAEHKEKATPQQVADYTLKMLKRRVPPA
ABK25226      VAEKVWAEVFFYLAENNVFFEGILLKPSMVTPGAEHKEKATPQQVADYTLKMLKRRVPPA
ABK24568      VAEKVWAEVFFYLAENNVLFEGILLKPSMVTPGAEHKEKASPEAIAKYTLTMLRRRVPPA
ACG47464      VAEKVWSEVFFYLAENNVLFEGILLKPSMVTPGAEHKEKASPEAIAKYTLTMLRRRVPPA
ACG47669      VAEKVWSEVFFYLAENNVLFEGILLKPSMVTPGAEHKEKASPEAIAKYTLTMLRRRVPPA
Os01g0118000  VAEKVWSEVFFYLAQNNVLFEGILLKPSMVTPGAEHKQKATPEAIAKHTLTMLRRRVPPA
              ******: **:***:***.**************.**::.: *..**.**:******

EEF02079      VPGIMFLSGGQSEVQATLNLNAMNQSPNPWHVSFSYARALQNTVLKTWQGRPDNVEAAQK
ABK94899      VPGIMFLSGGQSEVQATLNLNAMNQSPNPWHVSFSYARALQNTVLKTWQGRPDNVEAAQK
EEE88847      VPGIMFLSGGQSEVQATLNLNAMNQSPNPWHVSFSYARALQNTVLKTWQGGHPENVEAAQK
EEF36097      VPGIMFLSGGQSEVEATLNLNAINQSPNPWHVSFSYARALQNSVLKTWQGHPENVEAAQK
CA042215      VPGIMFLSGGQSEVEATLNLNAMNQSPNPWHVSFSYARALQNTVLKTWQGHPENVEAAQK
At2g01140     VPGIMFLSGGQSEAEATLNLNAMNQSPNPWHVSFSYARALQNSVLRTWQGKPEKIEASQK
ABK24286      VPGIMFLSGGQSEVEATLNLNAMNQSPNPWHVSFSYARALQNTSLKTWKGLPENIEAAQR
ABK25226      VPGIMFLSGGQYEVEATLNLNAMNQSPNPWHVSFSYARALQNTSLKTWKGLPENIEAAQR
ABK24568      VPGIMFLSGGQSEVEATLNLNAMNQSPNPWHVSFSYARALQNTSLKTWKGLPENIEAAQR
ACG47464      VPGIMFLSGGQSEVEATLNLNAMNQSLNPWHVSFSYVRALQNSVLKTWQGRPENVEAAQK
ACG47669      VPGIMFLSGGQSEVEATLNLNAMNQSLNPWHVSFSYVRALQNSVLKTWQGRPENVEAAQK
Os01g0118000  VPGIMFLSGGQSEVEATLNLNAMNQEPNPWHVSFSYARALQNSVLKTWQGRPENVEAAQK
              *********** *.:*******:**. ********.*****:  *:**:* *:::**:*:

EEF02079      SLLVRAKANSLAQLGRYSAEGESEEATKGMFVKGYTY----------
ABK94899      SLLVRAKANSLAQLGRYSAEGESEEATKGMFVKGYTY----------
EEE88847      SLLVRAKANSLAQLGRYSAEGESEEAKKGMFVKGYTY----------
EEF36097      ALLVRAKANSLAQLGKYSAEGENEEAKKGMFVKGYTY----------
CA042215      SLLVRAKANSLAQLGKYSAEGESEEAKKGMFVQGYTY----------
At2g01140     ALLVRAKANSLAQLGKYSAEGENEDAKKGMFVKGYTY----------
ABK24286      ALLIRAKANSLAQLGRYSAEGESEESKKGMFVKGYTY----------
ABK25226      ALLIRAKANSLAQLGRYSAEGESEESKKGMFVKGYTY----------
ABK24568      ALLIRAKANSLAQLGRYSAEGESEESKKGMFVKGYTY----------
ACG47464      ALLVRAKANSLAQLGRYTGEGESDDAKKGMFQKGYTY----------
ACG47669      ALLVRAKANSLAQLGRYTGEGESDDAKKGMFQKGYTLMCQRDVSMT
Os01g0118000  ALLVRAKANSLAQLGRYTGEGESDEAKKGMFQKGYTY----------
              :**.************:*. ***.:::  ****  :***
```

| PP2C Transformed plants (Reference example 1) | Wild type (*Arabidopsis thaliana*) |

| PP2C&FBA1 Transformed plants (Example 1) | PP2C&FBA1 Transformed plants (Example 1) |

SEQUENCE LISTING

<160> NUMBER OF SEQ ID NOS: 64

<210> SEQ ID NO 1
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
    or preferably L or F
<220> FEATURE:

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K, R, Q or N
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

Xaa Xaa Gly Xaa Phe Asp Gly His Gly Xaa Xaa Gly Xaa Xaa Xaa Xaa
1               5                   10                  15

Xaa Xaa Val

<210> SEQ ID NO 2
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
<223> OTHER INFORMATION: Xaa can be any naturally occurring amino acid,
      or preferably V, L or I
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid,
      or preferably I, V, F, M or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid,
      or preferably G or A
<220> FEATURE:
<221> NAME/KEY: misc_feature
```

```
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably L, V or I
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I

<400> SEQUENCE: 2

Ser Gly Xaa Thr Xaa Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25

<210> SEQ ID NO 3
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably M, V or F
<220> FEATURE:
<221> NAME/KEY: misc_feature
<222> LOCATION: (5)..(5)
<223> OTHER INFORMATION: Xaa can be any naturally occurring amino acid,
      or preferably S, A or T
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
```

```
    or preferably F, I or V
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid,
      or preferably K or E
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid,
      or preferably D, N or H
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or F
```

```
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (38)..(38)
<223> OTHER INFORMATION: Xaa can be any naturally occurring amino acid,
      or preferably L or V
<220> FEATURE:
<221> NAME/KEY: misc_feature
<222> LOCATION: (40)..(40)
<223> OTHER INFORMATION: Xaa can be any naturally occurring amino acid,
      or preferably T or S
<220> FEATURE:
<221> NAME/KEY: misc_feature
<222> LOCATION: (43)..(43)
<223> OTHER INFORMATION: Xaa can be any naturally occurring amino acid,
      or preferably V, I or M
<220> FEATURE:
<221> NAME/KEY: misc_feature
<222> LOCATION: (44)..(44)
<223> OTHER INFORMATION: Xaa can be any naturally occurring amino acid,
      or preferably W or F
<220> FEATURE:
<221> NAME/KEY: misc_feature
<222> LOCATION: (45)..(45)
<223> OTHER INFORMATION: Xaa can be any naturally occurring amino acid,
      or preferably D or E
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid,
      or preferably L, I or M
<220> FEATURE:
<221> NAME/KEY: misc_feature
<222> LOCATION: (48)..(48)
<223> OTHER INFORMATION: Xaa can be any naturally occurring amino acid,
      or preferably S, T or P
<220> FEATURE:
<221> NAME/KEY: misc_feature
<222> LOCATION: (49)..(49)
<223> OTHER INFORMATION: Xaa can be any naturally occurring amino acid,
      or preferably N or S
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid,
      or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
      or preferably L, V, I or M
<220> FEATURE:
<221> NAME/KEY: misc_feature
<222> LOCATION: (56)..(56)
<223> OTHER INFORMATION: Xaa can be any naturally occurring amino acid,
      or preferably I or V

<400> SEQUENCE: 3
```

```
Gly Xaa Ala Xaa Xaa Arg Xaa Xaa Gly Asp Xaa Xaa Xaa Xaa Xaa
 1               5                  10                  15

Gly Xaa Xaa Xaa Xaa Pro Xaa Xaa Xaa Xaa Xaa Xaa Xaa Xaa Xaa
            20                  25                  30

Xaa Xaa Xaa Xaa Xaa Ala Xaa Asp Gly Xaa Xaa Xaa Xaa Xaa Xaa
            35                  40                  45

Xaa Xaa Xaa Xaa Xaa Xaa Xaa
            50                  55

<210> SEQ ID NO 4
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 4 atg gga cat ttc tct tcc atg ttc aac ggt ata gct aga tcc ttc tcg      48
Met Gly His Phe Ser Ser Met Phe Asn Gly Ile Ala Arg Ser Phe Ser
 1               5                  10                  15 atc aag aaa gcg aag aac atc aac agc agc aaa agc tac gct aag gaa      96
Ile Lys Lys Ala Lys Asn Ile Asn Ser Ser Lys Ser Tyr Ala Lys Glu
            20                  25                  30 gcc aca gat gaa atg gcg aga gag gcg aag aag aag gaa ctt att ttg     144
Ala Thr Asp Glu Met Ala Arg Glu Ala Lys Lys Lys Glu Leu Ile Leu
        35                  40                  45 aga tcc tct ggt tgc att aat gca gat gga tct aat aac ttg gct tct     192
Arg Ser Ser Gly Cys Ile Asn Ala Asp Gly Ser Asn Asn Leu Ala Ser
    50                  55                  60 gtt ttc tct aga cgc ggt gag aaa ggc gtt aat cag gac tgt gcc atc     240
Val Phe Ser Arg Arg Gly Glu Lys Gly Val Asn Gln Asp Cys Ala Ile
65                  70                  75                  80 gtc tgg gag gga tat ggg tgt caa gaa gac atg ata ttc tgt ggg ata     288
Val Trp Glu Gly Tyr Gly Cys Gln Glu Asp Met Ile Phe Cys Gly Ile
                85                  90                  95 ttc gat gga cat ggt ccc tgg gga cac ttt gtt tct aaa caa gtc aga     336
Phe Asp Gly His Gly Pro Trp Gly His Phe Val Ser Lys Gln Val Arg
            100                 105                 110 aac tca atg cct ata tct ttg ctc tgt aac tgg aaa gag act ctt tct     384
Asn Ser Met Pro Ile Ser Leu Leu Cys Asn Trp Lys Glu Thr Leu Ser
        115                 120                 125 cag acc aca ata gca gaa ccc gat aaa gag cta cag cgg ttt gca atc     432
Gln Thr Thr Ile Ala Glu Pro Asp Lys Glu Leu Gln Arg Phe Ala Ile
    130                 135                 140 tgg aaa tac tca ttc ctc aaa acc tgt gaa gct gtt gat ctg gag ctt     480
Trp Lys Tyr Ser Phe Leu Lys Thr Cys Glu Ala Val Asp Leu Glu Leu
145                 150                 155                 160 gag cat cac cga aag ata gat tct ttc aac agc ggt acg acc gct cta     528
Glu His His Arg Lys Ile Asp Ser Phe Asn Ser Gly Thr Thr Ala Leu
                165                 170                 175 acc att gtg aga cag ggt gat gtt att tat ata gca aac gtc ggg gat     576
Thr Ile Val Arg Gln Gly Asp Val Ile Tyr Ile Ala Asn Val Gly Asp
            180                 185                 190 tca cgt gcg gta ttg gcc aca gtt tca gac gaa gga agc ttg gtc gcg     624
Ser Arg Ala Val Leu Ala Thr Val Ser Asp Glu Gly Ser Leu Val Ala
        195                 200                 205 gtt cag ctc acc gta gat ttc aag cca aac ctg cct cag gag gaa gag     672
Val Gln Leu Thr Val Asp Phe Lys Pro Asn Leu Pro Gln Glu Glu Glu
    210                 215                 220
```

```
cgg ata atc gga tgc aac ggg aga gta ttt tgc ctt caa gat gag cca    720
Arg Ile Ile Gly Cys Asn Gly Arg Val Phe Cys Leu Gln Asp Glu Pro
225                 230                 235                 240 ggg gtc cac cgt gta tgg caa cca gta gat gaa tct ccg ggg ctc gca    768
Gly Val His Arg Val Trp Gln Pro Val Asp Glu Ser Pro Gly Leu Ala
            245                 250                 255 atg tca aga gca ttc gga gac tat tgt atc aaa gat tac gga ttg gtc    816
Met Ser Arg Ala Phe Gly Asp Tyr Cys Ile Lys Asp Tyr Gly Leu Val
        260                 265                 270 tca gtg cct gaa gtc act cag agg cat ata tcc att aga gac cag ttt    864
Ser Val Pro Glu Val Thr Gln Arg His Ile Ser Ile Arg Asp Gln Phe
    275                 280                 285 ata atc ttg gcc act gat ggg gta tgg gat gtg ata tca aac caa gag    912
Ile Ile Leu Ala Thr Asp Gly Val Trp Asp Val Ile Ser Asn Gln Glu
290                 295                 300 gcc ata gat att gtt tcc tcg acg gcg gag cgg gca aaa gct gcc aag    960
Ala Ile Asp Ile Val Ser Ser Thr Ala Glu Arg Ala Lys Ala Ala Lys
305                 310                 315                 320 cga ctg gta cag caa gca gtt agg gct tgg aat aga aag aga cgc gga   1008
Arg Leu Val Gln Gln Ala Val Arg Ala Trp Asn Arg Lys Arg Arg Gly
            325                 330                 335 atc gcc atg gat gat atc tct gcc gtg tgc ctc ttc ttc cat tct tca   1056
Ile Ala Met Asp Asp Ile Ser Ala Val Cys Leu Phe Phe His Ser Ser
        340                 345                 350 tcg tcg tcg cca tct cta tag                                        1077
Ser Ser Ser Pro Ser Leu
    355

<210> SEQ ID NO 5
<211> LENGTH: 358
<212> TYPE: PRT
<213> ORGANISM: Arabidopsis thaliana

<400> SEQUENCE: 5

Met Gly His Phe Ser Ser Met Phe Asn Gly Ile Ala Arg Ser Phe Ser
1               5                   10                  15

Ile Lys Lys Ala Lys Asn Ile Asn Ser Ser Lys Ser Tyr Ala Lys Glu
            20                  25                  30

Ala Thr Asp Glu Met Ala Arg Glu Ala Lys Lys Lys Glu Leu Ile Leu
        35                  40                  45

Arg Ser Ser Gly Cys Ile Asn Ala Asp Gly Ser Asn Asn Leu Ala Ser
    50                  55                  60

Val Phe Ser Arg Arg Gly Glu Lys Gly Val Asn Gln Asp Cys Ala Ile
65                  70                  75                  80

Val Trp Glu Gly Tyr Gly Cys Gln Glu Asp Met Ile Phe Cys Gly Ile
                85                  90                  95

Phe Asp Gly His Gly Pro Trp Gly His Phe Val Ser Lys Gln Val Arg
            100                 105                 110

Asn Ser Met Pro Ile Ser Leu Leu Cys Asn Trp Lys Glu Thr Leu Ser
        115                 120                 125

Gln Thr Thr Ile Ala Glu Pro Asp Lys Glu Leu Gln Arg Phe Ala Ile
    130                 135                 140

Trp Lys Tyr Ser Phe Leu Lys Thr Cys Glu Ala Val Asp Leu Glu Leu
145                 150                 155                 160

Glu His His Arg Lys Ile Asp Ser Phe Asn Ser Gly Thr Thr Ala Leu
                165                 170                 175

Thr Ile Val Arg Gln Gly Asp Val Ile Tyr Ile Ala Asn Val Gly Asp
            180                 185                 190
```

```
Ser Arg Ala Val Leu Ala Thr Val Ser Asp Glu Gly Ser Leu Val Ala
        195                 200                 205

Val Gln Leu Thr Val Asp Phe Lys Pro Asn Leu Pro Gln Glu Glu Glu
    210                 215                 220

Arg Ile Ile Gly Cys Asn Gly Arg Val Phe Cys Leu Gln Asp Glu Pro
225                 230                 235                 240

Gly Val His Arg Val Trp Gln Pro Val Asp Glu Ser Pro Gly Leu Ala
                245                 250                 255

Met Ser Arg Ala Phe Gly Asp Tyr Cys Ile Lys Asp Tyr Gly Leu Val
            260                 265                 270

Ser Val Pro Glu Val Thr Gln Arg His Ile Ser Ile Arg Asp Gln Phe
        275                 280                 285

Ile Ile Leu Ala Thr Asp Gly Val Trp Asp Val Ile Ser Asn Gln Glu
    290                 295                 300

Ala Ile Asp Ile Val Ser Ser Thr Ala Glu Arg Ala Lys Ala Ala Lys
305                 310                 315                 320

Arg Leu Val Gln Gln Ala Val Arg Ala Trp Asn Arg Lys Arg Arg Gly
                325                 330                 335

Ile Ala Met Asp Asp Ile Ser Ala Val Cys Leu Phe Phe His Ser Ser
            340                 345                 350

Ser Ser Ser Pro Ser Leu
        355

<210> SEQ ID NO 6
<211> LENGTH: 1176
<212> TYPE: DNA
<213> ORGANISM: Oryza sativa
<220> FEATURE:
<221> NAME/KEY: CDS
<222> LOCATION: (1)..(1176)

<400> SEQUENCE: 6 atg cgg cac atc tcg tcg ctg ctg cag ggg ctg gcg cgc tcg ctg tcg      48
Met Arg His Ile Ser Ser Leu Leu Gln Gly Leu Ala Arg Ser Leu Ser
1               5                   10                  15 gtg ggg aag gag agg aag ggc ggc gac ggc gac gac ggg aag gcg gcg      96
Val Gly Lys Glu Arg Lys Gly Gly Asp Gly Asp Asp Gly Lys Ala Ala
            20                  25                  30 gcg gcg acg gcg acg gcg gtg ctg agg aca tcg ggg acg ctg tgg ggc     144
Ala Ala Thr Ala Thr Ala Val Leu Arg Thr Ser Gly Thr Leu Trp Gly
        35                  40                  45 gag ggc tct gag acg ttc gcc gcc gtc tgc tcc cgc cgc ggc gag aag     192
Glu Gly Ser Glu Thr Phe Ala Ala Val Cys Ser Arg Arg Gly Glu Lys
    50                  55                  60 ggc atc aac cag gac tgc tcc atc gtc tgc gag gga ttc ggg tgc gag     240
Gly Ile Asn Gln Asp Cys Ser Ile Val Cys Glu Gly Phe Gly Cys Glu
65                  70                  75                  80 gag ggg agc gtg ttg tgc ggc atc ttc gac ggg cac ggg cag tgg ggc     288
Glu Gly Ser Val Leu Cys Gly Ile Phe Asp Gly His Gly Gln Trp Gly
                85                  90                  95 cac tac gtg gcg aag gcg gtg agg gag tcg ctg ccg ccg gcg ctg ctc     336
His Tyr Val Ala Lys Ala Val Arg Glu Ser Leu Pro Pro Ala Leu Leu
            100                 105                 110 cgg cgg tgg cgg gag gcc gtg acg ctg gcg gcg ctc atc gac ggc ggc     384
Arg Arg Trp Arg Glu Ala Val Thr Leu Ala Ala Leu Ile Asp Gly Gly
        115                 120                 125 gag aag cgg ctc tgc gag tgc cgg ccc gac ctg tgg cgc cag tcc tac     432
Glu Lys Arg Leu Cys Glu Cys Arg Pro Asp Leu Trp Arg Gln Ser Tyr
```

```
ctg gcc gcc tgc gcc gcc gtc gac gcc gag ctc cgc gcc agc cgc cgc        480
Leu Ala Ala Cys Ala Ala Val Asp Ala Glu Leu Arg Ala Ser Arg Arg
145                 150                 155                 160 ctc gac gcc gtc cac agc ggc tgc acc gcg ctg tcc ctc gtc aag cac        528
Leu Asp Ala Val His Ser Gly Cys Thr Ala Leu Ser Leu Val Lys His
                165                 170                 175 ggc gac ctc ctc gtc gtc gcc aac gtc ggc gac tcg cgc gcc gtc ctg        576
Gly Asp Leu Leu Val Val Ala Asn Val Gly Asp Ser Arg Ala Val Leu
            180                 185                 190 gcc acc gcc tcc ccc gac gac ggt ggc ggc gcc cgc ctc gcc gcc gtg        624
Ala Thr Ala Ser Pro Asp Asp Gly Gly Gly Ala Arg Leu Ala Ala Val
        195                 200                 205 cag ctc acc gtc gac ttc aag ccc aac ctg ccc cag gag agg gag agg        672
Gln Leu Thr Val Asp Phe Lys Pro Asn Leu Pro Gln Glu Arg Glu Arg
    210                 215                 220 atc atg gag tgc aac ggg agg gtg cag tgc ctc gcc gac gag ccc ggg        720
Ile Met Glu Cys Asn Gly Arg Val Gln Cys Leu Ala Asp Glu Pro Gly
225                 230                 235                 240 gtg cac cgg gtg tgg cgg ccg gac agg gag ggc cca ggc ctc gcc atg        768
Val His Arg Val Trp Arg Pro Asp Arg Glu Gly Pro Gly Leu Ala Met
                245                 250                 255 tcg cgc gcc ttc ggc gac tac tgc gtc aag gat tac ggc gtc atc tcg        816
Ser Arg Ala Phe Gly Asp Tyr Cys Val Lys Asp Tyr Gly Val Ile Ser
                260                 265                 270 gcg ccg gag gtg acg cac cgc cgg atc acc gcc cag gac cac ttc gtc        864
Ala Pro Glu Val Thr His Arg Arg Ile Thr Ala Gln Asp His Phe Val
        275                 280                 285 atc ctc gcc acc gac ggg gac aaa cat ctc aac ttg ttc gtc ttc gtc        912
Ile Leu Ala Thr Asp Gly Asp Lys His Leu Asn Leu Phe Val Phe Val
    290                 295                 300 tgc gcg gca ggt gtg gga cgt ggt gtc gaa cga gga ggc ggt gca gat        960
Cys Ala Ala Gly Val Gly Arg Gly Val Glu Arg Gly Gly Gly Ala Asp
305                 310                 315                 320 cgt ggc gtc ggc gcc gga gag gga gaa ggc ggc gaa gcg gct cgt cga       1008
Arg Gly Val Gly Ala Gly Glu Gly Glu Gly Gly Glu Ala Ala Arg Arg
                325                 330                 335 gtt cgc cgt ccg ggc atg gag gcg caa gcg ccg ggg cat cgc cgt cga       1056
Val Arg Arg Pro Gly Met Glu Ala Gln Ala Pro Gly His Arg Arg Arg
                340                 345                 350 cga ctc ctc ggc gat ctg cct ctt ctt cca ctc gcc gcc gtc cta aac       1104
Arg Leu Leu Gly Asp Leu Pro Leu Leu Pro Leu Ala Ala Val Leu Asn
        355                 360                 365 aac aca cac gct gac acg cac gca gcc aac aaa aac cgc aca cgc cga       1152
Asn Thr His Ala Asp Thr His Ala Ala Asn Lys Asn Arg Thr Arg Arg
    370                 375                 380 cga caa tgt cgc cgt cgt cgt tga                                       1176
Arg Gln Cys Arg Arg Arg Arg
385                 390

<210> SEQ ID NO 7
<211> LENGTH: 391
<212> TYPE: PRT
<213> ORGANISM: Oryza sativa

<400> SEQUENCE: 7

Met Arg His Ile Ser Ser Leu Leu Gln Gly Leu Ala Arg Ser Leu Ser
1               5                   10                  15

Val Gly Lys Glu Arg Lys Gly Gly Asp Gly Asp Asp Gly Lys Ala Ala
            20                  25                  30
```

Ala Ala Thr Ala Thr Ala Val Leu Arg Thr Ser Gly Thr Leu Trp Gly
         35                  40                  45

Glu Gly Ser Glu Thr Phe Ala Val Cys Ser Arg Arg Gly Glu Lys
 50                  55                  60

Gly Ile Asn Gln Asp Cys Ser Ile Val Cys Glu Gly Phe Gly Cys Glu
 65                  70                  75                  80

Glu Gly Ser Val Leu Cys Gly Ile Phe Asp Gly His Gly Gln Trp Gly
                 85                  90                  95

His Tyr Val Ala Lys Ala Val Arg Glu Ser Leu Pro Pro Ala Leu Leu
                100                 105                 110

Arg Arg Trp Arg Glu Ala Val Thr Leu Ala Ala Leu Ile Asp Gly Gly
            115                 120                 125

Glu Lys Arg Leu Cys Glu Cys Arg Pro Asp Leu Trp Arg Gln Ser Tyr
            130                 135                 140

Leu Ala Ala Cys Ala Ala Val Asp Ala Glu Leu Arg Ala Ser Arg Arg
145                 150                 155                 160

Leu Asp Ala Val His Ser Gly Cys Thr Ala Leu Ser Leu Val Lys His
                165                 170                 175

Gly Asp Leu Leu Val Ala Asn Val Gly Asp Ser Arg Ala Val Leu
                180                 185                 190

Ala Thr Ala Ser Pro Asp Asp Gly Gly Ala Arg Leu Ala Ala Val
            195                 200                 205

Gln Leu Thr Val Asp Phe Lys Pro Asn Leu Pro Gln Glu Arg Glu Arg
            210                 215                 220

Ile Met Glu Cys Asn Gly Arg Val Gln Cys Leu Ala Asp Glu Pro Gly
225                 230                 235                 240

Val His Arg Val Trp Arg Pro Asp Arg Glu Gly Pro Gly Leu Ala Met
                245                 250                 255

Ser Arg Ala Phe Gly Asp Tyr Cys Val Lys Asp Tyr Gly Val Ile Ser
                260                 265                 270

Ala Pro Glu Val Thr His Arg Ile Thr Ala Gln Asp His Phe Val
            275                 280                 285

Ile Leu Ala Thr Asp Gly Asp Lys His Leu Asn Leu Phe Val Phe Val
            290                 295                 300

Cys Ala Ala Gly Val Gly Arg Gly Val Glu Arg Gly Gly Gly Ala Asp
305                 310                 315                 320

Arg Gly Val Gly Ala Gly Glu Gly Glu Gly Glu Ala Ala Arg Arg
                325                 330                 335

Val Arg Arg Pro Gly Met Glu Ala Gln Ala Pro Gly His Arg Arg Arg
            340                 345                 350

Arg Leu Leu Gly Asp Leu Pro Leu Leu Pro Leu Ala Ala Val Leu Asn
            355                 360                 365

Asn Thr His Ala Asp Thr His Ala Ala Asn Lys Asn Arg Thr Arg Arg
            370                 375                 380

Arg Gln Cys Arg Arg Arg Arg
385                 390

<210> SEQ ID NO 8
<211> LENGTH: 1263
<212> TYPE: DNA
<213> ORGANISM: Oryza sativa
<220> FEATURE:
<221> NAME/KEY: CDS
<222> LOCATION: (1)..(1263)

<400> SEQUENCE: 8

```
atg ggg ata tgc tgc agc aag ggg aag gag gag ctt gag gag gag gga     48
Met Gly Ile Cys Cys Ser Lys Gly Lys Glu Glu Leu Glu Glu Glu Gly
1               5                   10                  15 ttt cca tgg aag cac gac gcc ttc ttc cac gac cag ctt tgg agc gct     96
Phe Pro Trp Lys His Asp Ala Phe Phe His Asp Gln Leu Trp Ser Ala
            20                  25                  30 ggc gtc tcc atg cac acc aag caa ggc tgg aag ggc gcc aac cag gac    144
Gly Val Ser Met His Thr Lys Gln Gly Trp Lys Gly Ala Asn Gln Asp
        35                  40                  45 gcc atg act acc tgc cag gac ttt gcg ggg cac aag ggc cag ata ttt    192
Ala Met Thr Thr Cys Gln Asp Phe Ala Gly His Lys Gly Gln Ile Phe
    50                  55                  60 tgt gga gtt ttt gat ggg cat ggc cct ctc gga agg gaa gtt gct cgc    240
Cys Gly Val Phe Asp Gly His Gly Pro Leu Gly Arg Glu Val Ala Arg
65                  70                  75                  80 cat gtc cgc gac gtc ctt cca gtg aaa cta tcc tcc tct ttg gca ctg    288
His Val Arg Asp Val Leu Pro Val Lys Leu Ser Ser Ser Leu Ala Leu
                85                  90                  95 aag act gaa caa gat cca tcc agc aac aca gat aag gaa acc ttg gaa    336
Lys Thr Glu Gln Asp Pro Ser Ser Asn Thr Asp Lys Glu Thr Leu Glu
            100                 105                 110 aag tca gat tgc acc tca ttg agc gat aca agc aat gag aag caa ttg    384
Lys Ser Asp Cys Thr Ser Leu Ser Asp Thr Ser Asn Glu Lys Gln Leu
        115                 120                 125 tta tcc acc tgg aag aac ata ttt gtc aag aca ttt gag gat gtt gat    432
Leu Ser Thr Trp Lys Asn Ile Phe Val Lys Thr Phe Glu Asp Val Asp
    130                 135                 140 gag gat ctg agg caa cat tct gga att gac tgc att tgt agt ggc aca    480
Glu Asp Leu Arg Gln His Ser Gly Ile Asp Cys Ile Cys Ser Gly Thr
145                 150                 155                 160 act gct gtc act gtc gtt agg cag ggt gat cac ctg atc att gca aat    528
Thr Ala Val Thr Val Val Arg Gln Gly Asp His Leu Ile Ile Ala Asn
                165                 170                 175 ttg ggc gat tca cgt gcg gtt ctt tgc acc cga gac agc aag gac cgc    576
Leu Gly Asp Ser Arg Ala Val Leu Cys Thr Arg Asp Ser Lys Asp Arg
            180                 185                 190 cca att tca gtc caa cta acc act gac ctg aaa cca aat ctt cca agc    624
Pro Ile Ser Val Gln Leu Thr Thr Asp Leu Lys Pro Asn Leu Pro Ser
        195                 200                 205 gaa gct gag aga atc ctg aat tcc aag ggg cgg gtt ttc gcc atg gac    672
Glu Ala Glu Arg Ile Leu Asn Ser Lys Gly Arg Val Phe Ala Met Asp
    210                 215                 220 gat gag ccg gac gtg cct agg atg tgg cta cca gac caa gac gcg ccg    720
Asp Glu Pro Asp Val Pro Arg Met Trp Leu Pro Asp Gln Asp Ala Pro
225                 230                 235                 240 ggc ctc gcc atg gca agg gca ttt gga gat ttc tgc ttg aag agt cat    768
Gly Leu Ala Met Ala Arg Ala Phe Gly Asp Phe Cys Leu Lys Ser His
                245                 250                 255 gga cta atc tgt aca cca gaa gtc tac tac agg aag cta tct gca aaa    816
Gly Leu Ile Cys Thr Pro Glu Val Tyr Tyr Arg Lys Leu Ser Ala Lys
            260                 265                 270 gat gac ttc ttg gta ctt gct act gac ggg ata tgg gac gtg ctg tcg    864
Asp Asp Phe Leu Val Leu Ala Thr Asp Gly Ile Trp Asp Val Leu Ser
        275                 280                 285 aac aag gag gtg atc aag atc gta tcg tcg gct act gac cat tcc aag    912
Asn Lys Glu Val Ile Lys Ile Val Ser Ser Ala Thr Asp His Ser Lys
    290                 295                 300 gcc gcc aag cag ctc gtc gag cgg gcg gtg cgc acg tgg cgg cgc aag    960
```

```
Ala Ala Lys Gln Leu Val Glu Arg Ala Val Arg Thr Trp Arg Arg Lys
305                 310                 315                 320 ttc ccg acg tcg atg gtc gac gac tgc gcc gtg gtg tgc ctc ttc ttg    1008
Phe Pro Thr Ser Met Val Asp Asp Cys Ala Val Val Cys Leu Phe Leu
                325                 330                 335 aag cct tca ccg tcg tcg tcg gag agc acc ccc ggg gac gcg aaa cct    1056
Lys Pro Ser Pro Ser Ser Ser Glu Ser Thr Pro Gly Asp Ala Lys Pro
                340                 345                 350 cct cag gcc gtg tcg ttc acg ggc agc ttc cga aag gtc ctg ggc ggc    1104
Pro Gln Ala Val Ser Phe Thr Gly Ser Phe Arg Lys Val Leu Gly Gly
                355                 360                 365 ggc ggc ggc gag gcg gag gag ggg acg aat gta tgg aga gct ctg gag    1152
Gly Gly Gly Glu Ala Glu Glu Gly Thr Asn Val Trp Arg Ala Leu Glu
370                 375                 380 ggg gtg gct cgg gtg aac tcg gtg gtg agg ctg ccg cgg atg ggc gcc    1200
Gly Val Ala Arg Val Asn Ser Val Val Arg Leu Pro Arg Met Gly Ala
385                 390                 395                 400 gtg ctg agc tgg cgg cgg cgg tcg acg tcg ctg gag gaa gac gac gag    1248
Val Leu Ser Trp Arg Arg Arg Ser Thr Ser Leu Glu Glu Asp Asp Glu
                405                 410                 415 gcg agg att gat tga                                                1263
Ala Arg Ile Asp
                420

<210> SEQ ID NO 9
<211> LENGTH: 420
<212> TYPE: PRT
<213> ORGANISM: Oryza sativa

<400> SEQUENCE: 9

Met Gly Ile Cys Cys Ser Lys Gly Lys Glu Glu Leu Glu Glu Glu Gly
1               5                   10                  15

Phe Pro Trp Lys His Asp Ala Phe Phe His Asp Gln Leu Trp Ser Ala
                20                  25                  30

Gly Val Ser Met His Thr Lys Gln Gly Trp Lys Gly Ala Asn Gln Asp
            35                  40                  45

Ala Met Thr Thr Cys Gln Asp Phe Ala Gly His Lys Gly Gln Ile Phe
        50                  55                  60

Cys Gly Val Phe Asp Gly His Gly Pro Leu Gly Arg Glu Val Ala Arg
65              70                  75                  80

His Val Arg Asp Val Leu Pro Val Lys Leu Ser Ser Ser Leu Ala Leu
                85                  90                  95

Lys Thr Glu Gln Asp Pro Ser Ser Asn Thr Asp Lys Glu Thr Leu Glu
            100                 105                 110

Lys Ser Asp Cys Thr Ser Leu Ser Asp Thr Ser Asn Glu Lys Gln Leu
        115                 120                 125

Leu Ser Thr Trp Lys Asn Ile Phe Val Lys Thr Phe Glu Asp Val Asp
130                 135                 140

Glu Asp Leu Arg Gln His Ser Gly Ile Asp Cys Ile Cys Ser Gly Thr
145                 150                 155                 160

Thr Ala Val Thr Val Val Arg Gln Gly Asp His Leu Ile Ile Ala Asn
                165                 170                 175

Leu Gly Asp Ser Arg Ala Val Leu Cys Thr Arg Asp Ser Lys Asp Arg
            180                 185                 190

Pro Ile Ser Val Gln Leu Thr Thr Asp Leu Lys Pro Asn Leu Pro Ser
        195                 200                 205

Glu Ala Glu Arg Ile Leu Asn Ser Lys Gly Arg Val Phe Ala Met Asp
```

```
                 210                 215                 220
Asp Glu Pro Asp Val Pro Arg Met Trp Leu Pro Asp Gln Asp Ala Pro
225                 230                 235                 240

Gly Leu Ala Met Ala Arg Ala Phe Gly Asp Phe Cys Leu Lys Ser His
                245                 250                 255

Gly Leu Ile Cys Thr Pro Glu Val Tyr Tyr Arg Lys Leu Ser Ala Lys
            260                 265                 270

Asp Asp Phe Leu Val Leu Ala Thr Asp Gly Ile Trp Asp Val Leu Ser
        275                 280                 285

Asn Lys Glu Val Ile Lys Ile Val Ser Ser Ala Thr Asp His Ser Lys
    290                 295                 300

Ala Ala Lys Gln Leu Val Glu Arg Ala Val Thr Trp Arg Arg Lys
305                 310                 315                 320

Phe Pro Thr Ser Met Val Asp Asp Cys Ala Val Val Cys Leu Phe Leu
                325                 330                 335

Lys Pro Ser Pro Ser Ser Ser Glu Ser Thr Pro Gly Asp Ala Lys Pro
                340                 345                 350

Pro Gln Ala Val Ser Phe Thr Gly Ser Phe Arg Lys Val Leu Gly Gly
            355                 360                 365

Gly Gly Gly Glu Ala Glu Gly Thr Asn Val Trp Arg Ala Leu Glu
        370                 375                 380

Gly Val Ala Arg Val Asn Ser Val Val Arg Leu Pro Arg Met Gly Ala
385                 390                 395                 400

Val Leu Ser Trp Arg Arg Arg Ser Thr Ser Leu Glu Glu Asp Asp Glu
                405                 410                 415

Ala Arg Ile Asp
            420

<210> SEQ ID NO 10
<211> LENGTH: 1632
<212> TYPE: DNA
<213> ORGANISM: Oryza sativa
<220> FEATURE:
<221> NAME/KEY: CDS
<222> LOCATION: (1)..(1632)

<400> SEQUENCE: 10 atg gat ggg gtg cct gat gcc caa cgc aca aca tca cca tca atg ata      48
Met Asp Gly Val Pro Asp Ala Gln Arg Thr Thr Ser Pro Ser Met Ile
1               5                   10                  15 aaa caa caa aac tac ttc aac tac ccc tac gca ttc aac tcc att cta      96
Lys Gln Gln Asn Tyr Phe Asn Tyr Pro Tyr Ala Phe Asn Ser Ile Leu
                20                  25                  30 ctc tct acc ccc tcc ttc ctt cct tcc ttc ctt cct agc tac ctc tac     144
Leu Ser Thr Pro Ser Phe Leu Pro Ser Phe Leu Pro Ser Tyr Leu Tyr
            35                  40                  45 gaa gta cca gca gca gaa gaa gca atg ggg atc tgc tgc agc aag ggg     192
Glu Val Pro Ala Ala Glu Glu Ala Met Gly Ile Cys Cys Ser Lys Gly
        50                  55                  60 aag gag gag ctt gag gag gga ttt cca tgg aag cac gac gcc ttc ttc     240
Lys Glu Glu Leu Glu Glu Gly Phe Pro Trp Lys His Asp Ala Phe Phe
65                  70                  75                  80 cac gac cag ctt tgg agc gct ggc gtc tcc atg cac acc aag caa ggc     288
His Asp Gln Leu Trp Ser Ala Gly Val Ser Met His Thr Lys Gln Gly
                85                  90                  95 tgg aag ggc gct aac cag gat gcc atg act acc tgc cag gac ttt gcg     336
Trp Lys Gly Ala Asn Gln Asp Ala Met Thr Thr Cys Gln Asp Phe Ala
            100                 105                 110
```

| | | |
|---|---|---|
| ggg cac aag ggc cag ata ttt tgt gga gtt ttt gat ggg cat ggc cct<br>Gly His Lys Gly Gln Ile Phe Cys Gly Val Phe Asp Gly His Gly Pro<br>     115                   120                   125 | 384 |
| ctc gga agg gaa gtt gct cgc cat gtc cgc gac gtc ctt cca atg aaa<br>Leu Gly Arg Glu Val Ala Arg His Val Arg Asp Val Leu Pro Met Lys<br>130                   135                   140 | 432 |
| cta tcc tcc tct ttg gca ctg aaa act gaa caa gat cca tcc agc aac<br>Leu Ser Ser Ser Leu Ala Leu Lys Thr Glu Gln Asp Pro Ser Ser Asn<br>145                   150                   155                   160 | 480 |
| aca gat aag gaa gcc ttg gaa aaa tca gat tgc acc tca ttg agc gat<br>Thr Asp Lys Glu Ala Leu Glu Lys Ser Asp Cys Thr Ser Leu Ser Asp<br>                 165                   170                   175 | 528 |
| aca agc aat gag aag caa ttg tta tcc acc tgg aag aac ata ttt gtc<br>Thr Ser Asn Glu Lys Gln Leu Leu Ser Thr Trp Lys Asn Ile Phe Val<br>                 180                   185                   190 | 576 |
| aag aca ttt gag gat gta gat gat gat ctg aga caa aat tct gga att<br>Lys Thr Phe Glu Asp Val Asp Asp Asp Leu Arg Gln Asn Ser Gly Ile<br>                 195                   200                   205 | 624 |
| gac tgc att tgt agt ggc aca act gct gtc act gtc gtc agg cag ggt<br>Asp Cys Ile Cys Ser Gly Thr Thr Ala Val Thr Val Val Arg Gln Gly<br>210                   215                   220 | 672 |
| gat cac ctg atc att gca aat ttg ggc gat tca cgt gcg gtt ctt tgc<br>Asp His Leu Ile Ile Ala Asn Leu Gly Asp Ser Arg Ala Val Leu Cys<br>225                   230                   235                   240 | 720 |
| acc cga gat agc aag gac cgc cca att cca gtt caa cta acc act gac<br>Thr Arg Asp Ser Lys Asp Arg Pro Ile Pro Val Gln Leu Thr Thr Asp<br>                 245                   250                   255 | 768 |
| ctg aaa cca aat ctt cca agc gaa gct gag aga atc ctg aat tgt aag<br>Leu Lys Pro Asn Leu Pro Ser Glu Ala Glu Arg Ile Leu Asn Cys Lys<br>                 260                   265                   270 | 816 |
| ggg cgg gtt ttt gcc atg gac gac gag ccg gac gtg tct agg atg tgg<br>Gly Arg Val Phe Ala Met Asp Asp Glu Pro Asp Val Ser Arg Met Trp<br>                 275                   280                   285 | 864 |
| cta cca gac caa gac gcg ccg ggc ctc gcc atg gca agg gca ttt gga<br>Leu Pro Asp Gln Asp Ala Pro Gly Leu Ala Met Ala Arg Ala Phe Gly<br>290                   295                   300 | 912 |
| gat ttc tgc ttg aag agt cat gga ctt atc tgt aca cca gaa gtc tat<br>Asp Phe Cys Leu Lys Ser His Gly Leu Ile Cys Thr Pro Glu Val Tyr<br>305                   310                   315                   320 | 960 |
| tac agg aag cta tcc gaa aaa gat gaa ttc ttg gta ctt gct act gac<br>Tyr Arg Lys Leu Ser Glu Lys Asp Glu Phe Leu Val Leu Ala Thr Asp<br>                 325                   330                   335 | 1008 |
| ggg ata tgg gac gtg cta tcg aac aag gaa gtg atc aag atc gta tcg<br>Gly Ile Trp Asp Val Leu Ser Asn Lys Glu Val Ile Lys Ile Val Ser<br>                 340                   345                   350 | 1056 |
| tcg gct act gac cat tcc aag gcc gcc aag cag ctg gtc gag cgg gcg<br>Ser Ala Thr Asp His Ser Lys Ala Ala Lys Gln Leu Val Glu Arg Ala<br>                 355                   360                   365 | 1104 |
| gtg cgc gcg tgg cgg cgc aag ttc ccg acg tca atg gtc gac gac tgc<br>Val Arg Ala Trp Arg Arg Lys Phe Pro Thr Ser Met Val Asp Asp Cys<br>370                   375                   380 | 1152 |
| gcc gtc gtc tgc ctc ttc ttg aag cct tct ccg tcg tcg gag gag agc<br>Ala Val Val Cys Leu Phe Leu Lys Pro Ser Pro Ser Ser Glu Glu Ser<br>385                   390                   395                   400 | 1200 |
| acc cat gta gac gcg aag gcg cct cag gtc gtg tcg ttc acg ggc agc<br>Thr His Val Asp Ala Lys Ala Pro Gln Val Val Ser Phe Thr Gly Ser<br>                 405                   410                   415 | 1248 |
| ttc cgc aag gcc ctg ggt ggt ggc ggc ggc gag gcg gag gag gtg<br>Phe Arg Lys Ala Leu Gly Gly Gly Gly Gly Glu Ala Glu Glu Val | 1296 |

```
                       420                 425                 430
gaa aag att tat cga cga agt atc cgc act gtc aca cgg gac att tgg      1344
Glu Lys Ile Tyr Arg Arg Ser Ile Arg Thr Val Thr Arg Asp Ile Trp
        435                 440                 445 gac aaa gta tct gca aga ctc gac tgt gat cac ata tcc acg acg cac      1392
Asp Lys Val Ser Ala Arg Leu Asp Cys Asp His Ile Ser Thr Thr His
450                 455                 460 aac cca gat gaa acg ctg ctt gat tgg tgg gaa aga aga aca gag caa      1440
Asn Pro Asp Glu Thr Leu Leu Asp Trp Trp Glu Arg Arg Thr Glu Gln
465                 470                 475                 480 aat gac aag gac aag acg aag gga acg cgc tcc att cac atg ctc ctt      1488
Asn Asp Lys Asp Lys Thr Lys Gly Thr Arg Ser Ile His Met Leu Leu
            485                 490                 495 agc tgg gaa atc tgg tgt gaa agg aat agg cgc gtt ttc agg aat aag      1536
Ser Trp Glu Ile Trp Cys Glu Arg Asn Arg Arg Val Phe Arg Asn Lys
        500                 505                 510 gag ctc gct atc tca caa ttg gtg acc aaa atc ctt gat gaa atc aat      1584
Glu Leu Ala Ile Ser Gln Leu Val Thr Lys Ile Leu Asp Glu Ile Asn
    515                 520                 525 gtc tgg att gca tgc ggg gcg aag aat tta gcg aga ata gtg ttg taa      1632
Val Trp Ile Ala Cys Gly Ala Lys Asn Leu Ala Arg Ile Val Leu
530                 535                 540

<210> SEQ ID NO 11
<211> LENGTH: 543
<212> TYPE: PRT
<213> ORGANISM: Oryza sativa

<400> SEQUENCE: 11

Met Asp Gly Val Pro Asp Ala Gln Arg Thr Thr Ser Pro Ser Met Ile
1               5                   10                  15

Lys Gln Gln Asn Tyr Phe Asn Tyr Pro Tyr Ala Phe Asn Ser Ile Leu
            20                  25                  30

Leu Ser Thr Pro Ser Phe Leu Pro Ser Phe Leu Pro Ser Tyr Leu Tyr
        35                  40                  45

Glu Val Pro Ala Ala Glu Glu Ala Met Gly Ile Cys Cys Ser Lys Gly
    50                  55                  60

Lys Glu Glu Leu Glu Glu Gly Phe Pro Trp Lys His Asp Ala Phe Phe
65                  70                  75                  80

His Asp Gln Leu Trp Ser Ala Gly Val Ser Met His Thr Lys Gln Gly
                85                  90                  95

Trp Lys Gly Ala Asn Gln Asp Ala Met Thr Thr Cys Gln Asp Phe Ala
            100                 105                 110

Gly His Lys Gly Gln Ile Phe Cys Gly Val Phe Asp Gly His Gly Pro
        115                 120                 125

Leu Gly Arg Glu Val Ala Arg His Val Arg Asp Val Leu Pro Met Lys
    130                 135                 140

Leu Ser Ser Ser Leu Ala Leu Lys Thr Glu Gln Asp Pro Ser Ser Asn
145                 150                 155                 160

Thr Asp Lys Glu Ala Leu Glu Lys Ser Asp Cys Thr Ser Leu Ser Asp
                165                 170                 175

Thr Ser Asn Glu Lys Gln Leu Leu Ser Thr Trp Lys Asn Ile Phe Val
            180                 185                 190

Lys Thr Phe Glu Asp Val Asp Asp Leu Arg Gln Asn Ser Gly Ile
        195                 200                 205

Asp Cys Ile Cys Ser Gly Thr Thr Ala Val Thr Val Val Arg Gln Gly
    210                 215                 220
```

```
Asp His Leu Ile Ile Ala Asn Leu Gly Asp Ser Arg Ala Val Leu Cys
225                 230                 235                 240

Thr Arg Asp Ser Lys Asp Arg Pro Ile Pro Val Gln Leu Thr Thr Asp
            245                 250                 255

Leu Lys Pro Asn Leu Pro Ser Glu Ala Glu Arg Ile Leu Asn Cys Lys
        260                 265                 270

Gly Arg Val Phe Ala Met Asp Asp Glu Pro Asp Val Ser Arg Met Trp
    275                 280                 285

Leu Pro Asp Gln Asp Ala Pro Gly Leu Ala Met Ala Arg Ala Phe Gly
290                 295                 300

Asp Phe Cys Leu Lys Ser His Gly Leu Ile Cys Thr Pro Glu Val Tyr
305                 310                 315                 320

Tyr Arg Lys Leu Ser Glu Lys Asp Glu Phe Leu Val Leu Ala Thr Asp
            325                 330                 335

Gly Ile Trp Asp Val Leu Ser Asn Lys Glu Val Ile Lys Ile Val Ser
        340                 345                 350

Ser Ala Thr Asp His Ser Lys Ala Ala Lys Gln Leu Val Glu Arg Ala
    355                 360                 365

Val Arg Ala Trp Arg Arg Lys Phe Pro Thr Ser Met Val Asp Asp Cys
370                 375                 380

Ala Val Val Cys Leu Phe Leu Lys Pro Ser Pro Ser Ser Glu Glu Ser
385                 390                 395                 400

Thr His Val Asp Ala Lys Ala Pro Gln Val Val Ser Phe Thr Gly Ser
            405                 410                 415

Phe Arg Lys Ala Leu Gly Gly Gly Gly Gly Glu Ala Glu Val
        420                 425                 430

Glu Lys Ile Tyr Arg Arg Ser Ile Arg Thr Val Thr Arg Asp Ile Trp
    435                 440                 445

Asp Lys Val Ser Ala Arg Leu Asp Cys Asp His Ile Ser Thr Thr His
450                 455                 460

Asn Pro Asp Glu Thr Leu Leu Asp Trp Trp Glu Arg Arg Thr Glu Gln
465                 470                 475                 480

Asn Asp Lys Asp Lys Thr Lys Gly Thr Arg Ser Ile His Met Leu Leu
            485                 490                 495

Ser Trp Glu Ile Trp Cys Glu Arg Asn Arg Arg Val Phe Arg Asn Lys
        500                 505                 510

Glu Leu Ala Ile Ser Gln Leu Val Thr Lys Ile Leu Asp Glu Ile Asn
    515                 520                 525

Val Trp Ile Ala Cys Gly Ala Lys Asn Leu Ala Arg Ile Val Leu
530                 535                 540

<210> SEQ ID NO 12
<211> LENGTH: 1557
<212> TYPE: DNA
<213> ORGANISM: Oryza sativa
<220> FEATURE:
<221> NAME/KEY: CDS
<222> LOCATION: (1)..(1557)

<400> SEQUENCE: 12 atg gtg gag gcc gcc gcg ggg cgc cgg tcg ggg gcc aac cgt cgg cgg      48
Met Val Glu Ala Ala Ala Gly Arg Arg Ser Gly Ala Asn Arg Arg Arg
1               5                   10                  15 cct agc ggc ggg ggc gag cgg cgg cgg cag cag cag cag cac cag cgc      96
Pro Ser Gly Gly Gly Glu Arg Arg Gln Gln Gln Gln His Gln Arg
            20                  25                  30
```

| | | |
|---|---|---|
| ctc gtc gcg gtc gcg gtg gcc gcg cgc gtc gtc atg gtg gcg ccc gcg<br>Leu Val Ala Val Ala Val Ala Arg Val Val Met Val Ala Pro Ala<br>     35                   40                   45 | | 144 |
| gcc acg ccg gcg ccc gcg gcg ggg ggt ggc ggg ggc tgc gtc gag gac<br>Ala Thr Pro Ala Pro Ala Ala Gly Gly Gly Gly Gly Cys Val Glu Asp<br> 50                    55                   60 | | 192 |
| atc ctc ggg tgc ctc ctc ggc gtg ctg cgc gcg ctc ggc gtc acg tgg<br>Ile Leu Gly Cys Leu Leu Gly Val Leu Arg Ala Leu Gly Val Thr Trp<br>65                    70                   75                   80 | | 240 |
| gcg gcg gcg gcg agg ccg cag agg cag cag ccg cgc ctg gcg gcg cag<br>Ala Ala Ala Ala Arg Pro Gln Arg Gln Gln Pro Arg Leu Ala Ala Gln<br>                    85                   90                   95 | | 288 |
| acg ccg cga ggg ccc gcg cct ggg gcg gat ggg cgc cgc gcc gcc gcc<br>Thr Pro Arg Gly Pro Ala Pro Gly Ala Asp Gly Arg Arg Ala Ala Ala<br>                  100                  105                110 | | 336 |
| gag ctg agg ggg atc ccc ggc cgg atc gcg ggg aac ggg gcc tgc gcc<br>Glu Leu Arg Gly Ile Pro Gly Arg Ile Ala Gly Asn Gly Ala Cys Ala<br>                 115                  120                125 | | 384 |
| gtc gcg tcg ctc tac acg ctg cag ggg aag aaa ggc gtc aac caa gac<br>Val Ala Ser Leu Tyr Thr Leu Gln Gly Lys Lys Gly Val Asn Gln Asp<br>      130                  135                  140 | | 432 |
| gcc atg atc gtc tgg gag aat ttc tgt tca aga gag gat acc att ttt<br>Ala Met Ile Val Trp Glu Asn Phe Cys Ser Arg Glu Asp Thr Ile Phe<br>145                    150                  155                160 | | 480 |
| tgt ggt gtt ttt gat ggc cat gga cca aac ggc cat ttg gtt gct aag<br>Cys Gly Val Phe Asp Gly His Gly Pro Asn Gly His Leu Val Ala Lys<br>                 165                  170                175 | | 528 |
| agg gtg aga gat ctt ctg ccc att aag ctt ggt gcg gat ttg ggg acg<br>Arg Val Arg Asp Leu Leu Pro Ile Lys Leu Gly Ala Asp Leu Gly Thr<br>      180                  185                  190 | | 576 |
| gat gaa gga cga cag aca tcc act agc agc atc aaa agc aat gga gat<br>Asp Glu Gly Arg Gln Thr Ser Thr Ser Ser Ile Lys Ser Asn Gly Asp<br>               195                  200                205 | | 624 |
| gaa aca gga tcc cct gga aac atg ggc aga gat gct gag cag aac gga<br>Glu Thr Gly Ser Pro Gly Asn Met Gly Arg Asp Ala Glu Gln Asn Gly<br>210                    215                  220 | | 672 |
| gag tac cca gag atc ttc aca gca ttg aga act tca ttt ttg agg gcg<br>Glu Tyr Pro Glu Ile Phe Thr Ala Leu Arg Thr Ser Phe Leu Arg Ala<br>225                    230                  235                240 | | 720 |
| ttc aat gtc atg gat aga gat ctc aag tta cat aaa agt ata gat tgt<br>Phe Asn Val Met Asp Arg Asp Leu Lys Leu His Lys Ser Ile Asp Cys<br>                 245                  250                255 | | 768 |
| ttt ttc agt gga aca aca gca gtg gca gtg ctc aag cag gga cgg aat<br>Phe Phe Ser Gly Thr Thr Ala Val Ala Val Leu Lys Gln Gly Arg Asn<br>               260                  265                270 | | 816 |
| ctt ata att ggt aac ctc ggg gac tcg cgg gcc atc tta ggc aca aga<br>Leu Ile Ile Gly Asn Leu Gly Asp Ser Arg Ala Ile Leu Gly Thr Arg<br>          275                  280                285 | | 864 |
| gat aaa gat aat cag ctt atg gct gtc caa ttg aca gtt gat ctc aaa<br>Asp Lys Asp Asn Gln Leu Met Ala Val Gln Leu Thr Val Asp Leu Lys<br>290                    295                  300 | | 912 |
| cct aac att cca agt gaa gca cag cga atc agg caa cgc agg ggc agg<br>Pro Asn Ile Pro Ser Glu Ala Gln Arg Ile Arg Gln Arg Arg Gly Arg<br>305                    310                  315                320 | | 960 |
| ata ttt gca ctt cct gag gag cca gag gtt gct cgt gtt tgg ctt ccg<br>Ile Phe Ala Leu Pro Glu Glu Pro Glu Val Ala Arg Val Trp Leu Pro<br>                 325                  330                335 | | 1008 |
| aag tac aac tcc cct gga ctg gcc atg gct agg gca ttt gga gac ttc<br>Lys Tyr Asn Ser Pro Gly Leu Ala Met Ala Arg Ala Phe Gly Asp Phe | | 1056 |

```
                  340                 345                 350
tgt ctc aag gat tat ggt cta atc tct atg cct gaa gtc tcg tac cac    1104
Cys Leu Lys Asp Tyr Gly Leu Ile Ser Met Pro Glu Val Ser Tyr His
        355                 360                 365 cgt atc aca gaa aag gat gag ttt gtt gta ttg gct act gat ggg gtt    1152
Arg Ile Thr Glu Lys Asp Glu Phe Val Val Leu Ala Thr Asp Gly Val
370                 375                 380 tgg gat gtg ctg tca aac act gaa gtt gtt agt att gtc aac aga gct    1200
Trp Asp Val Leu Ser Asn Thr Glu Val Val Ser Ile Val Asn Arg Ala
385                 390                 395                 400 act tct cgg gcc tct gca gca cga ttg cta gtc gaa tca gct cac cgt    1248
Thr Ser Arg Ala Ser Ala Ala Arg Leu Leu Val Glu Ser Ala His Arg
            405                 410                 415 gcc tgg cgt gca cgt ttc ccc act tct aaa att gat gat tgt gct gtg    1296
Ala Trp Arg Ala Arg Phe Pro Thr Ser Lys Ile Asp Asp Cys Ala Val
        420                 425                 430 gtc tgc cta ttc ctg gat aca gac gaa tta agt gaa aca tcc agt tct    1344
Val Cys Leu Phe Leu Asp Thr Asp Glu Leu Ser Glu Thr Ser Ser Ser
    435                 440                 445 atg gcc cgc gat atg aca aat gct gta gaa gtt agc agt ggg cag cac    1392
Met Ala Arg Asp Met Thr Asn Ala Val Glu Val Ser Ser Gly Gln His
450                 455                 460 tcc aat act atc caa ttg agc act gga gta tct tca gat gtt gtt act    1440
Ser Asn Thr Ile Gln Leu Ser Thr Gly Val Ser Ser Asp Val Val Thr
465                 470                 475                 480 gca gtt cta aca gat ggt gat gat ctg tct gct gtt gat gca gtt gca    1488
Ala Val Leu Thr Asp Gly Asp Asp Leu Ser Ala Val Asp Ala Val Ala
            485                 490                 495 aag ctg gtt act ctc acg gat ttg ccg aac aat gct tca ggc gca acg    1536
Lys Leu Val Thr Leu Thr Asp Leu Pro Asn Asn Ala Ser Gly Ala Thr
        500                 505                 510 caa agc atc acc acc aag tga                                        1557
Gln Ser Ile Thr Thr Lys
    515

<210> SEQ ID NO 13
<211> LENGTH: 518
<212> TYPE: PRT
<213> ORGANISM: Oryza sativa

<400> SEQUENCE: 13

Met Val Glu Ala Ala Gly Arg Arg Gly Ala Asn Arg Arg
1               5                   10              15

Pro Ser Gly Gly Glu Arg Arg Gln Gln Gln His Gln Arg
            20                  25                  30

Leu Val Ala Val Ala Val Ala Arg Val Val Met Val Ala Pro Ala
            35                  40                  45

Ala Thr Pro Ala Pro Ala Gly Gly Gly Gly Cys Val Glu Asp
    50                  55                  60

Ile Leu Gly Cys Leu Leu Gly Val Leu Arg Ala Leu Gly Val Thr Trp
65                  70                  75                  80

Ala Ala Ala Ala Arg Pro Gln Arg Gln Gln Pro Arg Leu Ala Ala Gln
                85                  90                  95

Thr Pro Arg Gly Pro Ala Pro Gly Ala Asp Gly Arg Arg Ala Ala Ala
            100                 105                 110

Glu Leu Arg Gly Ile Pro Gly Arg Ile Ala Gly Asn Gly Ala Cys Ala
        115                 120                 125

Val Ala Ser Leu Tyr Thr Leu Gln Gly Lys Lys Gly Val Asn Gln Asp
```

```
                130                 135                 140
Ala Met Ile Val Trp Glu Asn Phe Cys Ser Arg Glu Asp Thr Ile Phe
145                 150                 155                 160

Cys Gly Val Phe Asp Gly His Gly Pro Asn Gly His Leu Val Ala Lys
                165                 170                 175

Arg Val Arg Asp Leu Leu Pro Ile Lys Leu Gly Ala Asp Leu Gly Thr
            180                 185                 190

Asp Glu Gly Arg Gln Thr Ser Thr Ser Ser Ile Lys Ser Asn Gly Asp
        195                 200                 205

Glu Thr Gly Ser Pro Gly Asn Met Gly Arg Asp Ala Glu Gln Asn Gly
    210                 215                 220

Glu Tyr Pro Glu Ile Phe Thr Ala Leu Arg Thr Ser Phe Leu Arg Ala
225                 230                 235                 240

Phe Asn Val Met Asp Arg Asp Leu Lys Leu His Lys Ser Ile Asp Cys
                245                 250                 255

Phe Phe Ser Gly Thr Thr Ala Val Ala Val Leu Lys Gln Gly Arg Asn
            260                 265                 270

Leu Ile Ile Gly Asn Leu Gly Asp Ser Arg Ala Ile Leu Gly Thr Arg
        275                 280                 285

Asp Lys Asp Asn Gln Leu Met Ala Val Gln Leu Thr Val Asp Leu Lys
    290                 295                 300

Pro Asn Ile Pro Ser Glu Ala Gln Arg Ile Arg Gln Arg Gly Arg
305                 310                 315                 320

Ile Phe Ala Leu Pro Glu Glu Pro Glu Val Ala Arg Val Trp Leu Pro
                325                 330                 335

Lys Tyr Asn Ser Pro Gly Leu Ala Met Ala Arg Ala Phe Gly Asp Phe
            340                 345                 350

Cys Leu Lys Asp Tyr Gly Leu Ile Ser Met Pro Glu Val Ser Tyr His
        355                 360                 365

Arg Ile Thr Glu Lys Asp Glu Phe Val Val Leu Ala Thr Asp Gly Val
    370                 375                 380

Trp Asp Val Leu Ser Asn Thr Glu Val Val Ser Ile Val Asn Arg Ala
385                 390                 395                 400

Thr Ser Arg Ala Ser Ala Arg Leu Leu Val Glu Ser Ala His Arg
                405                 410                 415

Ala Trp Arg Ala Arg Phe Pro Thr Ser Lys Ile Asp Asp Cys Ala Val
            420                 425                 430

Val Cys Leu Phe Leu Asp Thr Asp Glu Leu Ser Glu Thr Ser Ser Ser
        435                 440                 445

Met Ala Arg Asp Met Thr Asn Ala Val Glu Val Ser Ser Gly Gln His
    450                 455                 460

Ser Asn Thr Ile Gln Leu Ser Thr Gly Val Ser Ser Asp Val Val Thr
465                 470                 475                 480

Ala Val Leu Thr Asp Gly Asp Asp Leu Ser Ala Val Asp Ala Val Ala
                485                 490                 495

Lys Leu Val Thr Leu Thr Asp Leu Pro Asn Asn Ala Ser Gly Ala Thr
            500                 505                 510

Gln Ser Ile Thr Thr Lys
        515

<210> SEQ ID NO 14
<211> LENGTH: 1383
<212> TYPE: DNA
<213> ORGANISM: Oryza sativa
```

```
<220> FEATURE:
<221> NAME/KEY: CDS
<222> LOCATION: (1)..(1383)

<400> SEQUENCE: 14 atg gtg gcg gtg acc ggg ggc agg ccc ccc ggc ctg cag gat gcg ccg      48
Met Val Ala Val Thr Gly Gly Arg Pro Pro Gly Leu Gln Asp Ala Pro
1               5                   10                  15 ggg gca cca cca cca gca cca gca gca gag gct gtg ccg tcg cgc ccg      96
Gly Ala Pro Pro Pro Ala Pro Ala Ala Glu Ala Val Pro Ser Arg Pro
            20                  25                  30 ctc gcg cgg gac gcg act tac gga ggc cgc gtg tac ggt ggc gta gga     144
Leu Ala Arg Asp Ala Thr Tyr Gly Gly Arg Val Tyr Gly Gly Val Gly
        35                  40                  45 gga gga gga tgc tgc ctc gag ttc ctc gac tgc gtg ctc cgg gcg atg     192
Gly Gly Gly Cys Cys Leu Glu Phe Leu Asp Cys Val Leu Arg Ala Met
50                  55                  60 ggc gtc gcc acc ccg gcc gag atc atg ccc ccc gcg gac ttc agg tgg     240
Gly Val Ala Thr Pro Ala Glu Ile Met Pro Pro Ala Asp Phe Arg Trp
65                  70                  75                  80 gcc gcg cgc ccg atg cgg cgg cgc cgc cgc ggg ggc tcc tcg tcc tcc     288
Ala Ala Arg Pro Met Arg Arg Arg Arg Gly Gly Ser Ser Ser Ser
                85                  90                  95 tcc tcc tcg ccg cgc gac cgc gag ccg agg gac ggc cgg atc gcc gcc     336
Ser Ser Ser Pro Arg Asp Arg Glu Pro Arg Asp Gly Arg Ile Ala Ala
            100                 105                 110 aac ggc gcc tcc gct gcc gcc tcg ctc tac acg atg cgg ggc aac aag     384
Asn Gly Ala Ser Ala Ala Ala Ser Leu Tyr Thr Met Arg Gly Asn Lys
        115                 120                 125 ggc gtc aac cag gac gcc atg ctt gtc tgg gag aat ttc tgt tca aag     432
Gly Val Asn Gln Asp Ala Met Leu Val Trp Glu Asn Phe Cys Ser Lys
    130                 135                 140 gaa gat aca att ttt tgt ggt gtt ttt gat ggc cat gga cca tat ggc     480
Glu Asp Thr Ile Phe Cys Gly Val Phe Asp Gly His Gly Pro Tyr Gly
145                 150                 155                 160 cat ttg gtg tcc aag agg gtc aga gat ctc ctc cct ata aag ttg agt     528
His Leu Val Ser Lys Arg Val Arg Asp Leu Leu Pro Ile Lys Leu Ser
                165                 170                 175 gca aat tta gga aga gat gga cac aaa gaa act tca act aac att gtc     576
Ala Asn Leu Gly Arg Asp Gly His Lys Glu Thr Ser Thr Asn Ile Val
            180                 185                 190 aca agc agc atg act gaa ggt ggt ggc acc gaa cgc atg gat aga gat     624
Thr Ser Ser Met Thr Glu Gly Gly Gly Thr Glu Arg Met Asp Arg Asp
        195                 200                 205 act gaa act ccc ctg gga acg gag gag aat gga gac tac ccc gag atg     672
Thr Glu Thr Pro Leu Gly Thr Glu Glu Asn Gly Asp Tyr Pro Glu Met
    210                 215                 220 ttt gct gca tta aga act tca tta tta agg gca ttt tat gta atg gac     720
Phe Ala Ala Leu Arg Thr Ser Leu Leu Arg Ala Phe Tyr Val Met Asp
225                 230                 235                 240 agg gat ctt aag ttt cat aaa acc att gac tct gtg ttc agt ggt act     768
Arg Asp Leu Lys Phe His Lys Thr Ile Asp Ser Val Phe Ser Gly Thr
                245                 250                 255 aca gca gtc aca gtg atc aag cag gga cat gat ctc ctg att gga aac     816
Thr Ala Val Thr Val Ile Lys Gln Gly His Asp Leu Leu Ile Gly Asn
            260                 265                 270 ttg ggg gat tct aga gct gtc ttg gga act aga gat gaa tat gac cag     864
Leu Gly Asp Ser Arg Ala Val Leu Gly Thr Arg Asp Glu Tyr Asp Gln
        275                 280                 285 ttt ttt gct gta caa ttg aca gtt gac ctg aag cct acc att cca agt     912
```

```
Phe Phe Ala Val Gln Leu Thr Val Asp Leu Lys Pro Thr Ile Pro Ser
    290                 295                 300 gaa gct gca cga att agg gaa cga agt ggc aga ata ttc tct ctg cca       960
Glu Ala Ala Arg Ile Arg Glu Arg Ser Gly Arg Ile Phe Ser Leu Pro
305                 310                 315                 320 gat gag cca gat gtt gct cgt gtt tgg ctt ccg aag tac aac atg cca      1008
Asp Glu Pro Asp Val Ala Arg Val Trp Leu Pro Lys Tyr Asn Met Pro
                325                 330                 335 ggg ttg gcc atg gca aga gca ttt gga gac ttt tgt cta aag gat tat      1056
Gly Leu Ala Met Ala Arg Ala Phe Gly Asp Phe Cys Leu Lys Asp Tyr
            340                 345                 350 ggt cta att tct atg cct gat gtt tcc tac cac cgc atc act gaa aag      1104
Gly Leu Ile Ser Met Pro Asp Val Ser Tyr His Arg Ile Thr Glu Lys
        355                 360                 365 gat gaa ttt gtt gtg ttg gca act gat ggg gtg tgg gat gta ctt tcc      1152
Asp Glu Phe Val Val Leu Ala Thr Asp Gly Val Trp Asp Val Leu Ser
370                 375                 380 aac tca gaa gtt gtt agc att gtc agc caa gcc aag tca gaa gcc tca      1200
Asn Ser Glu Val Val Ser Ile Val Ser Gln Ala Lys Ser Glu Ala Ser
385                 390                 395                 400 gcg gca cga ttt gtt gtt gaa tcg gct caa cgt gca tgg aga aca cgg      1248
Ala Ala Arg Phe Val Val Glu Ser Ala Gln Arg Ala Trp Arg Thr Arg
                405                 410                 415 ttc ccc aca tca aaa att gat gac tgc gct gtt gtc tgc ctg ttc ttg      1296
Phe Pro Thr Ser Lys Ile Asp Asp Cys Ala Val Val Cys Leu Phe Leu
            420                 425                 430 aat aca gat gct aga aat aaa ccc ccc ggt tca gga atc aaa gat ttg      1344
Asn Thr Asp Ala Arg Asn Lys Pro Pro Gly Ser Gly Ile Lys Asp Leu
        435                 440                 445 gcc aat gcc ata gaa ctg ggt ggt ggt aat ctt tct tga                  1383
Ala Asn Ala Ile Glu Leu Gly Gly Gly Asn Leu Ser
450                 455                 460

<210> SEQ ID NO 15
<211> LENGTH: 460
<212> TYPE: PRT
<213> ORGANISM: Oryza sativa

<400> SEQUENCE: 15

Met Val Ala Val Thr Gly Gly Arg Pro Pro Gly Leu Gln Asp Ala Pro
1               5                   10                  15

Gly Ala Pro Pro Ala Pro Ala Ala Glu Ala Val Pro Ser Arg Pro
            20                  25                  30

Leu Ala Arg Asp Ala Thr Tyr Gly Gly Arg Val Tyr Gly Gly Val Gly
        35                  40                  45

Gly Gly Gly Cys Cys Leu Glu Phe Leu Asp Cys Val Leu Arg Ala Met
    50                  55                  60

Gly Val Ala Thr Pro Ala Glu Ile Met Pro Pro Ala Asp Phe Arg Trp
65                  70                  75                  80

Ala Ala Arg Pro Met Arg Arg Arg Arg Gly Gly Ser Ser Ser
                85                  90                  95

Ser Ser Ser Pro Arg Asp Arg Glu Pro Arg Asp Gly Arg Ile Ala Ala
                100                 105                 110

Asn Gly Ala Ser Ala Ala Ala Ser Leu Tyr Thr Met Arg Gly Asn Lys
            115                 120                 125

Gly Val Asn Gln Asp Ala Met Leu Val Trp Glu Asn Phe Cys Ser Lys
        130                 135                 140

Glu Asp Thr Ile Phe Cys Gly Val Phe Asp Gly His Gly Pro Tyr Gly
```

```
        145                 150                 155                 160
His Leu Val Ser Lys Arg Val Arg Asp Leu Leu Pro Ile Lys Leu Ser
                165                 170                 175

Ala Asn Leu Gly Arg Asp Gly His Lys Glu Thr Ser Thr Asn Ile Val
            180                 185                 190

Thr Ser Ser Met Thr Glu Gly Gly Thr Glu Arg Met Asp Arg Asp
        195                 200                 205

Thr Glu Thr Pro Leu Gly Thr Glu Asn Gly Asp Tyr Pro Glu Met
    210                 215                 220

Phe Ala Ala Leu Arg Thr Ser Leu Leu Arg Ala Phe Tyr Val Met Asp
225                 230                 235                 240

Arg Asp Leu Lys Phe His Lys Thr Ile Asp Ser Val Phe Ser Gly Thr
                245                 250                 255

Thr Ala Val Thr Val Ile Lys Gln Gly His Asp Leu Leu Ile Gly Asn
            260                 265                 270

Leu Gly Asp Ser Arg Ala Val Leu Gly Thr Arg Asp Glu Tyr Asp Gln
        275                 280                 285

Phe Phe Ala Val Gln Leu Thr Val Asp Leu Lys Pro Thr Ile Pro Ser
    290                 295                 300

Glu Ala Ala Arg Ile Arg Glu Arg Ser Gly Arg Ile Phe Ser Leu Pro
305                 310                 315                 320

Asp Glu Pro Asp Val Ala Arg Val Trp Leu Pro Lys Tyr Asn Met Pro
                325                 330                 335

Gly Leu Ala Met Ala Arg Ala Phe Gly Asp Phe Cys Leu Lys Asp Tyr
            340                 345                 350

Gly Leu Ile Ser Met Pro Asp Val Ser Tyr His Arg Ile Thr Glu Lys
        355                 360                 365

Asp Glu Phe Val Val Leu Ala Thr Asp Gly Val Trp Asp Val Leu Ser
    370                 375                 380

Asn Ser Glu Val Val Ser Ile Val Ser Gln Ala Lys Ser Glu Ala Ser
385                 390                 395                 400

Ala Ala Arg Phe Val Val Glu Ser Ala Gln Arg Ala Trp Arg Thr Arg
                405                 410                 415

Phe Pro Thr Ser Lys Ile Asp Asp Cys Ala Val Val Cys Leu Phe Leu
            420                 425                 430

Asn Thr Asp Ala Arg Asn Lys Pro Pro Gly Ser Gly Ile Lys Asp Leu
        435                 440                 445

Ala Asn Ala Ile Glu Leu Gly Gly Asn Leu Ser
    450                 455                 460

<210> SEQ ID NO 16
<211> LENGTH: 1299
<212> TYPE: DNA
<213> ORGANISM: Oryza sativa
<220> FEATURE:
<221> NAME/KEY: CDS
<222> LOCATION: (1)..(1299)

<400> SEQUENCE: 16 atg ggg aca tgc ctt acg acg gcg gag cag cgg gcc atg gag gtg ccg    48
Met Gly Thr Cys Leu Thr Thr Ala Glu Gln Arg Ala Met Glu Val Pro
1               5                   10                  15 gct gcg tcg gtg aag gga gga ggg ggc agg agg agt gac gag gag gcg    96
Ala Ala Ser Val Lys Gly Gly Gly Gly Arg Arg Ser Asp Glu Glu Ala
            20                  25                  30 ccc ggc agg atc gcg ggt aac ggc gcg ggg aat gtg gcc tgc ctg ttc   144
```

```
              Pro Gly Arg Ile Ala Gly Asn Gly Ala Gly Asn Val Ala Cys Leu Phe
                      35                  40                  45 act cgg cag ggg aag aag ggc acc aac cag gat gcc atg gtc gcg tgg          192
Thr Arg Gln Gly Lys Lys Gly Thr Asn Gln Asp Ala Met Val Ala Trp
 50                  55                  60 gag aac tat aac gga aga tca gac acg gta ttt tgt gga gtt ttt gat          240
Glu Asn Tyr Asn Gly Arg Ser Asp Thr Val Phe Cys Gly Val Phe Asp
 65                  70                  75                  80 ggc cac ggt cca cat ggc cat ctc att gct agg aaa gta aga gat att          288
Gly His Gly Pro His Gly His Leu Ile Ala Arg Lys Val Arg Asp Ile
                 85                  90                  95 ctc cct tcg aga ctc tgt gat ttg ata tat gaa gac tgt ggg gat agt          336
Leu Pro Ser Arg Leu Cys Asp Leu Ile Tyr Glu Asp Cys Gly Asp Ser
                100                 105                 110 cca acc agc aat tca gat gtc tca act ctg gaa gag aat tta tct ccg          384
Pro Thr Ser Asn Ser Asp Val Ser Thr Leu Glu Glu Asn Leu Ser Pro
                115                 120                 125 tat gca gat gca gag tgc aga tct ccc aca ttg gct gga caa aaa gaa          432
Tyr Ala Asp Ala Glu Cys Arg Ser Pro Thr Leu Ala Gly Gln Lys Glu
                130                 135                 140 cat caa gaa ttc ttc aac gca atg aaa gaa tct ttc aga aag gct ttt          480
His Gln Glu Phe Phe Asn Ala Met Lys Glu Ser Phe Arg Lys Ala Phe
145                 150                 155                 160 aaa aat gtg gat aag gag ctc aaa tta caa cgg aac att gat agc att          528
Lys Asn Val Asp Lys Glu Leu Lys Leu Gln Arg Asn Ile Asp Ser Ile
                165                 170                 175 tgc agt gga act act gca gtt act tta atc aag caa ggt cat gat ctt          576
Cys Ser Gly Thr Thr Ala Val Thr Leu Ile Lys Gln Gly His Asp Leu
                180                 185                 190 att gtt ggg aat cta ggt gac tct aga gct gta tta ggc acc aga gat          624
Ile Val Gly Asn Leu Gly Asp Ser Arg Ala Val Leu Gly Thr Arg Asp
                195                 200                 205 cag aac gat aag ttg gtt gct cat cag ttg act gtt gac ctg aaa cct          672
Gln Asn Asp Lys Leu Val Ala His Gln Leu Thr Val Asp Leu Lys Pro
                210                 215                 220 gat cat cca agg gag gct agg agg atc aga cgg tgt aat ggg agg gtc          720
Asp His Pro Arg Glu Ala Arg Arg Ile Arg Arg Cys Asn Gly Arg Val
225                 230                 235                 240 ttt gct cat cag gat gaa cca gat gtg gct cgc ctt tgg ctt cct aat          768
Phe Ala His Gln Asp Glu Pro Asp Val Ala Arg Leu Trp Leu Pro Asn
                245                 250                 255 tgc aac tct cct gga ctg gca atg gcc cga gct ttt ggt gac ttt tgt          816
Cys Asn Ser Pro Gly Leu Ala Met Ala Arg Ala Phe Gly Asp Phe Cys
                260                 265                 270 cta aag gat ttt ggg ttg atc tca gta cct gat gtc acc tat agg caa          864
Leu Lys Asp Phe Gly Leu Ile Ser Val Pro Asp Val Thr Tyr Arg Gln
                275                 280                 285 att act gaa aaa gac gag ttt att gtc ctg gcg aca gat ggg gtg tgg          912
Ile Thr Glu Lys Asp Glu Phe Ile Val Leu Ala Thr Asp Gly Val Trp
                290                 295                 300 gat gtt ctc tcc aac cag gaa gtg gtg gat gtt gtt gcc tca tgc tct          960
Asp Val Leu Ser Asn Gln Glu Val Val Asp Val Val Ala Ser Cys Ser
305                 310                 315                 320 ggt cgt ttc gct gca gct cgt tct gtt gtt gat tta gca aat gag act         1008
Gly Arg Phe Ala Ala Ala Arg Ser Val Val Asp Leu Ala Asn Glu Thr
                325                 330                 335 tgg agg ttc aaa tac cca acc tca aaa act gat gat tgt gca gtg gtc         1056
Trp Arg Phe Lys Tyr Pro Thr Ser Lys Thr Asp Asp Cys Ala Val Val
                340                 345                 350
```

```
tgt ctt ttc ctg aac aag tat gaa gtt acc ggt ggt tta tca ggg caa    1104
Cys Leu Phe Leu Asn Lys Tyr Glu Val Thr Gly Gly Leu Ser Gly Gln
            355                 360                 365 cct gga tat agt cca agg atg cct gcc cta tca ggt att acc cgg ccc    1152
Pro Gly Tyr Ser Pro Arg Met Pro Ala Leu Ser Gly Ile Thr Arg Pro
    370                 375                 380 aat agt aaa agg gtt act cct gac gac gtc gat gat ggt agt gac tca    1200
Asn Ser Lys Arg Val Thr Pro Asp Asp Val Asp Asp Gly Ser Asp Ser
385                 390                 395                 400 aac gta agc gga gat gag agg tcc ttg gat ggt ttc act cga ttg aac    1248
Asn Val Ser Gly Asp Glu Arg Ser Leu Asp Gly Phe Thr Arg Leu Asn
                405                 410                 415 aca ttg ttg gca cta cca aag ttt ggt gac aca agt cca act aag aaa    1296
Thr Leu Leu Ala Leu Pro Lys Phe Gly Asp Thr Ser Pro Thr Lys Lys
            420                 425                 430 tga                                                                1299

<210> SEQ ID NO 17
<211> LENGTH: 432
<212> TYPE: PRT
<213> ORGANISM: Oryza sativa

<400> SEQUENCE: 17

Met Gly Thr Cys Leu Thr Thr Ala Glu Gln Arg Ala Met Glu Val Pro
1               5                   10                  15

Ala Ala Ser Val Lys Gly Gly Gly Arg Arg Ser Asp Glu Ala
                20                  25                  30

Pro Gly Arg Ile Ala Gly Asn Gly Ala Gly Asn Val Ala Cys Leu Phe
            35                  40                  45

Thr Arg Gln Gly Lys Lys Gly Thr Asn Gln Asp Ala Met Val Ala Trp
        50                  55                  60

Glu Asn Tyr Asn Gly Arg Ser Asp Thr Val Phe Cys Gly Val Phe Asp
65                  70                  75                  80

Gly His Gly Pro His Gly His Leu Ile Ala Arg Lys Val Arg Asp Ile
                85                  90                  95

Leu Pro Ser Arg Leu Cys Asp Leu Ile Tyr Glu Asp Cys Gly Asp Ser
            100                 105                 110

Pro Thr Ser Asn Ser Asp Val Ser Thr Leu Glu Glu Asn Leu Ser Pro
        115                 120                 125

Tyr Ala Asp Ala Glu Cys Arg Ser Pro Thr Leu Ala Gly Gln Lys Glu
    130                 135                 140

His Gln Glu Phe Phe Asn Ala Met Lys Glu Ser Phe Arg Lys Ala Phe
145                 150                 155                 160

Lys Asn Val Asp Lys Glu Leu Lys Leu Gln Arg Asn Ile Asp Ser Ile
                165                 170                 175

Cys Ser Gly Thr Thr Ala Val Thr Leu Ile Lys Gln Gly His Asp Leu
            180                 185                 190

Ile Val Gly Asn Leu Gly Asp Ser Arg Ala Val Leu Gly Thr Arg Asp
        195                 200                 205

Gln Asn Asp Lys Leu Val Ala His Gln Leu Thr Val Asp Leu Lys Pro
    210                 215                 220

Asp His Pro Arg Glu Ala Arg Ile Arg Arg Cys Asn Gly Arg Val
225                 230                 235                 240

Phe Ala His Gln Asp Glu Pro Asp Val Ala Arg Leu Trp Leu Pro Asn
                245                 250                 255

Cys Asn Ser Pro Gly Leu Ala Met Ala Arg Ala Phe Gly Asp Phe Cys
```

```
                      260                 265                 270
Leu Lys Asp Phe Gly Leu Ile Ser Val Pro Asp Val Thr Tyr Arg Gln
            275                 280                 285

Ile Thr Glu Lys Asp Glu Phe Ile Val Leu Ala Thr Asp Gly Val Trp
        290                 295                 300

Asp Val Leu Ser Asn Gln Glu Val Val Asp Val Ala Ser Cys Ser
305                 310                 315                 320

Gly Arg Phe Ala Ala Arg Ser Val Val Asp Leu Ala Asn Glu Thr
                325                 330                 335

Trp Arg Phe Lys Tyr Pro Thr Ser Lys Thr Asp Asp Cys Ala Val Val
            340                 345                 350

Cys Leu Phe Leu Asn Lys Tyr Glu Val Thr Gly Gly Leu Ser Gly Gln
            355                 360                 365

Pro Gly Tyr Ser Pro Arg Met Pro Ala Leu Ser Gly Ile Thr Arg Pro
        370                 375                 380

Asn Ser Lys Arg Val Thr Pro Asp Asp Val Asp Asp Gly Ser Asp Ser
385                 390                 395                 400

Asn Val Ser Gly Asp Glu Arg Ser Leu Asp Gly Phe Thr Arg Leu Asn
                405                 410                 415

Thr Leu Leu Ala Leu Pro Lys Phe Gly Asp Thr Ser Pro Thr Lys Lys
            420                 425                 430

<210> SEQ ID NO 18
<211> LENGTH: 1284
<212> TYPE: DNA
<213> ORGANISM: Oryza sativa
<220> FEATURE:
<221> NAME/KEY: CDS
<222> LOCATION: (1)..(1284)

<400> SEQUENCE: 18 atg ggg aac tgc gtg gcg agg agc ggg acg gcg gtg gat gcg ggt ggt     48
Met Gly Asn Cys Val Ala Arg Ser Gly Thr Ala Val Asp Ala Gly Gly
1               5                   10                  15 gat gga ggg gag gat ggg aag agg cgg agg agg agg tgg aag gcg ccg     96
Asp Gly Gly Glu Asp Gly Lys Arg Arg Arg Arg Arg Trp Lys Ala Pro
                20                  25                  30 cgg gaa gat cag ctc ggg atg gtg ccc ggc cgg atc ttc tcc aac gac    144
Arg Glu Asp Gln Leu Gly Met Val Pro Gly Arg Ile Phe Ser Asn Asp
            35                  40                  45 ggc cgc agc cgg acg gcg acg gtg tac acg cag caa ggg cgc aag ggg    192
Gly Arg Ser Arg Thr Ala Thr Val Tyr Thr Gln Gln Gly Arg Lys Gly
        50                  55                  60 atc aac cag gac gcc atg ctc gtc tgg gat ggg ttc ggc ggc gag gac    240
Ile Asn Gln Asp Ala Met Leu Val Trp Asp Gly Phe Gly Gly Glu Asp
65                  70                  75                  80 gac ggc gtg ctg tgc ggg gtg ttc gac ggg cac ggg ccg cac ggg cac    288
Asp Gly Val Leu Cys Gly Val Phe Asp Gly His Gly Pro His Gly His
                85                  90                  95 gtg gtg gcg cgg agg gtc cgc gac tcg ctg ccg ctg agg ctc atg tcc    336
Val Val Ala Arg Arg Val Arg Asp Ser Leu Pro Leu Arg Leu Met Ser
            100                 105                 110 gcg gcg cgc gac agc ggg gcg gac atg ccg gcc gcc gca tgg agg aag    384
Ala Ala Arg Asp Ser Gly Ala Asp Met Pro Ala Ala Ala Trp Arg Lys
        115                 120                 125 gcc ttc gcg cgc gcc tac aag gcc atg gac aag gac ctc cgg tcg cac    432
Ala Phe Ala Arg Ala Tyr Lys Ala Met Asp Lys Asp Leu Arg Ser His
    130                 135                 140
```

```
cct tcc ctc gat tgc ttc tgc agc gga agc act gcc gtc acc gtc ctc      480
Pro Ser Leu Asp Cys Phe Cys Ser Gly Ser Thr Ala Val Thr Val Leu
145                 150                 155                 160 aag ctc ggc tcg gat ctc tac atg gcc aac att ggg gac tcg cgc gcc      528
Lys Leu Gly Ser Asp Leu Tyr Met Ala Asn Ile Gly Asp Ser Arg Ala
                165                 170                 175 gtg ctc ggc tcc agg gag gcc acc ggc ggc ggc atg gtc gcc gtg cag      576
Val Leu Gly Ser Arg Glu Ala Thr Gly Gly Gly Met Val Ala Val Gln
            180                 185                 190 ctc acc gtt gat ctc aag ccg gat gtc ccc agc gaa gcg gag agg atc      624
Leu Thr Val Asp Leu Lys Pro Asp Val Pro Ser Glu Ala Glu Arg Ile
        195                 200                 205 aag aag tgc agg ggc agg gtg ttc gcg ctg cag gac gag ccg gag gtg      672
Lys Lys Cys Arg Gly Arg Val Phe Ala Leu Gln Asp Glu Pro Glu Val
    210                 215                 220 cca agg gtc tgg ctg ccg ttc gac gac gcg ccg ggc ctc gcg atg gcg      720
Pro Arg Val Trp Leu Pro Phe Asp Asp Ala Pro Gly Leu Ala Met Ala
225                 230                 235                 240 cga gcg ttc ggg gac ttc tgc ctg aaa gat tac ggg gtc atc tcg gtg      768
Arg Ala Phe Gly Asp Phe Cys Leu Lys Asp Tyr Gly Val Ile Ser Val
                245                 250                 255 ccg gaa ttc ttc cac tgg tct ctc aca gaa aag gac cag ttc gtc att      816
Pro Glu Phe Phe His Trp Ser Leu Thr Glu Lys Asp Gln Phe Val Ile
            260                 265                 270 ctt gca tcg gat ggg gta tgg gat gtc ctc agc aat caa gag gct gtt      864
Leu Ala Ser Asp Gly Val Trp Asp Val Leu Ser Asn Gln Glu Ala Val
        275                 280                 285 gat ata gtg tcc gcg tcc cca agc aga tca aag gct gca aaa tcc ctt      912
Asp Ile Val Ser Ala Ser Pro Ser Arg Ser Lys Ala Ala Lys Ser Leu
    290                 295                 300 gtt gag gca gcc act cgt gaa tgg aaa acc aaa tat cca aca tcc aaa      960
Val Glu Ala Ala Thr Arg Glu Trp Lys Thr Lys Tyr Pro Thr Ser Lys
305                 310                 315                 320 atc gat gat tgc gcg gtt gtt tgc tta tat ttg gat gga aaa atg gac     1008
Ile Asp Asp Cys Ala Val Val Cys Leu Tyr Leu Asp Gly Lys Met Asp
                325                 330                 335 cat gag cgt gac tca act gcc tca ttg gac aac atc agt att gaa gag     1056
His Glu Arg Asp Ser Thr Ala Ser Leu Asp Asn Ile Ser Ile Glu Glu
            340                 345                 350 ggt tca gtt gca gat cct aat gaa cct cag gag cag gag ccc acc tta     1104
Gly Ser Val Ala Asp Pro Asn Glu Pro Gln Glu Gln Glu Pro Thr Leu
        355                 360                 365 act cgg aat ttc aca gtt agg aca gtt gca ggc agc acg caa gag aag     1152
Thr Arg Asn Phe Thr Val Arg Thr Val Ala Gly Ser Thr Gln Glu Lys
    370                 375                 380 acc tta gca ggg gtg gat gcg agg att gct ggt gta gcg aac gac caa     1200
Thr Leu Ala Gly Val Asp Ala Arg Ile Ala Gly Val Ala Asn Asp Gln
385                 390                 395                 400 aat tgg tca ggt ctc gat gga gtg aca cgg gta aac tca ctt gtt cag     1248
Asn Trp Ser Gly Leu Asp Gly Val Thr Arg Val Asn Ser Leu Val Gln
                405                 410                 415 ctt cct agg ttt tct gaa gag agg gca att ggc tga                     1284
Leu Pro Arg Phe Ser Glu Glu Arg Ala Ile Gly
            420                 425

<210> SEQ ID NO 19
<211> LENGTH: 427
<212> TYPE: PRT
<213> ORGANISM: Oryza sativa

<400> SEQUENCE: 19
```

-continued

```
Met Gly Asn Cys Val Ala Arg Ser Gly Thr Ala Val Asp Ala Gly Gly
1               5                   10                  15

Asp Gly Gly Glu Asp Gly Lys Arg Arg Arg Arg Trp Lys Ala Pro
            20                  25                  30

Arg Glu Asp Gln Leu Gly Met Val Pro Gly Arg Ile Phe Ser Asn Asp
            35                  40                  45

Gly Arg Ser Arg Thr Ala Thr Val Tyr Thr Gln Gln Gly Arg Lys Gly
            50                  55                  60

Ile Asn Gln Asp Ala Met Leu Val Trp Asp Gly Phe Gly Gly Glu Asp
65                  70                  75                  80

Asp Gly Val Leu Cys Gly Val Phe Asp Gly His Gly Pro His Gly His
                85                  90                  95

Val Val Ala Arg Arg Val Arg Asp Ser Leu Pro Leu Arg Leu Met Ser
                100                 105                 110

Ala Ala Arg Asp Ser Gly Ala Asp Met Pro Ala Ala Ala Trp Arg Lys
                115                 120                 125

Ala Phe Ala Arg Ala Tyr Lys Ala Met Asp Lys Asp Leu Arg Ser His
130                 135                 140

Pro Ser Leu Asp Cys Phe Cys Ser Gly Ser Thr Ala Val Thr Val Leu
145                 150                 155                 160

Lys Leu Gly Ser Asp Leu Tyr Met Ala Asn Ile Gly Asp Ser Arg Ala
                165                 170                 175

Val Leu Gly Ser Arg Glu Ala Thr Gly Gly Met Val Ala Val Gln
                180                 185                 190

Leu Thr Val Asp Leu Lys Pro Asp Val Pro Ser Glu Ala Glu Arg Ile
                195                 200                 205

Lys Lys Cys Arg Gly Arg Val Phe Ala Leu Gln Asp Glu Pro Glu Val
210                 215                 220

Pro Arg Val Trp Leu Pro Phe Asp Asp Ala Pro Gly Leu Ala Met Ala
225                 230                 235                 240

Arg Ala Phe Gly Asp Phe Cys Leu Lys Asp Tyr Gly Val Ile Ser Val
                245                 250                 255

Pro Glu Phe Phe His Trp Ser Leu Thr Glu Lys Asp Gln Phe Val Ile
                260                 265                 270

Leu Ala Ser Asp Gly Val Trp Asp Val Leu Ser Asn Gln Glu Ala Val
                275                 280                 285

Asp Ile Val Ser Ala Ser Pro Ser Arg Ser Lys Ala Ala Lys Ser Leu
290                 295                 300

Val Glu Ala Ala Thr Arg Glu Trp Lys Thr Lys Tyr Pro Thr Ser Lys
305                 310                 315                 320

Ile Asp Asp Cys Ala Val Val Cys Leu Tyr Leu Asp Gly Lys Met Asp
                325                 330                 335

His Glu Arg Asp Ser Thr Ala Ser Leu Asp Asn Ile Ser Ile Glu Glu
                340                 345                 350

Gly Ser Val Ala Asp Pro Asn Glu Pro Gln Glu Gln Glu Pro Thr Leu
                355                 360                 365

Thr Arg Asn Phe Thr Val Arg Thr Val Ala Gly Ser Thr Gln Glu Lys
370                 375                 380

Thr Leu Ala Gly Val Asp Ala Arg Ile Ala Gly Val Ala Asn Asp Gln
385                 390                 395                 400

Asn Trp Ser Gly Leu Asp Gly Val Thr Arg Val Asn Ser Leu Val Gln
                405                 410                 415
```

```
                    Leu Pro Arg Phe Ser Glu Glu Arg Ala Ile Gly
                                420                 425

<210> SEQ ID NO 20
<211> LENGTH: 1596
<212> TYPE: DNA
<213> ORGANISM: Oryza sativa
<220> FEATURE:
<221> NAME/KEY: CDS
<222> LOCATION: (1)..(1596)

<400> SEQUENCE: 20 atg ggc tcc tgc ctc tcc tcc gac ctg cct ccc cgc gcc ggc gcc ggc        48
Met Gly Ser Cys Leu Ser Ser Asp Leu Pro Pro Arg Ala Gly Ala Gly
  1               5                  10                  15 gcg gga gcg tca ccc ggg tgg ccg cag cgg tgg cgg agg agg agg cag        96
Ala Gly Ala Ser Pro Gly Trp Pro Gln Arg Trp Arg Arg Arg Arg Gln
             20                  25                  30 cgg ggg gtg gag cgg ggc ggg gct gtt tcc ggc ggc ggc ggc ggc gtc       144
Arg Gly Val Glu Arg Gly Gly Ala Val Ser Gly Gly Gly Gly Gly Val
         35                  40                  45 ttc tcc atc ggc gtc ggc ggc aag aag ctg cac cac ggc ggc gga gga       192
Phe Ser Ile Gly Val Gly Gly Lys Lys Leu His His Gly Gly Gly Gly
     50                  55                  60 gga ggg gag atg acg gag gag gag ctc gcg aag gtc gag ggg agg gtg       240
Gly Gly Glu Met Thr Glu Glu Glu Leu Ala Lys Val Glu Gly Arg Val
 65                  70                  75                  80 tgc gtc aac ggc gcg agc gcg gcg gcg tgc ctg cac acg cag cag ggg       288
Cys Val Asn Gly Ala Ser Ala Ala Ala Cys Leu His Thr Gln Gln Gly
                 85                  90                  95 cgg aag ggc acc aac cag gac gcc atg gtc gtg tgg gag aac ttt aat       336
Arg Lys Gly Thr Asn Gln Asp Ala Met Val Val Trp Glu Asn Phe Asn
            100                 105                 110 aca agt gat agt gtc ttc tgt ggt gtg ttt gat ggt cat ggt cca tat       384
Thr Ser Asp Ser Val Phe Cys Gly Val Phe Asp Gly His Gly Pro Tyr
        115                 120                 125 ggt cat ttt gtt gcc aag aag gtc aga gat tct ctt cct gtc aaa ata       432
Gly His Phe Val Ala Lys Lys Val Arg Asp Ser Leu Pro Val Lys Ile
    130                 135                 140 cgc aca cta tgg aaa acc agt gcc aac gag gac act agt tcc cac caa       480
Arg Thr Leu Trp Lys Thr Ser Ala Asn Glu Asp Thr Ser Ser His Gln
145                 150                 155                 160 aat gga agc att tct gga agt gtt aat tca gaa gag tca cct gtt gtt       528
Asn Gly Ser Ile Ser Gly Ser Val Asn Ser Glu Glu Ser Pro Val Val
                165                 170                 175 gat gat gaa tgg ggt gaa tat gct gat gac agc gag aag ctt cct gag       576
Asp Asp Glu Trp Gly Glu Tyr Ala Asp Asp Ser Glu Lys Leu Pro Glu
            180                 185                 190 atg ttt ctt cca ctt aag cag tct tat ttt aag gct ttc aaa ttg atg       624
Met Phe Leu Pro Leu Lys Gln Ser Tyr Phe Lys Ala Phe Lys Leu Met
        195                 200                 205 gac aag gaa ctc aaa atg cac cct aca gtt gat tgc ttt tgc agt gga       672
Asp Lys Glu Leu Lys Met His Pro Thr Val Asp Cys Phe Cys Ser Gly
    210                 215                 220 tca aca gca gtc acg tta gta aaa cag gga ttg gat ctt gtg gtt ggg       720
Ser Thr Ala Val Thr Leu Val Lys Gln Gly Leu Asp Leu Val Val Gly
225                 230                 235                 240 aac ctt ggg gac tcg aga gca ata atg ggg aca cga gat gct gcc aat       768
Asn Leu Gly Asp Ser Arg Ala Ile Met Gly Thr Arg Asp Ala Ala Asn
                245                 250                 255 aat cta act gct gta caa ctc aca gtt gat ttg aag cct aac ctt cca       816
```

```
                Asn Leu Thr Ala Val Gln Leu Thr Val Asp Leu Lys Pro Asn Leu Pro
                                260                 265                 270 agg gaa gct gcg agg atc cag cag tgt agg gga aga gtt ttt gct ctt           864
Arg Glu Ala Ala Arg Ile Gln Gln Cys Arg Gly Arg Val Phe Ala Leu
            275                 280                 285 cag gat gaa cca gaa gtt gcc aga gta tgg ttg cca aat aat gac tct           912
Gln Asp Glu Pro Glu Val Ala Arg Val Trp Leu Pro Asn Asn Asp Ser
290                 295                 300 cct gga ttg gca atg gca aga gct ttt gga gac ttc tgc ctt aaa gat           960
Pro Gly Leu Ala Met Ala Arg Ala Phe Gly Asp Phe Cys Leu Lys Asp
305                 310                 315                 320 tat ggt tta ata tct gtt cca cag ata tcc tat cgt cgt ctt act gaa          1008
Tyr Gly Leu Ile Ser Val Pro Gln Ile Ser Tyr Arg Arg Leu Thr Glu
                325                 330                 335 aag gat gag ttc ata ata ctg gcc act gat ggg gtt tgg gac gtc ctc          1056
Lys Asp Glu Phe Ile Ile Leu Ala Thr Asp Gly Val Trp Asp Val Leu
            340                 345                 350 tca aac aag gag gct gtt gac ata gta gcc gca gct cca tct cgt gca          1104
Ser Asn Lys Glu Ala Val Asp Ile Val Ala Ala Ala Pro Ser Arg Ala
355                 360                 365 acg gct gcc agg gct ctt gtc gac tgt gct gtc aga tca tgg aga ttg          1152
Thr Ala Ala Arg Ala Leu Val Asp Cys Ala Val Arg Ser Trp Arg Leu
370                 375                 380 aag ttc cca aca tcc aag agc gat gac tgc gct gtt gtg tgc cta ttc          1200
Lys Phe Pro Thr Ser Lys Ser Asp Asp Cys Ala Val Val Cys Leu Phe
385                 390                 395                 400 tta gac cat gca aag tca cct gac ttg att caa gag aac gag agc gag          1248
Leu Asp His Ala Lys Ser Pro Asp Leu Ile Gln Glu Asn Glu Ser Glu
                405                 410                 415 gaa gaa act aca gag gat gtt gca atc cca gac acc gtt gct aag gtt          1296
Glu Glu Thr Thr Glu Asp Val Ala Ile Pro Asp Thr Val Ala Lys Val
            420                 425                 430 gac caa gac att gca caa gga gat gca cat atc tcc agt gaa gag caa          1344
Asp Gln Asp Ile Ala Gln Gly Asp Ala His Ile Ser Ser Glu Glu Gln
435                 440                 445 atc acc gag cca gca ttg cag cac tcc tac aca tta agg gat gtt gat          1392
Ile Thr Glu Pro Ala Leu Gln His Ser Tyr Thr Leu Arg Asp Val Asp
450                 455                 460 gag att gta ccg gta gag gag cct cca gtc tca aag gaa cct gaa aga          1440
Glu Ile Val Pro Val Glu Glu Pro Pro Val Ser Lys Glu Pro Glu Arg
465                 470                 475                 480 tgt gga tct gcc cgc agc ctt gct gat tgt ata tcc aca aac gag gag          1488
Cys Gly Ser Ala Arg Ser Leu Ala Asp Cys Ile Ser Thr Asn Glu Glu
                485                 490                 495 gag gaa tgg tca gca ctc gaa ggt gtg acg cgg gtc aat tcc ctc ttg          1536
Glu Glu Trp Ser Ala Leu Glu Gly Val Thr Arg Val Asn Ser Leu Leu
            500                 505                 510 aac ctt ccc aga ata ctt tca ggc gag aag aga tca acc agc tgg agg          1584
Asn Leu Pro Arg Ile Leu Ser Gly Glu Lys Arg Ser Thr Ser Trp Arg
515                 520                 525 aag cgg cga tga                                                          1596
Lys Arg Arg
    530

<210> SEQ ID NO 21
<211> LENGTH: 531
<212> TYPE: PRT
<213> ORGANISM: Oryza sativa

<400> SEQUENCE: 21
```

```
Met Gly Ser Cys Leu Ser Ser Asp Leu Pro Arg Ala Gly Ala Gly
1               5                   10                  15

Ala Gly Ala Ser Pro Gly Trp Pro Gln Arg Trp Arg Arg Arg Gln
            20                  25                  30

Arg Gly Val Glu Arg Gly Gly Ala Val Ser Gly Gly Gly Gly Val
            35                  40                  45

Phe Ser Ile Gly Val Gly Gly Lys Lys Leu His His Gly Gly Gly
        50                  55                  60

Gly Gly Glu Met Thr Glu Glu Leu Ala Lys Val Glu Gly Arg Val
65                  70                  75                  80

Cys Val Asn Gly Ala Ser Ala Ala Ala Cys Leu His Thr Gln Gln Gly
                85                  90                  95

Arg Lys Gly Thr Asn Gln Asp Ala Met Val Val Trp Glu Asn Phe Asn
                100                 105                 110

Thr Ser Asp Ser Val Phe Cys Gly Val Phe Asp Gly His Gly Pro Tyr
            115                 120                 125

Gly His Phe Val Ala Lys Lys Val Arg Asp Ser Leu Pro Val Lys Ile
        130                 135                 140

Arg Thr Leu Trp Lys Thr Ser Ala Asn Glu Asp Thr Ser Ser His Gln
145                 150                 155                 160

Asn Gly Ser Ile Ser Gly Ser Val Asn Ser Glu Ser Pro Val Val
                165                 170                 175

Asp Asp Glu Trp Gly Glu Tyr Ala Asp Ser Glu Lys Leu Pro Glu
            180                 185                 190

Met Phe Leu Pro Leu Lys Gln Ser Tyr Phe Lys Ala Phe Lys Leu Met
        195                 200                 205

Asp Lys Glu Leu Lys Met His Pro Thr Val Asp Cys Phe Cys Ser Gly
    210                 215                 220

Ser Thr Ala Val Thr Leu Val Lys Gln Gly Leu Asp Leu Val Val Gly
225                 230                 235                 240

Asn Leu Gly Asp Ser Arg Ala Ile Met Gly Thr Arg Asp Ala Ala Asn
                245                 250                 255

Asn Leu Thr Ala Val Gln Leu Thr Val Asp Leu Lys Pro Asn Leu Pro
        260                 265                 270

Arg Glu Ala Ala Arg Ile Gln Gln Cys Arg Gly Arg Val Phe Ala Leu
    275                 280                 285

Gln Asp Glu Pro Glu Val Ala Arg Val Trp Leu Pro Asn Asn Asp Ser
290                 295                 300

Pro Gly Leu Ala Met Ala Arg Ala Phe Gly Asp Phe Cys Leu Lys Asp
305                 310                 315                 320

Tyr Gly Leu Ile Ser Val Pro Gln Ile Ser Tyr Arg Arg Leu Thr Glu
                325                 330                 335

Lys Asp Glu Phe Ile Ile Leu Ala Thr Asp Gly Val Trp Asp Val Leu
            340                 345                 350

Ser Asn Lys Glu Ala Val Asp Ile Val Ala Ala Pro Ser Arg Ala
            355                 360                 365

Thr Ala Ala Arg Ala Leu Val Asp Cys Ala Val Arg Ser Trp Arg Leu
    370                 375                 380

Lys Phe Pro Thr Ser Lys Ser Asp Asp Cys Val Val Cys Leu Phe
385                 390                 395                 400

Leu Asp His Ala Lys Ser Pro Asp Leu Ile Gln Glu Asn Glu Ser Glu
            405                 410                 415

Glu Glu Thr Thr Glu Asp Val Ala Ile Pro Asp Thr Val Ala Lys Val
```

```
                420             425             430
Asp Gln Asp Ile Ala Gln Gly Asp Ala His Ile Ser Ser Glu Glu Gln
        435                 440                 445

Ile Thr Glu Pro Ala Leu Gln His Ser Tyr Thr Leu Arg Asp Val Asp
        450                 455                 460

Glu Ile Val Pro Val Glu Pro Pro Val Ser Lys Glu Pro Glu Arg
465                 470                 475                 480

Cys Gly Ser Ala Arg Ser Leu Ala Asp Cys Ile Ser Thr Asn Glu Glu
            485                 490                 495

Glu Glu Trp Ser Ala Leu Glu Gly Val Thr Arg Val Asn Ser Leu Leu
            500                 505                 510

Asn Leu Pro Arg Ile Leu Ser Gly Glu Lys Arg Ser Thr Ser Trp Arg
        515                 520                 525

Lys Arg Arg
        530

<210> SEQ ID NO 22
<211> LENGTH: 1170
<212> TYPE: DNA
<213> ORGANISM: Oryza sativa
<220> FEATURE:
<221> NAME/KEY: CDS
<222> LOCATION: (1)..(1170)

<400> SEQUENCE: 22 atg ggg atc tgt gca tct tca gag cag ctg gag cat gtt cat gag aca    48
Met Gly Ile Cys Ala Ser Ser Glu Gln Leu Glu His Val His Glu Thr
1               5                   10                  15 gat gag agc att gtg tat gtg aag gat gag caa gga agg ggg ggt agg    96
Asp Glu Ser Ile Val Tyr Val Lys Asp Glu Gln Gly Arg Gly Gly Arg
                20                  25                  30 ggg gtg gag agt ggg ggg gct agg aag gtg gcc tcc ctc ttc tcc cag   144
Gly Val Glu Ser Gly Gly Ala Arg Lys Val Ala Ser Leu Phe Ser Gln
            35                  40                  45 agg ggc aag aaa ggc ccc aac cag gac tct gtc atc ctc tgc cag gga   192
Arg Gly Lys Lys Gly Pro Asn Gln Asp Ser Val Ile Leu Cys Gln Gly
        50                  55                  60 ttc ggc atg gag gac ggc gtg ttc tgc ggc gtg ttc gac ggc cat ggc   240
Phe Gly Met Glu Asp Gly Val Phe Cys Gly Val Phe Asp Gly His Gly
65                  70                  75                  80 cgg tgc ggg caa ttc atc agc aag ctg gtg cgg gac tac ctc ccg ttc   288
Arg Cys Gly Gln Phe Ile Ser Lys Leu Val Arg Asp Tyr Leu Pro Phe
                85                  90                  95 atg atc ctg agc cac cgg aac gcg ctg ctc ctg gcc gac gcc gcc gcc   336
Met Ile Leu Ser His Arg Asn Ala Leu Leu Leu Ala Asp Ala Ala Ala
                100                 105                 110 gac gac gac gac gac gcc gcg ttc agc gac gac gcg gcg gcg tcg tcg   384
Asp Asp Asp Asp Asp Ala Ala Phe Ser Asp Asp Ala Ala Ala Ser Ser
            115                 120                 125 tcc gcg gac agc agc ggc aac tcg tcc ccg cag ccg tcg gcg tcg gcg   432
Ser Ala Asp Ser Ser Gly Asn Ser Ser Pro Gln Pro Ser Ala Ser Ala
        130                 135                 140 tcg gcg cag atg ctg gag gag tgg agg cag gcg tgc gcc agc gcg ttc   480
Ser Ala Gln Met Leu Glu Glu Trp Arg Gln Ala Cys Ala Ser Ala Phe
145                 150                 155                 160 gcc gcc atg gac ggc gag ctc aag ctc cag ccg aac ctc gac tgc gcg   528
Ala Ala Met Asp Gly Glu Leu Lys Leu Gln Pro Asn Leu Asp Cys Ala
                165                 170                 175 ttc agc ggc acg acg gcg gtg tgc gcc atc aag cag ggc agg gac ctc   576
```

```
                Phe Ser Gly Thr Thr Ala Val Cys Ala Ile Lys Gln Gly Arg Asp Leu
                                180                 185                 190 atc atc gcc aac ctc ggc gac tcg agg gcg gtg ctc gcc acc atg tcg        624
Ile Ile Ala Asn Leu Gly Asp Ser Arg Ala Val Leu Ala Thr Met Ser
            195                 200                 205 gac acc ggc tac ctc cag gcg gtg cag ctg acg gtg gac cac aag ccg        672
Asp Thr Gly Tyr Leu Gln Ala Val Gln Leu Thr Val Asp His Lys Pro
210                 215                 220 agc gtg ccg gag gag gcg gcg agg atc aag cgg agc ggg ggg agg gtg        720
Ser Val Pro Glu Glu Ala Ala Arg Ile Lys Arg Ser Gly Gly Arg Val
225                 230                 235                 240 ttc ggg ctg aag gac gag ccg ggg gtg atg cgg gtg tgg ctc ccc ggc        768
Phe Gly Leu Lys Asp Glu Pro Gly Val Met Arg Val Trp Leu Pro Gly
                245                 250                 255 gag aac tcg ccg ggg ctc gcc atg gcg agg tcg ctg ggc gac atg agg        816
Glu Asn Ser Pro Gly Leu Ala Met Ala Arg Ser Leu Gly Asp Met Arg
            260                 265                 270 ctg aag cgg cac ggc gtg atc ccg gcg ccg gag gtg acg tcg cgg cgc        864
Leu Lys Arg His Gly Val Ile Pro Ala Pro Glu Val Thr Ser Arg Arg
        275                 280                 285 gtg acg ggc gcc gac ctg ttc atg gtg ctc gcc acg gac ggg gtg tgg        912
Val Thr Gly Ala Asp Leu Phe Met Val Leu Ala Thr Asp Gly Val Trp
290                 295                 300 gac gtg ctg agc aac gag gag gtg gtg tcc atc gtg tgc gcg acg ccg        960
Asp Val Leu Ser Asn Glu Glu Val Val Ser Ile Val Cys Ala Thr Pro
305                 310                 315                 320 cgg aag cag cac gcg tcg aag gcg gtg gtg gag gcc gcc gtg cag cgg       1008
Arg Lys Gln His Ala Ser Lys Ala Val Val Glu Ala Ala Val Gln Arg
                325                 330                 335 tgg cgg gcc aag ttc ccg acg tcc agg gtg gac gac tgc tcc gcc gtc       1056
Trp Arg Ala Lys Phe Pro Thr Ser Arg Val Asp Asp Cys Ser Ala Val
            340                 345                 350 tgc ctc ttc ctc cac gac cac acc ctc ggc acg gcc gcc gcc gcc tcc       1104
Cys Leu Phe Leu His Asp His Thr Leu Gly Thr Ala Ala Ala Ala Ser
        355                 360                 365 gcc gca gcc gcc gcg gcc gcc aga aag gcg cgc agg gcc tcc acc gcc       1152
Ala Ala Ala Ala Ala Ala Ala Arg Lys Ala Arg Arg Ala Ser Thr Ala
370                 375                 380 acg ccg ccg gcg agc tga                                                1170
Thr Pro Pro Ala Ser
385
```

<210> SEQ ID NO 23
<211> LENGTH: 389
<212> TYPE: PRT
<213> ORGANISM: Oryza sativa

<400> SEQUENCE: 23

```
Met Gly Ile Cys Ala Ser Ser Glu Gln Leu Glu His Val His Glu Thr
1               5                   10                  15

Asp Glu Ser Ile Val Tyr Val Lys Asp Glu Gln Gly Arg Gly Arg
            20                  25                  30

Gly Val Glu Ser Gly Gly Ala Arg Lys Val Ala Ser Leu Phe Ser Gln
        35                  40                  45

Arg Gly Lys Lys Gly Pro Asn Gln Asp Ser Val Ile Leu Cys Gln Gly
    50                  55                  60

Phe Gly Met Glu Asp Gly Val Phe Cys Gly Val Phe Asp Gly His Gly
65                  70                  75                  80

Arg Cys Gly Gln Phe Ile Ser Lys Leu Val Arg Asp Tyr Leu Pro Phe
```

```
                85                  90                  95
Met Ile Leu Ser His Arg Asn Ala Leu Leu Ala Asp Ala Ala
            100                 105                 110

Asp Asp Asp Asp Ala Ala Phe Ser Asp Ala Ala Ser Ser
        115                 120                 125

Ser Ala Asp Ser Ser Gly Asn Ser Ser Pro Gln Pro Ser Ala Ser Ala
    130                 135                 140

Ser Ala Gln Met Leu Glu Glu Trp Arg Gln Ala Cys Ala Ser Ala Phe
145                 150                 155                 160

Ala Ala Met Asp Gly Glu Leu Lys Leu Gln Pro Asn Leu Asp Cys Ala
                165                 170                 175

Phe Ser Gly Thr Thr Ala Val Cys Ala Ile Lys Gln Gly Arg Asp Leu
            180                 185                 190

Ile Ile Ala Asn Leu Gly Asp Ser Arg Ala Val Leu Ala Thr Met Ser
                195                 200                 205

Asp Thr Gly Tyr Leu Gln Ala Val Gln Leu Thr Val Asp His Lys Pro
            210                 215                 220

Ser Val Pro Glu Glu Ala Ala Arg Ile Lys Arg Ser Gly Gly Arg Val
225                 230                 235                 240

Phe Gly Leu Lys Asp Glu Pro Gly Val Met Arg Val Trp Leu Pro Gly
                245                 250                 255

Glu Asn Ser Pro Gly Leu Ala Met Ala Arg Ser Leu Gly Asp Met Arg
                260                 265                 270

Leu Lys Arg His Gly Val Ile Pro Ala Pro Glu Val Thr Ser Arg Arg
            275                 280                 285

Val Thr Gly Ala Asp Leu Phe Met Val Leu Ala Thr Asp Gly Val Trp
        290                 295                 300

Asp Val Leu Ser Asn Glu Glu Val Val Ser Ile Val Cys Ala Thr Pro
305                 310                 315                 320

Arg Lys Gln His Ala Ser Lys Ala Val Val Glu Ala Val Gln Arg
                325                 330                 335

Trp Arg Ala Lys Phe Pro Thr Ser Arg Val Asp Asp Cys Ser Ala Val
                340                 345                 350

Cys Leu Phe Leu His Asp His Thr Leu Gly Thr Ala Ala Ala Ala Ser
            355                 360                 365

Ala Ala Ala Ala Ala Ala Arg Lys Ala Arg Arg Ala Ser Thr Ala
        370                 375                 380

Thr Pro Pro Ala Ser
385

<210> SEQ ID NO 24
<211> LENGTH: 25
<212> TYPE: DNA
<213> ORGANISM: Artificial
<220> FEATURE:
<223> OTHER INFORMATION: Synthetic DNA

<400> SEQUENCE: 24
tgctttcgcc attaaatagc gacgg                                         25

<210> SEQ ID NO 25
<211> LENGTH: 23
<212> TYPE: DNA
<213> ORGANISM: Artificial
<220> FEATURE:
<223> OTHER INFORMATION: Synthetic DNA
```

```
<400> SEQUENCE: 25
cgctgcggac atctacattt ttg                                             23

<210> SEQ ID NO 26
<211> LENGTH: 22
<212> TYPE: DNA
<213> ORGANISM: Artificial
<220> FEATURE:
<223> OTHER INFORMATION: Synthetic DNA

<400> SEQUENCE: 26
tcccggacat gaagccattt ac                                              22

<210> SEQ ID NO 27
<211> LENGTH: 16
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 27
ngtcgaswga nawgaa                                                     16

<210> SEQ ID NO 28
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 28
taaccttacg ctttgctcgg tcccagacgc aagattacat ctctttctat ggnttgagat     60
cgnacggacg gctgtttgag gacggtccaa ttgccactag ccagatttac gtgcatagca    120
agttaatgat tgttgatgac cggatcgcag tgatcggatc ttctaatata aacgatagga    180
gcttactagg ttcacgagac tctgaggtac tttcaaaaat ccaattcatt ctttattgca    240
gcaaaacaga gttatgtatt catttgaatc aatcatgttt cagatcggtg ttgtgattga    300
agacaaagaa ttcgtggaat cttcgatgaa cggaatgaag tggatggccg ggaagttctc    360
ttacagtctt agatgttcct tgtggtcaga gcatctcggc cttcacgccg gagaggtaat    420
tttaaaaaat ttctagaaac gcctactact atacatttt gacttcagaa acctttattt     480
tcatctcact cgaccaaa                                                  498

<210> SEQ ID NO 29
<211> LENGTH: 39
<212> TYPE: DNA
<213> ORGANISM: Artificial
<220> FEATURE:
<223> OTHER INFORMATION: Synthetic DNA

<400> SEQUENCE: 29
```

```
acgcgtcgac atgggacatt tctcttccat gttcaacgg                                39
```

<210> SEQ ID NO 30
<211> LENGTH: 43
<212> TYPE: DNA
<213> ORGANISM: Artificial
<220> FEATURE:
<223> OTHER INFORMATION: Synthetic DNA

<400> SEQUENCE: 30

```
tgtacatgta cactatagag atggcgacga cgatgaagaa tgg                           43
```

<210> SEQ ID NO 31
<211> LENGTH: 1176
<212> TYPE: DNA
<213> ORGANISM: Arabidopsis thaliana
<220> FEATURE:
<221> NAME/KEY: CDS
<222> LOCATION: (1)..(1176)

<400> SEQUENCE: 31

| | | | | | | | | | | | | | | | | |
|---|---|---|---|---|---|---|---|---|---|---|---|---|---|---|---|---|
| atg | gcg | tct | gct | agc | ttc | gtt | aag | cct | aac | acc | ctc | tct | tct | cca | tgg | 48 |
| Met | Ala | Ser | Ala | Ser | Phe | Val | Lys | Pro | Asn | Thr | Leu | Ser | Ser | Pro | Trp | |
| 1 | | | | 5 | | | | | 10 | | | | | 15 | | |

| atc | ggc | caa | cgc | tcc | ttt | gct | cac | acc | tct | gct | tct | tct | tct | cct | cct | 96 |
|---|---|---|---|---|---|---|---|---|---|---|---|---|---|---|---|---|
| Ile | Gly | Gln | Arg | Ser | Phe | Ala | His | Thr | Ser | Ala | Ser | Ser | Ser | Pro | Pro | |
| | | | 20 | | | | | 25 | | | | | 30 | | | |

| cct | cga | gtc | tcc | ttc | gcg | atc | cgc | gcc | ggt | gct | tac | tcc | gac | gag | ctt | 144 |
|---|---|---|---|---|---|---|---|---|---|---|---|---|---|---|---|---|
| Pro | Arg | Val | Ser | Phe | Ala | Ile | Arg | Ala | Gly | Ala | Tyr | Ser | Asp | Glu | Leu | |
| | | 35 | | | | | 40 | | | | | 45 | | | | |

| gtt | aaa | acc | gcc | aaa | agc | att | gca | tcc | cct | ggg | aga | ggt | atc | ttg | gcg | 192 |
|---|---|---|---|---|---|---|---|---|---|---|---|---|---|---|---|---|
| Val | Lys | Thr | Ala | Lys | Ser | Ile | Ala | Ser | Pro | Gly | Arg | Gly | Ile | Leu | Ala | |
| 50 | | | | | 55 | | | | | 60 | | | | | | |

| atc | gat | gag | tcc | aat | gca | acc | tgt | ggg | aag | agg | ctt | gct | tct | atc | ggc | 240 |
|---|---|---|---|---|---|---|---|---|---|---|---|---|---|---|---|---|
| Ile | Asp | Glu | Ser | Asn | Ala | Thr | Cys | Gly | Lys | Arg | Leu | Ala | Ser | Ile | Gly | |
| 65 | | | | | 70 | | | | | 75 | | | | | 80 | |

| ttg | gat | aac | acc | gag | gac | aac | cgt | cag | gcc | tac | agg | caa | ctt | ctg | ctt | 288 |
|---|---|---|---|---|---|---|---|---|---|---|---|---|---|---|---|---|
| Leu | Asp | Asn | Thr | Glu | Asp | Asn | Arg | Gln | Ala | Tyr | Arg | Gln | Leu | Leu | Leu | |
| | | | | 85 | | | | | 90 | | | | | 95 | | |

| acc | act | cct | ggc | ctc | ggc | gat | tac | atc | tct | ggt | tcc | att | ctc | ttc | gag | 336 |
|---|---|---|---|---|---|---|---|---|---|---|---|---|---|---|---|---|
| Thr | Thr | Pro | Gly | Leu | Gly | Asp | Tyr | Ile | Ser | Gly | Ser | Ile | Leu | Phe | Glu | |
| | | | 100 | | | | | 105 | | | | | 110 | | | |

| gag | act | ctt | tac | cag | tcc | acc | aag | gac | ggt | aag | acc | ttt | gtc | gat | tgc | 384 |
|---|---|---|---|---|---|---|---|---|---|---|---|---|---|---|---|---|
| Glu | Thr | Leu | Tyr | Gln | Ser | Thr | Lys | Asp | Gly | Lys | Thr | Phe | Val | Asp | Cys | |
| | | 115 | | | | | 120 | | | | | 125 | | | | |

| ttg | cgc | gat | gcc | aac | atc | gtc | cct | ggc | atc | aaa | gtt | gac | aag | ggc | ttg | 432 |
|---|---|---|---|---|---|---|---|---|---|---|---|---|---|---|---|---|
| Leu | Arg | Asp | Ala | Asn | Ile | Val | Pro | Gly | Ile | Lys | Val | Asp | Lys | Gly | Leu | |
| | 130 | | | | | 135 | | | | | 140 | | | | | |

| tct | ccc | cta | gcc | ggt | tcc | aac | gaa | gag | tct | tgg | tgc | caa | ggc | ttg | gat | 480 |
|---|---|---|---|---|---|---|---|---|---|---|---|---|---|---|---|---|
| Ser | Pro | Leu | Ala | Gly | Ser | Asn | Glu | Glu | Ser | Trp | Cys | Gln | Gly | Leu | Asp | |
| 145 | | | | | 150 | | | | | 155 | | | | | 160 | |

| gga | ttg | gcc | tca | cgc | tct | gct | gag | tac | tac | aag | caa | ggc | gct | cgt | ttt | 528 |
|---|---|---|---|---|---|---|---|---|---|---|---|---|---|---|---|---|
| Gly | Leu | Ala | Ser | Arg | Ser | Ala | Glu | Tyr | Tyr | Lys | Gln | Gly | Ala | Arg | Phe | |
| | | | | 165 | | | | | 170 | | | | | 175 | | |

| gcc | aag | tgg | agg | aca | gtg | gtg | agt | gtt | ccc | tgc | ggt | cct | tca | gca | ctg | 576 |
|---|---|---|---|---|---|---|---|---|---|---|---|---|---|---|---|---|
| Ala | Lys | Trp | Arg | Thr | Val | Val | Ser | Val | Pro | Cys | Gly | Pro | Ser | Ala | Leu | |
| | | | 180 | | | | | 185 | | | | | 190 | | | |

| gct | gtg | aag | gaa | gct | gcg | tgg | ggg | ctg | gct | cgc | tat | gca | gcc | atc | tct | 624 |
|---|---|---|---|---|---|---|---|---|---|---|---|---|---|---|---|---|
| Ala | Val | Lys | Glu | Ala | Ala | Trp | Gly | Leu | Ala | Arg | Tyr | Ala | Ala | Ile | Ser | |
| | | 195 | | | | | 200 | | | | | 205 | | | | |

| cag | gat | aat | ggt | ctt | gtc | ccc | att | gtg | gag | cca | gag | atc | ctt | ctg | gac | 672 |

```
Gln Asp Asn Gly Leu Val Pro Ile Val Glu Pro Glu Ile Leu Leu Asp
    210                 215                 220 ggg gac cac cca ata gag agg act ctg gag gtg gca gag aaa gtg tgg      720
Gly Asp His Pro Ile Glu Arg Thr Leu Glu Val Ala Glu Lys Val Trp
225                 230                 235                 240 tca gag gtg ttc ttc tac ttg gca cag aac aac gtc atg ttt gag ggc      768
Ser Glu Val Phe Phe Tyr Leu Ala Gln Asn Asn Val Met Phe Glu Gly
                245                 250                 255 att ctg ttg aag ccg agc atg gtc acc cca ggc gct gag cac aag aac      816
Ile Leu Leu Lys Pro Ser Met Val Thr Pro Gly Ala Glu His Lys Asn
            260                 265                 270 aag gcc tct ccc gag acc gtt gca gat ttc acg ctc acc atg ctg aaa      864
Lys Ala Ser Pro Glu Thr Val Ala Asp Phe Thr Leu Thr Met Leu Lys
        275                 280                 285 agg agg gtt cct ccg gct gtc cca ggg atc atg ttt ctg tca gga gga      912
Arg Arg Val Pro Pro Ala Val Pro Gly Ile Met Phe Leu Ser Gly Gly
    290                 295                 300 caa tca gag gca gag gcc aca ctg aac ctg aac gcc atg aac cag agc      960
Gln Ser Glu Ala Glu Ala Thr Leu Asn Leu Asn Ala Met Asn Gln Ser
305                 310                 315                 320 cca aac cca tgg cat gtg tcc ttc tca tac gca cgt gcc ctg cag aac     1008
Pro Asn Pro Trp His Val Ser Phe Ser Tyr Ala Arg Ala Leu Gln Asn
                325                 330                 335 tcc gtg ctc aga aca tgg caa ggc aag ccg gag aag att gag gcc tcg     1056
Ser Val Leu Arg Thr Trp Gln Gly Lys Pro Glu Lys Ile Glu Ala Ser
            340                 345                 350 cag aag gca ctg ttg gtg agg gca aag gcc aac tca ctg gcc cag ctc     1104
Gln Lys Ala Leu Leu Val Arg Ala Lys Ala Asn Ser Leu Ala Gln Leu
        355                 360                 365 ggc aaa tac tca gcc gag gga gag aac gag gat gcc aag aaa gga atg     1152
Gly Lys Tyr Ser Ala Glu Gly Glu Asn Glu Asp Ala Lys Lys Gly Met
    370                 375                 380 ttt gtc aag ggt tac acc tac tga                                     1176
Phe Val Lys Gly Tyr Thr Tyr
385                 390

<210> SEQ ID NO 32
<211> LENGTH: 391
<212> TYPE: PRT
<213> ORGANISM: Arabidopsis thaliana

<400> SEQUENCE: 32

Met Ala Ser Ala Ser Phe Val Lys Pro Asn Thr Leu Ser Ser Pro Trp
1               5                   10                  15

Ile Gly Gln Arg Ser Phe Ala His Thr Ser Ala Ser Ser Pro Pro
                20                  25                  30

Pro Arg Val Ser Phe Ala Ile Arg Ala Gly Ala Tyr Ser Asp Glu Leu
            35                  40                  45

Val Lys Thr Ala Lys Ser Ile Ala Ser Pro Gly Arg Gly Ile Leu Ala
        50                  55                  60

Ile Asp Glu Ser Asn Ala Thr Cys Gly Lys Arg Leu Ala Ser Ile Gly
65                  70                  75                  80

Leu Asp Asn Thr Glu Asp Asn Arg Gln Ala Tyr Arg Gln Leu Leu Leu
                85                  90                  95

Thr Thr Pro Gly Leu Gly Asp Tyr Ile Ser Gly Ser Ile Leu Phe Glu
            100                 105                 110

Glu Thr Leu Tyr Gln Ser Thr Lys Asp Gly Lys Thr Phe Val Asp Cys
        115                 120                 125
```

-continued

```
Leu Arg Asp Ala Asn Ile Val Pro Gly Ile Lys Val Asp Lys Gly Leu
    130                 135                 140

Ser Pro Leu Ala Gly Ser Asn Glu Glu Ser Trp Cys Gln Gly Leu Asp
145                 150                 155                 160

Gly Leu Ala Ser Arg Ser Ala Glu Tyr Tyr Lys Gln Gly Ala Arg Phe
                165                 170                 175

Ala Lys Trp Arg Thr Val Val Ser Val Pro Cys Gly Pro Ser Ala Leu
            180                 185                 190

Ala Val Lys Glu Ala Ala Trp Gly Leu Ala Arg Tyr Ala Ala Ile Ser
        195                 200                 205

Gln Asp Asn Gly Leu Val Pro Ile Val Glu Pro Glu Ile Leu Leu Asp
210                 215                 220

Gly Asp His Pro Ile Glu Arg Thr Leu Glu Val Ala Glu Lys Val Trp
225                 230                 235                 240

Ser Glu Val Phe Phe Tyr Leu Ala Gln Asn Asn Val Met Phe Glu Gly
                245                 250                 255

Ile Leu Leu Lys Pro Ser Met Val Thr Pro Gly Ala Glu His Lys Asn
            260                 265                 270

Lys Ala Ser Pro Glu Thr Val Ala Asp Phe Thr Leu Thr Met Leu Lys
        275                 280                 285

Arg Arg Val Pro Pro Ala Val Pro Gly Ile Met Phe Leu Ser Gly Gly
290                 295                 300

Gln Ser Glu Ala Glu Ala Thr Leu Asn Leu Asn Ala Met Asn Gln Ser
305                 310                 315                 320

Pro Asn Pro Trp His Val Ser Phe Ser Tyr Ala Arg Ala Leu Gln Asn
                325                 330                 335

Ser Val Leu Arg Thr Trp Gln Gly Lys Pro Glu Lys Ile Glu Ala Ser
            340                 345                 350

Gln Lys Ala Leu Leu Val Arg Ala Lys Ala Asn Ser Leu Ala Gln Leu
        355                 360                 365

Gly Lys Tyr Ser Ala Glu Gly Glu Asn Glu Asp Ala Lys Lys Gly Met
370                 375                 380

Phe Val Lys Gly Tyr Thr Tyr
385                 390

<210> SEQ ID NO 33
<211> LENGTH: 393
<212> TYPE: PRT
<213> ORGANISM: Picea sitchensis

<400> SEQUENCE: 33

Met Ala Ala Ser Val Leu Lys Ala Gly Val Arg Leu Gly Ser Ser Gln
1               5                   10                  15

Trp Thr Gly Gln Ser Leu Thr Gln Asn Ile Asp Ser His Lys Gln Pro
                20                  25                  30

Lys Ala Gln Arg Val Ser Met Pro Ile Arg Ala Gly Ser Tyr Ala Glu
            35                  40                  45

Glu Leu Val Gln Thr Ala Lys Thr Val Ala Ser Pro Gly Arg Gly Ile
        50                  55                  60

Leu Ala Ile Asp Glu Ser Asn Ala Thr Cys Gly Lys Arg Leu Ala Ser
65                  70                  75                  80

Ile Gly Leu Glu Asn Asn Glu Thr Asn Arg Gln Ala Tyr Arg Gln Leu
                85                  90                  95

Leu Leu Thr Thr Pro Gly Leu Gly Glu Tyr Ile Ser Gly Ser Ile Leu
            100                 105                 110
```

Phe Glu Glu Thr Leu Tyr Gln Ser Thr Thr Asp Gly Arg Lys Phe Val
            115                 120                 125

Asp Cys Leu Arg Glu Gln Asn Ile Met Pro Gly Ile Lys Val Asp Lys
        130                 135                 140

Gly Leu Val Pro Leu Pro Gly Ser Asn Asn Glu Ser Trp Cys Gln Gly
145                 150                 155                 160

Leu Asp Gly Leu Ala Ser Arg Ser Ala Glu Tyr Tyr Lys Gln Gly Ala
                165                 170                 175

Arg Phe Ala Lys Trp Arg Thr Val Val Ser Ile Pro Asn Gly Pro Ser
            180                 185                 190

Asp Leu Ala Val Lys Glu Ala Ala Trp Gly Leu Ala Arg Tyr Ala Ala
        195                 200                 205

Ile Ser Gln Asp Asn Gly Leu Val Pro Ile Val Glu Pro Glu Ile Leu
    210                 215                 220

Leu Asp Gly Asp His Ser Ile Asp Arg Thr Leu Glu Val Ala Glu Lys
225                 230                 235                 240

Val Trp Ala Glu Val Phe Phe Tyr Leu Ala Glu Asn Asn Val Phe Phe
                245                 250                 255

Glu Gly Ile Leu Leu Lys Pro Ser Met Val Thr Pro Gly Ala Glu His
            260                 265                 270

Lys Glu Lys Ala Thr Pro Gln Gln Val Ala Asp Tyr Thr Leu Lys Met
        275                 280                 285

Leu Lys Arg Arg Val Pro Pro Ala Val Pro Gly Ile Met Phe Leu Ser
    290                 295                 300

Gly Gly Gln Ser Glu Val Glu Ala Thr Leu Asn Leu Asn Ala Met Asn
305                 310                 315                 320

Gln Ser Pro Asn Pro Trp His Val Ser Phe Ser Tyr Ala Arg Ala Leu
                325                 330                 335

Gln Asn Thr Ser Leu Lys Thr Trp Lys Gly Leu Pro Glu Asn Ile Glu
            340                 345                 350

Ala Ala Gln Arg Ala Leu Leu Ile Arg Ala Lys Ala Asn Ser Leu Ala
        355                 360                 365

Gln Leu Gly Arg Tyr Ser Ala Glu Gly Glu Ser Glu Ser Lys Lys
    370                 375                 380

Gly Met Phe Val Lys Gly Tyr Thr Tyr
385                 390

<210> SEQ ID NO 34
<211> LENGTH: 393
<212> TYPE: PRT
<213> ORGANISM: Picea sitchensis

<400> SEQUENCE: 34

Met Ala Ala Ser Val Leu Lys Ala Gly Val Arg Leu Gly Ser Ser Gln
1               5                   10                  15

Trp Thr Gly Gln Ser Leu Thr Gln Asn Ile Asp Ser His Lys Gln Pro
            20                  25                  30

Lys Ala Gln Arg Val Ser Met Pro Ile Arg Ala Gly Ser Tyr Ala Glu
        35                  40                  45

Glu Leu Val Gln Thr Ala Lys Thr Val Ala Ser Pro Gly Arg Gly Ile
    50                  55                  60

Leu Ala Ile Asp Glu Ser Asn Ala Thr Cys Gly Lys Arg Leu Ala Ser
65                  70                  75                  80

Ile Gly Leu Glu Asn Asn Glu Thr Asn Arg Gln Ala Tyr Arg Gln Leu

```
                    85                  90                  95
Leu Leu Thr Thr Pro Gly Leu Gly Glu Tyr Ile Ser Gly Ser Ile Leu
            100                 105                 110

Phe Glu Glu Thr Leu Tyr Gln Ser Thr Thr Asp Gly Arg Lys Phe Val
            115                 120                 125

Asp Cys Leu Arg Glu Gln Asn Ile Met Pro Gly Ile Lys Val Asp Lys
130                 135                 140

Gly Leu Val Pro Leu Pro Gly Ser Asn Glu Ser Trp Cys Gln Gly
145                 150                 155                 160

Leu Asp Gly Leu Ala Ser Arg Ser Ala Glu Tyr Tyr Lys Gln Gly Ala
            165                 170                 175

Arg Phe Ala Lys Trp Arg Thr Val Val Ser Ile Pro Asn Gly Pro Ser
            180                 185                 190

Asp Leu Ala Val Lys Glu Ala Ala Trp Gly Leu Ala Arg Tyr Ala Ala
            195                 200                 205

Ile Ser Gln Asp Asn Gly Leu Val Pro Ile Val Glu Pro Glu Ile Leu
            210                 215                 220

Leu Asp Gly Asp His Ser Ile Asp Arg Thr Leu Glu Val Ala Glu Lys
225                 230                 235                 240

Val Trp Ala Glu Val Phe Phe Tyr Leu Ala Glu Asn Asn Val Phe Phe
            245                 250                 255

Glu Gly Ile Leu Leu Lys Pro Ser Met Val Thr Pro Gly Ala Glu His
            260                 265                 270

Lys Glu Lys Ala Thr Pro Gln Gln Val Ala Asp Tyr Thr Leu Lys Met
            275                 280                 285

Leu Lys Arg Arg Val Pro Pro Ala Val Pro Gly Ile Met Phe Leu Ser
            290                 295                 300

Gly Gly Gln Tyr Glu Val Glu Ala Thr Leu Asn Leu Asn Ala Met Asn
305                 310                 315                 320

Gln Ser Pro Asn Pro Trp His Val Ser Phe Ser Tyr Ala Arg Ala Leu
            325                 330                 335

Gln Asn Thr Ser Leu Lys Thr Trp Lys Gly Leu Pro Glu Asn Ile Glu
            340                 345                 350

Ala Ala Gln Arg Ala Leu Leu Ile Arg Ala Lys Ala Asn Ser Leu Ala
            355                 360                 365

Gln Leu Gly Arg Tyr Ser Ala Glu Gly Glu Ser Glu Ser Lys Lys
            370                 375                 380

Gly Met Phe Val Lys Gly Tyr Thr Tyr
385                 390

<210> SEQ ID NO 35
<211> LENGTH: 393
<212> TYPE: PRT
<213> ORGANISM: Picea sitchensis

<400> SEQUENCE: 35

Met Ala Ala Ser Val Ile Lys Ala Gly Val Arg Leu Gly Ser Ser Gln
1               5                   10                  15

Trp Thr Gly Gln Ser Leu Thr Gln Asn Ile Asp Ser His Lys Gln Pro
            20                  25                  30

Lys Ala Gln Arg Val Ser Met Pro Ile Arg Ala Gly Ser Tyr Ala Glu
            35                  40                  45

Glu Leu Val Gln Thr Ala Lys Thr Val Ala Ser Pro Gly Arg Gly Ile
            50                  55                  60
```

-continued

```
Leu Ala Ile Asp Glu Ser Asn Ala Thr Cys Gly Lys Arg Leu Ala Ser
 65                  70                  75                  80

Ile Gly Leu Glu Asn Asn Glu Thr Asn Arg Gln Ala Tyr Arg Gln Leu
                 85                  90                  95

Leu Leu Thr Thr Pro Gly Leu Gly Tyr Ile Ser Gly Ser Ile Leu
            100                 105                 110

Phe Glu Glu Thr Leu Tyr Gln Ser Thr Thr Asp Gly Arg Lys Phe Val
            115                 120                 125

Asp Cys Leu Arg Glu Gln Asn Ile Met Pro Gly Ile Lys Val Asp Lys
        130                 135                 140

Gly Leu Val Pro Leu Pro Gly Ser Asn Glu Ser Trp Cys Gln Gly
145                 150                 155                 160

Leu Asp Gly Leu Ala Ser Arg Ser Ala Glu Tyr Tyr Lys Gln Gly Ala
                165                 170                 175

Arg Phe Ala Lys Trp Arg Thr Val Val Ser Ile Pro Asn Gly Pro Ser
            180                 185                 190

Asp Leu Ala Val Lys Glu Ala Ala Trp Gly Leu Ala Arg Tyr Ala Ala
        195                 200                 205

Ile Ser Gln Asp Asn Gly Leu Val Pro Ile Val Glu Pro Glu Ile Leu
210                 215                 220

Leu Asp Gly Asp His Ser Ile Asp Arg Thr Leu Glu Val Ala Glu Lys
225                 230                 235                 240

Val Trp Ala Glu Val Phe Phe Tyr Leu Ala Glu Asn Asn Val Leu Phe
                245                 250                 255

Glu Gly Ile Leu Leu Lys Pro Ser Met Val Thr Pro Gly Ala Glu His
            260                 265                 270

Lys Glu Lys Ala Thr Pro Gln Gln Val Ala Asp Tyr Thr Leu Lys Met
        275                 280                 285

Leu Lys Arg Arg Val Pro Pro Ala Val Pro Gly Ile Met Phe Leu Ser
        290                 295                 300

Gly Gly Gln Ser Glu Val Glu Ala Thr Leu Asn Leu Asn Ala Met Asn
305                 310                 315                 320

Gln Ser Pro Asn Pro Trp His Val Ser Phe Ser Tyr Ala Arg Ala Leu
                325                 330                 335

Gln Asn Thr Ser Leu Lys Thr Trp Lys Gly Leu Pro Glu Asn Ile Glu
            340                 345                 350

Ala Ala Gln Arg Ala Leu Leu Ile Arg Ala Lys Ala Asn Ser Leu Ala
        355                 360                 365

Gln Leu Gly Arg Tyr Ser Ala Glu Gly Glu Ser Glu Ser Lys Lys
        370                 375                 380

Gly Met Phe Val Lys Gly Tyr Thr Tyr
385                 390

<210> SEQ ID NO 36
<211> LENGTH: 391
<212> TYPE: PRT
<213> ORGANISM: Populus trichocarpa

<400> SEQUENCE: 36

Met Ala Cys Ala Asn Leu Val Lys Leu Asn Ala Ser Ser Ser Trp
  1               5                  10                  15

Ile Gly Gln Lys Ser Pro Phe Gly Gln Arg Ser Gln Gly Ser Ser Thr
                 20                  25                  30

Arg Arg Val Ser Phe Ser Ile Arg Ala Asn Ser Tyr Thr Asp Glu Leu
             35                  40                  45
```

Val Gln Thr Ala Lys Thr Ile Ala Ser Pro Gly Arg Gly Ile Leu Ala
    50                  55                  60

Ile Asp Glu Ser Asn Ala Thr Cys Gly Lys Arg Leu Ala Ser Ile Gly
65                  70                  75                  80

Leu Asp Asn Thr Glu Thr Asn Arg Gln Ala Tyr Arg Gln Leu Leu Leu
                85                  90                  95

Thr Thr Pro Ser Leu Gly Glu Tyr Ile Ser Gly Ala Ile Leu Phe Glu
            100                 105                 110

Glu Thr Leu Tyr Gln Ser Thr Thr Asp Gly Lys Lys Phe Val Asp Cys
        115                 120                 125

Leu Arg Asp Glu Asn Ile Val Pro Gly Ile Lys Val Asp Lys Gly Leu
    130                 135                 140

Val Pro Leu Pro Gly Ser Asn Asn Glu Ser Trp Cys Gln Gly Leu Asp
145                 150                 155                 160

Gly Leu Ala Ser Arg Ser Ala Glu Tyr Tyr Lys Gln Gly Ala Arg Phe
                165                 170                 175

Ala Lys Trp Arg Thr Val Val Ser Ile Pro Cys Gly Pro Ser Ala Leu
            180                 185                 190

Ala Val Lys Glu Ala Ala Trp Gly Leu Ala Arg Tyr Ala Ala Ile Ser
        195                 200                 205

Gln Asp Asn Gly Leu Val Pro Ile Val Glu Pro Glu Ile Leu Leu Asp
    210                 215                 220

Gly Asp His Pro Ile Asp Arg Thr Leu Glu Val Ala Glu Lys Val Trp
225                 230                 235                 240

Ser Glu Val Phe Tyr Tyr Leu Ala Glu Asn Asn Val Val Phe Glu Gly
                245                 250                 255

Ile Leu Leu Lys Pro Ser Met Val Thr Pro Gly Ala Glu His Lys Glu
            260                 265                 270

Lys Ala Ser Ala Asp Thr Ile Ala Lys Tyr Thr Leu Thr Met Leu Lys
        275                 280                 285

Arg Arg Val Pro Pro Ala Val Pro Gly Ile Met Phe Leu Ser Gly Gly
    290                 295                 300

Gln Ser Glu Val Gln Ala Thr Leu Asn Leu Asn Ala Met Asn Gln Ser
305                 310                 315                 320

Pro Asn Pro Trp His Val Ser Phe Ser Tyr Ala Arg Ala Leu Gln Asn
                325                 330                 335

Thr Val Leu Lys Thr Trp Gln Gly Arg Pro Asp Asn Val Glu Ala Ala
            340                 345                 350

Gln Lys Ser Leu Leu Val Arg Ala Lys Ala Asn Ser Leu Ala Gln Leu
        355                 360                 365

Gly Arg Tyr Ser Ala Glu Gly Glu Ser Glu Ala Thr Lys Gly Met
    370                 375                 380

Phe Val Lys Gly Tyr Thr Tyr
385                 390

<210> SEQ ID NO 37
<211> LENGTH: 391
<212> TYPE: PRT
<213> ORGANISM: Populus trichocarpa

<400> SEQUENCE: 37

Met Ala Cys Ala Asn Leu Val Lys Leu Asn Ala Ala Ser Ser Ser Trp
1               5                   10                  15

Ile Gly Gln Lys Ser Pro Phe Gly Gln Arg Ser Gln Gly Ser Ser Thr

```
                20                  25                  30
Arg Arg Val Ser Phe Ser Ile Arg Ala Asn Ser Tyr Thr Asp Glu Leu
            35                  40                  45
Val Gln Thr Ala Lys Thr Ile Ala Ser Pro Gly Arg Gly Ile Leu Ala
50                  55                  60
Ile Asp Glu Ser Asn Ala Thr Cys Gly Lys Arg Leu Ala Ser Ile Gly
65                  70                  75                  80
Leu Asp Asn Thr Glu Thr Asn Arg Gln Ala Tyr Arg Gln Leu Leu Leu
                85                  90                  95
Thr Thr Pro Ser Leu Gly Glu Tyr Ile Ser Gly Ala Ile Leu Phe Glu
            100                 105                 110
Glu Thr Leu Tyr Gln Ser Thr Thr Asp Gly Lys Lys Phe Val Asp Cys
            115                 120                 125
Leu Arg Asp Glu Asn Ile Val Pro Gly Ile Lys Val Asp Lys Gly Leu
            130                 135                 140
Val Pro Leu Pro Gly Ser Asn Asn Glu Ser Trp Cys Gln Gly Leu Asp
145                 150                 155                 160
Gly Leu Ala Ser Arg Ser Ala Glu Tyr Tyr Lys Gln Gly Ala Arg Phe
                165                 170                 175
Ala Lys Trp Arg Thr Val Val Ser Ile Pro Cys Gly Pro Ser Ala Leu
            180                 185                 190
Ala Val Lys Glu Ala Ala Trp Gly Leu Ala Arg Tyr Ala Ala Ile Ser
            195                 200                 205
Gln Asp Asn Gly Leu Val Pro Ile Val Glu Pro Glu Ile Leu Leu Asp
            210                 215                 220
Gly Asp His Pro Ile Asp Arg Thr Leu Glu Val Ala Glu Lys Val Trp
225                 230                 235                 240
Ser Gly Val Phe Tyr Tyr Leu Ala Glu Asn Asn Val Val Phe Glu Gly
                245                 250                 255
Ile Leu Leu Lys Pro Ser Met Val Thr Pro Gly Ala Glu His Lys Glu
            260                 265                 270
Lys Ala Ser Ala Asp Thr Ile Ala Lys Tyr Thr Leu Thr Met Leu Lys
            275                 280                 285
Arg Arg Val Pro Pro Ala Val Pro Gly Ile Met Phe Leu Ser Gly Gly
            290                 295                 300
Gln Ser Glu Val Gln Ala Thr Leu Asn Leu Asn Ala Met Asn Gln Ser
305                 310                 315                 320
Pro Asn Pro Trp His Val Ser Phe Ser Tyr Ala Arg Ala Leu Gln Asn
                325                 330                 335
Thr Val Leu Lys Thr Trp Gln Gly Arg Pro Asp Asn Val Glu Ala Ala
            340                 345                 350
Gln Lys Ser Leu Leu Val Arg Ala Lys Ala Asn Ser Leu Ala Gln Leu
            355                 360                 365
Gly Arg Tyr Ser Ala Glu Gly Glu Ser Glu Glu Ala Thr Lys Gly Met
            370                 375                 380
Phe Val Lys Gly Tyr Thr Tyr
385                 390

<210> SEQ ID NO 38
<211> LENGTH: 391
<212> TYPE: PRT
<213> ORGANISM: Populus trichocarpa

<400> SEQUENCE: 38
```

```
Met Ala Cys Ala Ser Phe Val Lys Leu Asn Ala Ser Ser Ser Trp
1               5                   10                  15

Thr Gly Gln Lys Ser Ser Phe Gly Lys Arg Ser Pro Gly Ser Ser Thr
            20                  25                  30

Arg Arg Val Ser Phe Ser Ile Arg Ala Ser Ser Tyr Thr Asp Glu Leu
            35                  40                  45

Val Gln Thr Ala Lys Leu Ile Ala Ser Pro Gly Arg Gly Ile Leu Ala
    50                  55                  60

Ile Asp Glu Ser Asn Ala Thr Cys Gly Lys Arg Leu Ala Ser Ile Gly
65                  70                  75                  80

Leu Asp Asn Thr Glu Thr Asn Arg Gln Ala Tyr Arg Gln Leu Leu
                85                  90                  95

Thr Thr Pro Gly Leu Gly Glu Tyr Ile Ser Gly Ala Ile Leu Phe Glu
            100                 105                 110

Glu Thr Leu Tyr Gln Ser Thr Thr Asp Gly Arg Lys Phe Val Asp Cys
            115                 120                 125

Leu Arg Asp Glu Asn Ile Val Pro Gly Ile Lys Val Asp Lys Gly Leu
            130                 135                 140

Val Pro Leu Pro Gly Ser Asn Asn Glu Ser Trp Cys Gln Gly Leu Asp
145                 150                 155                 160

Gly Leu Ala Ser Arg Ser Ala Glu Tyr Tyr Lys Gln Gly Ala Arg Phe
                165                 170                 175

Ala Lys Trp Arg Thr Val Val Ser Ile Pro Cys Gly Pro Ser Ala Leu
            180                 185                 190

Ala Val Lys Glu Ala Ala Trp Gly Leu Ala Arg Tyr Ala Ala Ile Ser
            195                 200                 205

Gln Asp Asn Gly Leu Val Pro Ile Val Glu Pro Glu Ile Leu Leu Asp
    210                 215                 220

Gly Asp His Pro Ile Asp Arg Thr Leu Glu Val Ala Glu Lys Val Trp
225                 230                 235                 240

Ala Glu Val Phe Tyr Tyr Leu Ala Glu Asn Asn Val Val Phe Glu Gly
                245                 250                 255

Ile Leu Leu Lys Pro Ser Met Val Thr Pro Gly Ala Glu His Lys Glu
            260                 265                 270

Lys Ala Ser Pro Asp Thr Ile Ala Lys Tyr Thr Leu Thr Met Leu Lys
            275                 280                 285

Arg Arg Val Pro Pro Ala Val Pro Gly Ile Met Phe Leu Ser Gly Gly
            290                 295                 300

Gln Ser Glu Val Gln Ala Thr Leu Asn Leu Asn Ala Met Asn Gln Ser
305                 310                 315                 320

Pro Asn Pro Trp His Val Ser Phe Ser Tyr Ala Arg Ala Leu Gln Asn
                325                 330                 335

Thr Val Leu Lys Thr Trp Gln Gly Arg Pro Glu Asn Val Glu Ala Ala
            340                 345                 350

Gln Lys Ser Leu Leu Val Arg Ala Lys Ala Asn Ser Leu Ala Gln Leu
            355                 360                 365

Gly Arg Tyr Ser Ala Glu Gly Glu Ser Glu Glu Ala Lys Lys Gly Met
            370                 375                 380

Phe Val Lys Gly Tyr Thr Tyr
385                 390

<210> SEQ ID NO 39
<211> LENGTH: 394
<212> TYPE: PRT
```

<213> ORGANISM: Ricinus communis

<400> SEQUENCE: 39

Met Ala Cys Ala Ser Phe Ala Lys Leu Asn Ala Ala Ser Ser Thr Trp
1               5                   10                  15

Ile Gly Gln Gln Ser Phe Gly Gln Arg Pro Gly Ser Ser Ala Arg
            20                  25                  30

Phe Ala Thr Arg Arg Val Ser Leu Pro Ile Arg Ala Ser Ser Tyr Lys
        35                  40                  45

Asp Glu Leu Val Gln Thr Ala Lys Thr Val Ala Ser Pro Gly Arg Gly
    50                  55                  60

Ile Leu Ala Ile Asp Glu Ser Asn Ala Thr Cys Gly Lys Arg Leu Ala
65                  70                  75                  80

Ser Ile Gly Leu Asp Asn Asn Glu Thr Asn Arg Gln Ala Tyr Arg Gln
                85                  90                  95

Leu Leu Leu Thr Thr Pro Gly Leu Gly Glu Tyr Ile Ser Gly Ala Ile
            100                 105                 110

Leu Phe Glu Glu Thr Leu Tyr Gln Ser Thr Thr Asp Gly Lys Lys Phe
        115                 120                 125

Val Asp Cys Leu Arg Asp Gln Asn Ile Val Pro Gly Ile Lys Val Asp
    130                 135                 140

Lys Gly Leu Val Pro Leu Pro Gly Ser Asn Asn Glu Ser Trp Cys Gln
145                 150                 155                 160

Gly Leu Asp Gly Leu Ala Ser Arg Ser Ala Glu Tyr Tyr Lys Gln Gly
                165                 170                 175

Ala Arg Phe Ala Lys Trp Arg Thr Val Val Ser Ile Pro Cys Gly Pro
            180                 185                 190

Ser Ala Leu Ala Val Lys Glu Ala Ala Trp Gly Leu Ala Arg Tyr Ala
        195                 200                 205

Ala Ile Ser Gln Asp Asn Gly Leu Val Pro Ile Val Glu Pro Glu Ile
    210                 215                 220

Leu Leu Asp Gly Asp His Gly Ile Glu Arg Thr Leu Glu Val Ala Glu
225                 230                 235                 240

Lys Val Trp Ala Glu Val Phe Phe Tyr Leu Ala Glu Asn Asn Val Val
                245                 250                 255

Phe Glu Gly Ile Leu Leu Lys Pro Ser Met Val Thr Pro Gly Ala Glu
            260                 265                 270

His Lys Glu Lys Ala Ser Pro Asp Thr Ile Ala Lys Tyr Thr Leu Thr
        275                 280                 285

Met Leu Arg Arg Arg Val Pro Pro Ala Val Pro Gly Ile Met Phe Leu
    290                 295                 300

Ser Gly Gly Gln Ser Glu Val Glu Ala Thr Leu Asn Leu Asn Ala Ile
305                 310                 315                 320

Asn Gln Ser Pro Asn Pro Trp His Val Ser Phe Ser Tyr Ala Arg Ala
                325                 330                 335

Leu Gln Asn Ser Val Leu Lys Thr Trp Gln Gly His Pro Glu Asn Val
            340                 345                 350

Glu Ala Ala Gln Lys Ala Leu Leu Val Arg Ala Lys Ala Asn Ser Leu
        355                 360                 365

Ala Gln Leu Gly Lys Tyr Ser Ala Glu Gly Glu Asn Glu Glu Ala Lys
    370                 375                 380

Lys Gly Met Phe Val Lys Gly Tyr Thr Tyr
385                 390

```
<210> SEQ ID NO 40
<211> LENGTH: 393
<212> TYPE: PRT
<213> ORGANISM: Vitis vinifera

<400> SEQUENCE: 40

Met Ala Ser Val Thr Phe Ala Lys Phe Asn Ala Ser Ser Ser Gln Trp
1               5                   10                  15

Ile Gly Gln Gln Ser Phe Ser Gln Arg Gln Gly Ser Ser Ala Arg Phe
            20                  25                  30

Pro Ala Arg Arg Val Ser Val Pro Ile Arg Ala Gly Ser Tyr Ser Glu
        35                  40                  45

Glu Leu Val Gln Thr Ala Lys Thr Val Ala Ser Pro Gly Arg Gly Ile
50                  55                  60

Leu Ala Ile Asp Glu Ser Asn Ala Thr Cys Gly Lys Arg Leu Ala Ser
65                  70                  75                  80

Ile Gly Leu Asp Asn Thr Glu Pro Asn Arg Gln Ala Tyr Arg Gln Leu
            85                  90                  95

Leu Leu Thr Thr Pro Gly Leu Gly Glu Tyr Ile Ser Gly Ala Ile Leu
            100                 105                 110

Phe Glu Glu Thr Leu Tyr Gln Ser Thr Thr Asp Gly Lys Lys Phe Val
        115                 120                 125

Asp Cys Leu Arg Glu Lys Lys Ile Val Pro Gly Ile Lys Val Asp Lys
130                 135                 140

Gly Leu Val Pro Leu Pro Gly Ser Asn Asn Glu Ser Trp Cys Gln Gly
145                 150                 155                 160

Leu Asp Gly Leu Ala Ser Arg Ser Ala Glu Tyr Tyr Lys Gln Gly Ala
                165                 170                 175

Arg Phe Ala Lys Trp Arg Thr Val Val Ser Ile Pro Cys Gly Pro Ser
            180                 185                 190

Ala Leu Ala Val Lys Glu Ala Ala Trp Gly Leu Ala Arg Tyr Ala Ala
        195                 200                 205

Ile Ser Gln Asp Asn Gly Leu Val Pro Ile Val Glu Pro Glu Ile Leu
210                 215                 220

Leu Asp Gly Asp His Pro Ile Asp Arg Thr Leu Glu Val Ala Glu Lys
225                 230                 235                 240

Val Trp Ser Glu Val Phe Phe Tyr Leu Ala Gln Asn Asn Val Leu Phe
                245                 250                 255

Glu Gly Ile Leu Leu Lys Pro Ser Met Val Thr Pro Gly Ala Glu His
            260                 265                 270

Lys Glu Lys Ala Ser Pro Glu Thr Ile Ala Lys Tyr Thr Leu Thr Met
        275                 280                 285

Leu Arg Arg Arg Val Pro Pro Ala Val Pro Gly Ile Met Phe Leu Ser
290                 295                 300

Gly Gly Gln Ser Glu Val Glu Ala Thr Leu Asn Leu Asn Ala Met Asn
305                 310                 315                 320

Gln Ser Pro Asn Pro Trp His Val Ser Phe Ser Tyr Ala Arg Ala Leu
                325                 330                 335

Gln Asn Thr Val Leu Lys Thr Trp Gln Gly His Pro Gly Asn Val Glu
            340                 345                 350

Ala Ala Gln Lys Ser Leu Leu Val Arg Ala Lys Ala Asn Ser Leu Ala
        355                 360                 365

Gln Leu Gly Lys Tyr Ser Ala Glu Gly Glu Ser Glu Glu Ala Lys Lys
370                 375                 380
```

```
Gly Met Phe Val Gln Gly Tyr Thr Tyr
385                 390

<210> SEQ ID NO 41
<211> LENGTH: 387
<212> TYPE: PRT
<213> ORGANISM: Zea mays

<400> SEQUENCE: 41

Met Ala Met Ala Thr Ala Lys Leu Asn Ser Pro Ala Thr Ser Leu Val
1               5                   10                  15

Ala Gly Gly Leu Thr Arg Arg Ser Ala Pro Ala Arg Cys Thr Thr Val
                20                  25                  30

Ile Arg Ala Ala Ala Gly Ser Tyr Ser Asp Glu Leu Ile Ser Thr Ala
            35                  40                  45

Lys Ser Val Ala Ser Pro Gly Arg Gly Ile Leu Ala Ile Asp Glu Ser
        50                  55                  60

Asn Ala Thr Cys Gly Lys Arg Leu Ser Ser Ile Gly Leu Asp Asn Thr
65                  70                  75                  80

Glu Val Asn Arg Gln Ala Tyr Arg Gln Leu Leu Leu Thr Thr Ala Gly
                85                  90                  95

Leu Gly Glu Tyr Ile Ser Gly Ala Ile Leu Phe Glu Glu Thr Leu Tyr
            100                 105                 110

Gln Ser Thr Thr Asp Gly Lys Lys Phe Val Asp Cys Leu Lys Asp Gln
        115                 120                 125

Asn Ile Met Pro Gly Ile Lys Val Asp Lys Gly Leu Val Pro Leu Pro
130                 135                 140

Gly Ser Asn Asn Glu Ser Trp Cys Gln Gly Leu Asp Gly Leu Ala Ser
145                 150                 155                 160

Arg Cys Ala Glu Tyr Tyr Lys Gln Gly Ala Arg Phe Ala Lys Trp Arg
                165                 170                 175

Thr Val Val Ser Ile Pro Cys Gly Pro Ser Ala Leu Ala Val Lys Glu
            180                 185                 190

Ala Ala Trp Gly Leu Ala Arg Tyr Ala Ala Ile Ala Gln Asp Asn Gly
        195                 200                 205

Leu Val Pro Ile Val Glu Pro Glu Ile Leu Leu Asp Gly Asp His Gly
210                 215                 220

Ile Glu Gly Ala Leu Glu Val Ala Glu Lys Val Trp Ser Glu Val Phe
225                 230                 235                 240

Phe Tyr Leu Ala Glu Asn Asn Val Leu Phe Glu Gly Ile Leu Leu Lys
                245                 250                 255

Pro Ser Met Val Thr Pro Gly Ala Glu His Lys Glu Lys Ala Ser Pro
            260                 265                 270

Glu Ala Ile Ala Lys Tyr Thr Leu Thr Met Leu Arg Arg Arg Val Pro
        275                 280                 285

Pro Ala Val Pro Gly Ile Met Phe Leu Ser Gly Gly Gln Ser Glu Val
290                 295                 300

Glu Ala Thr Leu Asn Leu Asn Ala Met Asn Gln Ser Leu Asn Pro Trp
305                 310                 315                 320

His Val Ser Phe Ser Tyr Val Arg Ala Leu Gln Asn Ser Val Leu Lys
                325                 330                 335

Thr Trp Gln Gly Arg Pro Glu Asn Val Glu Ala Ala Gln Lys Ala Leu
            340                 345                 350

Leu Val Arg Ala Lys Ala Asn Ser Leu Ala Gln Leu Gly Arg Tyr Thr
```

355                 360                 365
Gly Glu Gly Glu Ser Asp Asp Ala Lys Lys Gly Met Phe Gln Lys Gly
            370                 375                 380

Tyr Thr Tyr
385

<210> SEQ ID NO 42
<211> LENGTH: 396
<212> TYPE: PRT
<213> ORGANISM: Zea mays

<400> SEQUENCE: 42

Met Ala Met Ala Thr Ala Lys Leu Asn Ser Pro Ala Thr Ser Leu Val
1               5                   10                  15

Ala Gly Gly Arg Thr Arg Arg Ser Ala Pro Ala Arg Cys Thr Thr Val
            20                  25                  30

Ile Arg Ala Ala Ala Gly Ser Tyr Ser Asp Glu Leu Ile Ser Thr Ala
        35                  40                  45

Lys Ser Val Ala Ser Pro Gly Arg Gly Ile Leu Ala Ile Asp Glu Ser
    50                  55                  60

Asn Ala Thr Cys Gly Lys Arg Leu Ser Ser Ile Gly Leu Asp Asn Thr
65                  70                  75                  80

Glu Val Asn Arg Gln Ala Tyr Arg Gln Leu Leu Leu Thr Thr Ala Gly
                85                  90                  95

Leu Gly Glu Tyr Ile Ser Gly Ala Ile Leu Phe Glu Glu Thr Leu Tyr
            100                 105                 110

Gln Ser Thr Thr Asp Gly Lys Lys Phe Val Asp Cys Leu Lys Asp Gln
        115                 120                 125

Asn Ile Met Pro Gly Ile Lys Val Asp Lys Gly Leu Val Pro Leu Pro
130                 135                 140

Gly Ser Asn Asn Glu Ser Trp Cys Gln Gly Leu Asp Gly Leu Ala Ser
145                 150                 155                 160

Arg Cys Ala Glu Tyr Tyr Lys Gln Gly Ala Arg Phe Ala Lys Trp Arg
                165                 170                 175

Thr Val Val Ser Ile Pro Cys Gly Pro Ser Ala Leu Ala Val Lys Glu
            180                 185                 190

Ala Ala Trp Gly Leu Ala Arg Tyr Ala Ala Ile Ala Gln Asp Asn Gly
        195                 200                 205

Leu Val Pro Ile Val Glu Pro Glu Ile Leu Leu Asp Gly Asp His Gly
    210                 215                 220

Ile Glu Gly Ala Leu Glu Val Ala Glu Lys Val Trp Ser Glu Val Phe
225                 230                 235                 240

Phe Tyr Leu Ala Glu Asn Asn Val Leu Phe Glu Gly Ile Leu Leu Lys
                245                 250                 255

Pro Ser Met Val Thr Pro Gly Ala Glu His Lys Glu Lys Ala Ser Pro
            260                 265                 270

Glu Ala Ile Ala Lys Tyr Thr Leu Thr Met Leu Arg Arg Arg Val Pro
        275                 280                 285

Pro Ala Val Pro Gly Ile Met Phe Leu Ser Gly Gly Gln Ser Glu Val
    290                 295                 300

Glu Ala Thr Leu Asn Leu Asn Ala Met Asn Gln Ser Leu Asn Pro Trp
305                 310                 315                 320

His Val Ser Phe Ser Tyr Val Arg Ala Leu Gln Asn Ser Val Leu Lys
                325                 330                 335

-continued

```
Thr Trp Gln Gly Arg Pro Glu Asn Val Glu Ala Ala Gln Lys Ala Leu
                340                 345                 350

Leu Val Arg Ala Lys Ala Asn Ser Leu Ala Gln Leu Gly Arg Tyr Thr
            355                 360                 365

Gly Glu Gly Glu Ser Asp Asp Ala Lys Lys Gly Met Phe Gln Lys Gly
        370                 375                 380

Tyr Thr Leu Met Cys Gln Arg Asp Val Ser Met Thr
385                 390                 395

<210> SEQ ID NO 43
<211> LENGTH: 388
<212> TYPE: PRT
<213> ORGANISM: Oryza sativa

<400> SEQUENCE: 43

Met Ala Met Leu Thr Ala Lys Leu Thr Ser Pro Ala Ala Thr Thr
1               5                   10                  15

Trp Leu Pro Gly Gly Gly Arg Ser Ala Pro Pro Arg Arg Ala Thr
            20                  25                  30

Val Ile Arg Ala Ala Val Ser Tyr Ala Asp Glu Leu Val Ser Thr
        35                  40                  45

Ala Lys Ser Val Ala Ser Pro Gly Arg Gly Ile Leu Ala Ile Asp Glu
    50                  55                  60

Ser Asn Ala Thr Cys Gly Lys Arg Leu Ala Ser Ile Gly Leu Asp Asn
65                  70                  75                  80

Thr Glu Val Asn Arg Gln Ala Tyr Arg Gln Leu Leu Leu Thr Thr Ala
                85                  90                  95

Gly Leu Gly Glu Tyr Ile Ser Gly Ala Ile Leu Phe Glu Glu Thr Leu
            100                 105                 110

Tyr Gln Ser Thr Thr Asp Gly Lys Lys Phe Val Asp Cys Leu Lys Asp
        115                 120                 125

Gln Asn Ile Met Pro Gly Ile Lys Val Asp Lys Gly Leu Val Pro Leu
    130                 135                 140

Pro Gly Ser Asn Asn Glu Ser Trp Cys Gln Gly Leu Asp Gly Leu Ala
145                 150                 155                 160

Ser Arg Cys Ala Glu Tyr Tyr Lys Gln Gly Ala Arg Phe Ala Lys Trp
                165                 170                 175

Arg Thr Val Val Ser Ile Pro Cys Gly Pro Ser Ala Leu Ala Val Lys
            180                 185                 190

Glu Ala Ala Trp Gly Leu Ala Arg Tyr Ala Ala Ile Ala Gln Asp Asn
        195                 200                 205

Gly Leu Val Pro Ile Val Glu Pro Glu Ile Leu Leu Asp Gly Asp His
    210                 215                 220

Ala Ile Glu Arg Thr Leu Glu Val Ala Glu Lys Val Trp Ser Glu Val
225                 230                 235                 240

Phe Phe Tyr Leu Ala Gln Asn Asn Val Leu Phe Glu Gly Ile Leu Leu
                245                 250                 255

Lys Pro Ser Met Val Thr Pro Gly Ala Glu His Lys Gln Lys Ala Thr
            260                 265                 270

Pro Glu Ala Ile Ala Lys His Thr Leu Thr Met Leu Arg Arg Arg Val
        275                 280                 285

Pro Pro Ala Val Pro Gly Ile Met Phe Leu Ser Gly Gly Gln Ser Glu
    290                 295                 300

Val Glu Ala Thr Leu Asn Leu Asn Ala Met Asn Gln Glu Pro Asn Pro
305                 310                 315                 320
```

```
Trp His Val Ser Phe Ser Tyr Ala Arg Ala Leu Gln Asn Ser Val Leu
            325                 330                 335

Lys Thr Trp Gln Gly Arg Pro Glu Asn Val Glu Ala Ala Gln Lys Ala
        340                 345                 350

Leu Leu Val Arg Ala Lys Ala Asn Ser Leu Ala Gln Leu Gly Arg Tyr
            355                 360                 365

Thr Gly Glu Gly Glu Ser Asp Glu Ala Lys Lys Gly Met Phe Gln Lys
    370                 375                 380

Gly Tyr Thr Tyr
385

<210> SEQ ID NO 44
<211> LENGTH: 21
<212> TYPE: DNA
<213> ORGANISM: Artificial
<220> FEATURE:
<223> OTHER INFORMATION: Synthetic DNA

<400> SEQUENCE: 44
ggatcctatg gcgtctgcta g                                         21

<210> SEQ ID NO 45
<211> LENGTH: 21
<212> TYPE: DNA
<213> ORGANISM: Artificial
<220> FEATURE:
<223> OTHER INFORMATION: Synthetic DNA

<400> SEQUENCE: 45
atctgcaacg gtctcgggag a                                         21

<210> SEQ ID NO 46
<211> LENGTH: 22
<212> TYPE: DNA
<213> ORGANISM: Artificial
<220> FEATURE:
<223> OTHER INFORMATION: Synthetic DNA

<400> SEQUENCE: 46
gtgtggtccg aggtgttctt ct                                        22

<210> SEQ ID NO 47
<211> LENGTH: 24
<212> TYPE: DNA
<213> ORGANISM: Artificial
<220> FEATURE:
<223> OTHER INFORMATION: Synthetic DNA

<400> SEQUENCE: 47
gagctcgagt aggtgtaacc cttg                                      24

<210> SEQ ID NO 48
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (4)..(4)
```

```
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably V or I
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K or R
<220> FEATURE:
<221> NAME/KEY: misc_feature
<222> LOCATION: (18)..(18)
<223> OTHER INFORMATION: Xaa can be any naturally occurring amino acid

<400> SEQUENCE: 48

Xaa Cys Gly Xaa Phe Asp Gly His Gly Xaa Xaa Gly Xaa Xaa Xaa Xaa
1               5                   10                  15

Xaa Xaa Val

<210> SEQ ID NO 49
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
<223> OTHER INFORMATION: Xaa can be any naturally occurring amino acid,
      or preferably V or L
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid,
      or preferably I, V, F or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid,
      or preferably G or A
<220> FEATURE:
<221> NAME/KEY: misc_feature
<222> LOCATION: (13)..(14)
```

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably L, V or I
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I

<400> SEQUENCE: 49

Ser Gly Xaa Thr Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25

<210> SEQ ID NO 50
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (4)..(4)
<223> OTHER INFORMATION: Xaa can be any naturally occurring amino acid,
      or preferably M or V
<220> FEATURE:
<221> NAME/KEY: misc_feature
<222> LOCATION: (5)..(5)
<223> OTHER INFORMATION: Xaa can be any naturally occurring amino acid,
      or preferably S or A
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
      or preferably F or L
<220> FEATURE:
<221> NAME/KEY: misc_feature
<222> LOCATION: (11)..(12)
<223> OTHER INFORMATION: Xaa can be any naturally occurring amino acid
```

-continued

```
<220> FEATURE:
<221> NAME/KEY: misc_feature
<222> LOCATION: (13)..(13)
<223> OTHER INFORMATION: Xaa can be any naturally occurring amino acid,
      or preferably L, I or V
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid,
      or preferably Y, F or H
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or M
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (40)..(40)
<223> OTHER INFORMATION: Xaa can be any naturally occurring amino acid,
``` or preferably T or S
<220> FEATURE:
<221> NAME/KEY: misc_feature
<222> LOCATION: (43)..(43)
<223> OTHER INFORMATION: Xaa can be any naturally occurring amino acid,
   or preferably V, I or M
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid,
   or preferably L, I, V or M
<220> FEATURE:
<221> NAME/KEY: misc_feature
<222> LOCATION: (48)..(48)
<223> OTHER INFORMATION: Xaa can be any naturally occurring amino acid,
   or preferably S or T
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid,
   or preferably E or D
<220> FEATURE:
<221> NAME/KEY: misc_feature
<222> LOCATION: (52)..(52)
<223> OTHER INFORMATION: Xaa can be any naturally occurring amino acid,
   or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
   or preferably L, V or I
<220> FEATURE:
<221> NAME/KEY: misc_feature
<222> LOCATION: (56)..(56)
<223> OTHER INFORMATION: Xaa can be any naturally occurring amino acid,
   or preferably I or V

<400> SEQUENCE: 50

Gly Leu Ala Xaa Xaa Arg Xaa Xaa Gly Asp Xaa Xaa Xaa Lys Xaa Xaa
1               5                   10                  15

Gly Xaa Xaa Xaa Xaa Pro Xaa Xaa Xaa Xaa Xaa Xaa Xaa Xaa Xaa Xaa
            20                  25                  30

Asp Xaa Xaa Xaa Xaa Leu Ala Xaa Asp Gly Xaa Trp Asp Xaa Xaa Xaa
        35                  40                  45

Asn Xaa Xaa Xaa Xaa Xaa Xaa Xaa
    50                  55

<210> SEQ ID NO 51
<211> LENGTH: 3261
<212> TYPE: DNA
<213> ORGANISM: Oryza sativa
<220> FEATURE:
<221> NAME/KEY: CDS
<222> LOCATION: (1)..(3261)

<400> SEQUENCE: 51 atg ggc tgc tca cct tct aag gtg tgt tca tgt cca cat tat aag ggc     48
Met Gly Cys Ser Pro Ser Lys Val Cys Ser Cys Pro His Tyr Lys Gly
1               5                   10                  15 agt ttg tgc ttc tgt gac tgt gga tgc ttt gga caa aca cct gac tcc     96

```
Ser Leu Cys Phe Cys Asp Cys Gly Cys Phe Gln Thr Pro Asp Ser
            20                  25                  30 cca aga gag tca agg gga aaa tca aac cgg gtt agg gga aag aca gat    144
Pro Arg Glu Ser Arg Gly Lys Ser Asn Arg Val Arg Gly Lys Thr Asp
            35                  40                  45 tct agt gct tca gat gct tct tct gat gac cta gag gaa gat gat gat    192
Ser Ser Ala Ser Asp Ala Ser Ser Asp Asp Leu Glu Glu Asp Asp Asp
50                  55                  60 gga ttg cac caa atg aac att aca agg gac tct aat gtt ggt atc aat    240
Gly Leu His Gln Met Asn Ile Thr Arg Asp Ser Asn Val Gly Ile Asn
65                  70                  75                  80 cga ctc tca agg gtc tca tca caa ttt ctt cca cca gaa ggt tca cgt    288
Arg Leu Ser Arg Val Ser Ser Gln Phe Leu Pro Pro Glu Gly Ser Arg
            85                  90                  95 aaa gtt cga atc cca ttg ggg aat tat gac ctg aga tat tcc tac ttg    336
Lys Val Arg Ile Pro Leu Gly Asn Tyr Asp Leu Arg Tyr Ser Tyr Leu
            100                 105                 110 tct caa aga ggc tac tac cca gaa tca ttg gac aag cca aac caa gac    384
Ser Gln Arg Gly Tyr Tyr Pro Glu Ser Leu Asp Lys Pro Asn Gln Asp
            115                 120                 125 agt ttt tgt ata cat act cca ttt gga aca agc cct gat gac cat ttc    432
Ser Phe Cys Ile His Thr Pro Phe Gly Thr Ser Pro Asp Asp His Phe
130                 135                 140 ttt ggt gta ttt gat ggc cat gga gaa tat gga gct cag tgc tca caa    480
Phe Gly Val Phe Asp Gly His Gly Glu Tyr Gly Ala Gln Cys Ser Gln
145                 150                 155                 160 ttt gta aag cga aga cta tgc gaa aac ctg ctc aga gat gac cgg ttc    528
Phe Val Lys Arg Arg Leu Cys Glu Asn Leu Leu Arg Asp Asp Arg Phe
            165                 170                 175 cgt act gat gtt gtt cag gct ctt cat tct gct ttc ttg gca aca aat    576
Arg Thr Asp Val Val Gln Ala Leu His Ser Ala Phe Leu Ala Thr Asn
            180                 185                 190 tca cag ctt cat gca gac agc tta gat gat tct atg agt ggt act act    624
Ser Gln Leu His Ala Asp Ser Leu Asp Asp Ser Met Ser Gly Thr Thr
            195                 200                 205 gca gtc act gtg ctg gtg agg ggt aaa act att tac att gcg aat acg    672
Ala Val Thr Val Leu Val Arg Gly Lys Thr Ile Tyr Ile Ala Asn Thr
210                 215                 220 ggt gat tca cgt gct gtt att gcc gaa aaa aga ggg gaa gat gtt gtt    720
Gly Asp Ser Arg Ala Val Ile Ala Glu Lys Arg Gly Glu Asp Val Val
225                 230                 235                 240 gct gtt gac ctg tcc ata gat caa aca ccc tac agg act gat gag ctt    768
Ala Val Asp Leu Ser Ile Asp Gln Thr Pro Tyr Arg Thr Asp Glu Leu
            245                 250                 255 gaa agg gtc aag gag tgt ggt gct agg gtt atg acg ttg gat cag ata    816
Glu Arg Val Lys Glu Cys Gly Ala Arg Val Met Thr Leu Asp Gln Ile
            260                 265                 270 gag ggg cta aag aac cca gat gta cag tgt tgg ggc acc gag gaa agt    864
Glu Gly Leu Lys Asn Pro Asp Val Gln Cys Trp Gly Thr Glu Glu Ser
            275                 280                 285 gat gac ggt gat cct cca agg ttg tgg gtg caa aat ggc atg tat cca    912
Asp Asp Gly Asp Pro Pro Arg Leu Trp Val Gln Asn Gly Met Tyr Pro
290                 295                 300 gga act gct ttt act cgc agc att gga gat tct gtc gct gaa tct atc    960
Gly Thr Ala Phe Thr Arg Ser Ile Gly Asp Ser Val Ala Glu Ser Ile
305                 310                 315                 320 ggt gtt gtc gct aat cct gag att ttt atc ctg gag ctc aat gcc aac    1008
Gly Val Val Ala Asn Pro Glu Ile Phe Ile Leu Glu Leu Asn Ala Asn
            325                 330                 335
```

| | |
|---|---|
| cat cca ttc ttt gtt ctt gct agt gat gga gtt ttt gag ttt ctt tct<br>His Pro Phe Phe Val Leu Ala Ser Asp Gly Val Phe Glu Phe Leu Ser<br>340                        345                     350 | 1056 |
| agt caa act gtt gtc gac atg att gct aaa tac aag gat cct cgt gat<br>Ser Gln Thr Val Val Asp Met Ile Ala Lys Tyr Lys Asp Pro Arg Asp<br>      355                   360                  365 | 1104 |
| gcg tgc gct gca att gtt gct gaa tcc tat cgc ctc tgg cta cag tat<br>Ala Cys Ala Ala Ile Val Ala Glu Ser Tyr Arg Leu Trp Leu Gln Tyr<br>370                       375                 380 | 1152 |
| gaa act cgt aca gat gac att aca ata ata gtt gtt cat att aac ggg<br>Glu Thr Arg Thr Asp Asp Ile Thr Ile Ile Val Val His Ile Asn Gly<br>385                       390                  395                 400 | 1200 |
| tta act gat atg gaa tgt act caa act gta atg aaa gta tct tta caa<br>Leu Thr Asp Met Glu Cys Thr Gln Thr Val Met Lys Val Ser Leu Gln<br>               405                  410               415 | 1248 |
| cct tcc caa caa gtc gta gaa ttg gta ggc tca gaa tca cca tcg aca<br>Pro Ser Gln Gln Val Val Glu Leu Val Gly Ser Glu Ser Pro Ser Thr<br>          420                   425                 430 | 1296 |
| ata agt ttg aat ccc aag aac cag cgt tcc agg caa gat cta tca cgt<br>Ile Ser Leu Asn Pro Lys Asn Gln Arg Ser Arg Gln Asp Leu Ser Arg<br>435                       440                 445 | 1344 |
| gct cgg ctg aga gca ctt gaa agt tcc ctg gaa aat ggt cga cta tgg<br>Ala Arg Leu Arg Ala Leu Glu Ser Ser Leu Glu Asn Gly Arg Leu Trp<br>450                       455                 460 | 1392 |
| gtc cct cca tcc cca tcg cat cgg aag aca tgg gaa gag caa gca cat<br>Val Pro Pro Ser Pro Ser His Arg Lys Thr Trp Glu Glu Gln Ala His<br>465                       470                  475                 480 | 1440 |
| att gag cga ata cta cac gac cat ttc ctc ttc agg aag ctc act gac<br>Ile Glu Arg Ile Leu His Asp His Phe Leu Phe Arg Lys Leu Thr Asp<br>               485                  490               495 | 1488 |
| tca cag tgc cat gtt tta ctt gat tgc atg caa aga gtt gag gtg aaa<br>Ser Gln Cys His Val Leu Leu Asp Cys Met Gln Arg Val Glu Val Lys<br>500                       505                 510 | 1536 |
| gct ggg gat ata gtg gtg cag cag ggc ggt gaa ggc gag tgc ttc tat<br>Ala Gly Asp Ile Val Val Gln Gln Gly Gly Glu Gly Glu Cys Phe Tyr<br>          515                   520                 525 | 1584 |
| gta gtt ggg agt ggt gag ttt gaa gtg cta gcc att cag gaa gaa gat<br>Val Val Gly Ser Gly Glu Phe Glu Val Leu Ala Ile Gln Glu Glu Asp<br>530                       535                 540 | 1632 |
| gga aag gaa gtt aca aag gtt cta cat cgg tat act gct gac aaa cta<br>Gly Lys Glu Val Thr Lys Val Leu His Arg Tyr Thr Ala Asp Lys Leu<br>545                       550                  555                 560 | 1680 |
| tct tct ttt ggg gag cta gca cta atg tat aat aaa cca ctt caa gct<br>Ser Ser Phe Gly Glu Leu Ala Leu Met Tyr Asn Lys Pro Leu Gln Ala<br>               565                  570               575 | 1728 |
| tca gtc cgt gct gtg act act gga act tta tgg gct cta aag cga gag<br>Ser Val Arg Ala Val Thr Thr Gly Thr Leu Trp Ala Leu Lys Arg Glu<br>580                       585                  590 | 1776 |
| gat ttt cgg gga att ctg atg tca gag ttt tca aat ata cca tca tta<br>Asp Phe Arg Gly Ile Leu Met Ser Glu Phe Ser Asn Ile Pro Ser Leu<br>          595                   600                 605 | 1824 |
| aag ttg ctc cga tca gtg gag ctg ttt acg aga ttg aca atg ctt caa<br>Lys Leu Leu Arg Ser Val Glu Leu Phe Thr Arg Leu Thr Met Leu Gln<br>610                       615                 620 | 1872 |
| cta agt caa ctt gct gat tct ctt gtt gaa gta act ttt ggg gat ggt<br>Leu Ser Gln Leu Ala Asp Ser Leu Val Glu Val Thr Phe Gly Asp Gly<br>625                       630                  635                 640 | 1920 |
| caa atg ata gta gac aag aat gat gat gca tct tcc ttg tat att att<br>Gln Met Ile Val Asp Lys Asn Asp Asp Ala Ser Ser Leu Tyr Ile Ile<br>               645                  650               655 | 1968 |

```
caa aga ggt cgt gtg aaa ctt aaa ttg gct gca gat cag gta aat tca    2016
Gln Arg Gly Arg Val Lys Leu Lys Leu Ala Ala Asp Gln Val Asn Ser
            660                 665                 670 gat gcc tgg gat ctt ctt agt tct caa aca aag gtg gcc caa tca agt    2064
Asp Ala Trp Asp Leu Leu Ser Ser Gln Thr Lys Val Ala Gln Ser Ser
        675                 680                 685 cga gaa gat ggt aat tac gtg ttt gag ata gat gaa ggg gga cac ttt    2112
Arg Glu Asp Gly Asn Tyr Val Phe Glu Ile Asp Glu Gly Gly His Phe
    690                 695                 700 gga gag tgg gct ctc ttt ggg gag aca att gct ttt act gct atg tca    2160
Gly Glu Trp Ala Leu Phe Gly Glu Thr Ile Ala Phe Thr Ala Met Ser
705                 710                 715                 720 gtt ggt gat gtg act tgt tct act att gca aag gag aag ttt gac tca    2208
Val Gly Asp Val Thr Cys Ser Thr Ile Ala Lys Glu Lys Phe Asp Ser
                725                 730                 735 att att ggg ccc ttg cca aaa gtt tcc cag tct gat tcc aag ctc aaa    2256
Ile Ile Gly Pro Leu Pro Lys Val Ser Gln Ser Asp Ser Lys Leu Lys
            740                 745                 750 gat tcc ttg gtt cct aaa ggg cat ggt gca gat gat agt tcc ttc agg    2304
Asp Ser Leu Val Pro Lys Gly His Gly Ala Asp Asp Ser Ser Phe Arg
        755                 760                 765 aag gcg cag cta tct gat ttg gaa tgg aaa atg tgc ata tat gcc gct    2352
Lys Ala Gln Leu Ser Asp Leu Glu Trp Lys Met Cys Ile Tyr Ala Ala
    770                 775                 780 gat tgc agt gag att ggt ctt gtc caa cta aga ggt tct gac aag atc    2400
Asp Cys Ser Glu Ile Gly Leu Val Gln Leu Arg Gly Ser Asp Lys Ile
785                 790                 795                 800 aaa agc tta aag agg ttt tac atc aag aga gta aaa gac ctt cat aag    2448
Lys Ser Leu Lys Arg Phe Tyr Ile Lys Arg Val Lys Asp Leu His Lys
                805                 810                 815 gaa aaa cac gta ttt gat gag aag gat ctc atg aaa tct ttg agc caa    2496
Glu Lys His Val Phe Asp Glu Lys Asp Leu Met Lys Ser Leu Ser Gln
            820                 825                 830 tca act tgt gtg cca gaa gtt cta tgt act tgc gct gat caa tcc tac    2544
Ser Thr Cys Val Pro Glu Val Leu Cys Thr Cys Ala Asp Gln Ser Tyr
        835                 840                 845 cta gga ata ctg ctg aat tgt tgc ctt tgt tgc tca ctg gct tca ata    2592
Leu Gly Ile Leu Leu Asn Cys Cys Leu Cys Cys Ser Leu Ala Ser Ile
    850                 855                 860 ctt cat gca cca cta aat gag tcg tct gca cga ttc tat gca gcc tct    2640
Leu His Ala Pro Leu Asn Glu Ser Ser Ala Arg Phe Tyr Ala Ala Ser
865                 870                 875                 880 gtc gtc gta gcg cta gaa aat ctc cat cag agg tcc att ctt tac aga    2688
Val Val Val Ala Leu Glu Asn Leu His Gln Arg Ser Ile Leu Tyr Arg
                885                 890                 895 ggt gtt tct gca gac att ctt atg gtc gac cga tca ggg cat ctt caa    2736
Gly Val Ser Ala Asp Ile Leu Met Val Asp Arg Ser Gly His Leu Gln
            900                 905                 910 cta gtt gac ttc agg ttt gca aag aag ttg caa ggt gaa agg act tac    2784
Leu Val Asp Phe Arg Phe Ala Lys Lys Leu Gln Gly Glu Arg Thr Tyr
        915                 920                 925 aca ata tgt ggg att gcc gac tct cta gct cca gag ata gtt ctt ggt    2832
Thr Ile Cys Gly Ile Ala Asp Ser Leu Ala Pro Glu Ile Val Leu Gly
    930                 935                 940 agg ggc cat gga ttt tct gct gac tgg tgg gcg ctg gga gtg ttg att    2880
Arg Gly His Gly Phe Ser Ala Asp Trp Trp Ala Leu Gly Val Leu Ile
945                 950                 955                 960 tat ttc atg ctg caa tca gac atg cca ttt ggc tct tgg agg gag agt    2928
Tyr Phe Met Leu Gln Ser Asp Met Pro Phe Gly Ser Trp Arg Glu Ser
```

```
                 965                 970                 975
gaa ctg gaa cct ttt gca aag att gcc aag ggt cac ctt gtc atg cca      2976
Glu Leu Glu Pro Phe Ala Lys Ile Ala Lys Gly His Leu Val Met Pro
            980                 985                 990 tca aca ttc agc atc gaa gtt gtt gac ctt att aca aag cta ctc gag      3024
Ser Thr Phe Ser Ile Glu Val Val Asp Leu Ile Thr Lys Leu Leu Glu
        995                 1000                1005 gta aac gaa aat gcg cgc ctt ggg gcc aag gga gcg gaa tct gtg          3069
Val Asn Glu Asn Ala Arg Leu Gly Ala Lys Gly Ala Glu Ser Val
    1010                1015                1020 aaa aga cac ccc tgg ttt gat ggc att gac tgg aaa caa ata gca          3114
Lys Arg His Pro Trp Phe Asp Gly Ile Asp Trp Lys Gln Ile Ala
    1025                1030                1035 gat ggt act tat aca gta ccc caa gaa atc acc gat cgt gtc gac          3159
Asp Gly Thr Tyr Thr Val Pro Gln Glu Ile Thr Asp Arg Val Asp
    1040                1045                1050 agc tat gta gaa act ctt aca gag gac ttg aca gca tcc cct tcc          3204
Ser Tyr Val Glu Thr Leu Thr Glu Asp Leu Thr Ala Ser Pro Ser
    1055                1060                1065 atg cca agt gaa gaa aca gct gat cag gct gct cca gaa tgg atc          3249
Met Pro Ser Glu Glu Thr Ala Asp Gln Ala Ala Pro Glu Trp Ile
    1070                1075                1080 cag gat tgg tga                                                      3261
Gln Asp Trp
    1085

<210> SEQ ID NO 52
<211> LENGTH: 1086
<212> TYPE: PRT
<213> ORGANISM: Oryza sativa

<400> SEQUENCE: 52

Met Gly Cys Ser Pro Ser Lys Val Cys Ser Cys Pro His Tyr Lys Gly
1               5                   10                  15

Ser Leu Cys Phe Cys Asp Cys Gly Cys Phe Gly Gln Thr Pro Asp Ser
            20                  25                  30

Pro Arg Glu Ser Arg Gly Lys Ser Asn Arg Val Arg Gly Lys Thr Asp
        35                  40                  45

Ser Ser Ala Ser Asp Ala Ser Ser Asp Leu Glu Glu Asp Asp Asp
    50                  55                  60

Gly Leu His Gln Met Asn Ile Thr Arg Asp Ser Asn Val Gly Ile Asn
65                  70                  75                  80

Arg Leu Ser Arg Val Ser Ser Gln Phe Leu Pro Pro Glu Gly Ser Arg
                85                  90                  95

Lys Val Arg Ile Pro Leu Gly Asn Tyr Asp Leu Arg Tyr Ser Tyr Leu
            100                 105                 110

Ser Gln Arg Gly Tyr Tyr Pro Glu Ser Leu Asp Lys Pro Asn Gln Asp
        115                 120                 125

Ser Phe Cys Ile His Thr Pro Phe Gly Thr Ser Pro Asp Asp His Phe
    130                 135                 140

Phe Gly Val Phe Asp Gly His Gly Glu Tyr Gly Ala Gln Cys Ser Gln
145                 150                 155                 160

Phe Val Lys Arg Arg Leu Cys Glu Asn Leu Leu Arg Asp Asp Arg Phe
                165                 170                 175

Arg Thr Asp Val Val Gln Ala Leu His Ser Ala Phe Leu Ala Thr Asn
            180                 185                 190

Ser Gln Leu His Ala Asp Ser Leu Asp Asp Ser Met Ser Gly Thr Thr
```

-continued

```
            195                 200                 205
Ala Val Thr Val Leu Val Arg Gly Lys Thr Ile Tyr Ile Ala Asn Thr
210                 215                 220

Gly Asp Ser Arg Ala Val Ile Ala Glu Lys Arg Gly Glu Asp Val Val
225                 230                 235                 240

Ala Val Asp Leu Ser Ile Asp Gln Thr Pro Tyr Arg Thr Asp Glu Leu
                245                 250                 255

Glu Arg Val Lys Glu Cys Gly Ala Arg Val Met Thr Leu Asp Gln Ile
            260                 265                 270

Glu Gly Leu Lys Asn Pro Asp Val Gln Cys Trp Gly Thr Glu Glu Ser
        275                 280                 285

Asp Asp Gly Asp Pro Pro Arg Leu Trp Val Gln Asn Gly Met Tyr Pro
290                 295                 300

Gly Thr Ala Phe Thr Arg Ser Ile Gly Asp Ser Val Ala Glu Ser Ile
305                 310                 315                 320

Gly Val Val Ala Asn Pro Glu Ile Phe Ile Leu Glu Leu Asn Ala Asn
                325                 330                 335

His Pro Phe Phe Val Leu Ala Ser Asp Gly Val Phe Glu Phe Leu Ser
            340                 345                 350

Ser Gln Thr Val Val Asp Met Ile Ala Lys Tyr Lys Asp Pro Arg Asp
        355                 360                 365

Ala Cys Ala Ala Ile Val Ala Glu Ser Tyr Arg Leu Trp Leu Gln Tyr
370                 375                 380

Glu Thr Arg Thr Asp Asp Ile Thr Ile Ile Val Val His Ile Asn Gly
385                 390                 395                 400

Leu Thr Asp Met Glu Cys Thr Gln Thr Val Met Lys Val Ser Leu Gln
                405                 410                 415

Pro Ser Gln Gln Val Val Glu Leu Val Gly Ser Glu Ser Pro Ser Thr
            420                 425                 430

Ile Ser Leu Asn Pro Lys Asn Gln Arg Ser Arg Gln Asp Leu Ser Arg
        435                 440                 445

Ala Arg Leu Arg Ala Leu Glu Ser Ser Leu Glu Asn Gly Arg Leu Trp
450                 455                 460

Val Pro Pro Ser Pro Ser His Arg Lys Thr Trp Glu Glu Gln Ala His
465                 470                 475                 480

Ile Glu Arg Ile Leu His Asp His Phe Leu Phe Arg Lys Leu Thr Asp
                485                 490                 495

Ser Gln Cys His Val Leu Leu Asp Cys Met Gln Arg Val Glu Val Lys
            500                 505                 510

Ala Gly Asp Ile Val Gln Gln Gly Gly Glu Gly Cys Phe Tyr
        515                 520                 525

Val Val Gly Ser Gly Glu Phe Glu Val Leu Ala Ile Gln Glu Glu Asp
530                 535                 540

Gly Lys Glu Val Thr Lys Val Leu His Arg Tyr Thr Ala Asp Lys Leu
545                 550                 555                 560

Ser Ser Phe Gly Glu Leu Ala Leu Met Tyr Asn Lys Pro Leu Gln Ala
                565                 570                 575

Ser Val Arg Ala Val Thr Thr Gly Thr Leu Trp Ala Leu Lys Arg Glu
            580                 585                 590

Asp Phe Arg Gly Ile Leu Met Ser Glu Phe Ser Asn Ile Pro Ser Leu
        595                 600                 605

Lys Leu Leu Arg Ser Val Glu Leu Phe Thr Arg Leu Thr Met Leu Gln
            610                 615                 620
```

```
Leu Ser Gln Leu Ala Asp Ser Leu Val Glu Val Thr Phe Gly Asp Gly
625                 630                 635                 640

Gln Met Ile Val Asp Lys Asn Asp Ala Ser Ser Leu Tyr Ile Ile
        645                 650                 655

Gln Arg Gly Arg Val Lys Leu Lys Leu Ala Ala Asp Gln Val Asn Ser
            660                 665                 670

Asp Ala Trp Asp Leu Leu Ser Ser Gln Thr Lys Val Ala Gln Ser Ser
            675                 680                 685

Arg Glu Asp Gly Asn Tyr Val Phe Glu Ile Asp Gly Gly His Phe
            690                 695                 700

Gly Glu Trp Ala Leu Phe Gly Glu Thr Ile Ala Phe Thr Ala Met Ser
705                 710                 715                 720

Val Gly Asp Val Thr Cys Ser Thr Ile Ala Lys Glu Lys Phe Asp Ser
                725                 730                 735

Ile Ile Gly Pro Leu Pro Lys Val Ser Gln Ser Asp Ser Lys Leu Lys
            740                 745                 750

Asp Ser Leu Val Pro Lys Gly His Gly Ala Asp Asp Ser Ser Phe Arg
        755                 760                 765

Lys Ala Gln Leu Ser Asp Leu Glu Trp Lys Met Cys Ile Tyr Ala Ala
770                 775                 780

Asp Cys Ser Glu Ile Gly Leu Val Gln Leu Arg Gly Ser Asp Lys Ile
785                 790                 795                 800

Lys Ser Leu Lys Arg Phe Tyr Ile Lys Arg Val Lys Asp Leu His Lys
                805                 810                 815

Glu Lys His Val Phe Asp Glu Lys Asp Leu Met Lys Ser Leu Ser Gln
            820                 825                 830

Ser Thr Cys Val Pro Glu Val Leu Cys Thr Cys Ala Asp Gln Ser Tyr
            835                 840                 845

Leu Gly Ile Leu Leu Asn Cys Cys Leu Cys Cys Ser Leu Ala Ser Ile
850                 855                 860

Leu His Ala Pro Leu Asn Glu Ser Ser Ala Arg Phe Tyr Ala Ala Ser
865                 870                 875                 880

Val Val Val Ala Leu Glu Asn Leu His Gln Arg Ser Ile Leu Tyr Arg
                885                 890                 895

Gly Val Ser Ala Asp Ile Leu Met Val Asp Arg Ser Gly His Leu Gln
            900                 905                 910

Leu Val Asp Phe Arg Phe Ala Lys Lys Leu Gln Gly Glu Arg Thr Tyr
        915                 920                 925

Thr Ile Cys Gly Ile Ala Asp Ser Leu Ala Pro Glu Ile Val Leu Gly
        930                 935                 940

Arg Gly His Gly Phe Ser Ala Asp Trp Trp Ala Leu Gly Val Leu Ile
945                 950                 955                 960

Tyr Phe Met Leu Gln Ser Asp Met Pro Phe Gly Ser Trp Arg Glu Ser
                965                 970                 975

Glu Leu Glu Pro Phe Ala Lys Ile Ala Lys Gly His Leu Val Met Pro
            980                 985                 990

Ser Thr Phe Ser Ile Glu Val Val Asp Leu Ile Thr Lys Leu Leu Glu
        995                 1000                1005

Val Asn Glu Asn Ala Arg Leu Gly Ala Lys Gly Ala Glu Ser Val
    1010                1015                1020

Lys Arg His Pro Trp Phe Asp Gly Ile Asp Trp Lys Gln Ile Ala
    1025                1030                1035
```

```
Asp Gly Thr Tyr Thr Val Pro Gln Glu Ile Thr Asp Arg Val Asp
    1040                1045                1050

Ser Tyr Val Glu Thr Leu Thr Glu Asp Leu Thr Ala Ser Pro Ser
    1055                1060                1065

Met Pro Ser Glu Glu Thr Ala Asp Gln Ala Ala Pro Glu Trp Ile
    1070                1075                1080

Gln Asp Trp
    1085

<210> SEQ ID NO 53
<211> LENGTH: 331
<212> TYPE: PRT
<213> ORGANISM: Arabidopsis thaliana

<400> SEQUENCE: 53

Met Gly His Cys Phe Ser Leu Pro Ser Ser Gln Ser Glu Ile His Glu
1               5                   10                  15

Asp Asn Glu His Gly Asp Gly Asn Val Val Cys Tyr Gly Glu Phe
            20                  25                  30

Gly Leu Asp Gln Asp Leu Pro Val His Arg Leu Gly Ser Val Cys Ser
            35                  40                  45

Ile Gln Gly Thr Lys Val Leu Asn Gln Asp His Ala Val Leu Tyr Gln
    50                  55                  60

Gly Tyr Gly Thr Arg Asp Thr Glu Leu Cys Gly Val Phe Asp Gly His
65                  70                  75                  80

Gly Lys Asn Gly His Met Val Ser Lys Met Val Arg Asn Arg Leu Pro
                85                  90                  95

Ser Val Leu Ala Leu Lys Glu Glu Leu Asn Gln Glu Ser Asn Val
            100                 105                 110

Cys Glu Glu Glu Ala Ser Lys Trp Glu Lys Ala Cys Phe Thr Ala Phe
            115                 120                 125

Arg Leu Ile Asp Arg Glu Leu Asn Leu Gln Val Phe Asn Cys Ser Phe
    130                 135                 140

Ser Gly Ser Thr Gly Val Val Ala Ile Thr Gln Gly Asp Asp Leu Val
145                 150                 155                 160

Ile Ala Asn Leu Gly Asp Ser Arg Ala Val Leu Gly Thr Met Thr Glu
                165                 170                 175

Asp Gly Glu Ile Lys Ala Val Gln Leu Thr Ser Asp Leu Thr Pro Asp
            180                 185                 190

Val Pro Ser Glu Ala Glu Arg Ile Arg Met Cys Lys Gly Arg Val Phe
            195                 200                 205

Ala Met Lys Thr Glu Pro Ser Ser Gln Arg Val Trp Leu Pro Asn Gln
    210                 215                 220

Asn Ile Pro Gly Leu Ala Met Ser Arg Ala Phe Gly Asp Phe Arg Leu
225                 230                 235                 240

Lys Asp His Gly Val Ile Ala Val Pro Glu Ile Ser Gln His Arg Ile
                245                 250                 255

Thr Ser Lys Asp Gln Phe Leu Val Leu Ala Thr Asp Gly Val Trp Asp
            260                 265                 270

Met Leu Ser Asn Asp Glu Val Val Ser Leu Ile Trp Ser Ser Gly Lys
            275                 280                 285

Lys Gln Ala Ser Ala Ala Lys Met Val Ala Glu Ala Ala Glu Ala Ala
    290                 295                 300

Trp Lys Lys Arg Leu Lys Tyr Thr Lys Val Asp Asp Ile Thr Val Ile
305                 310                 315                 320
```

```
Cys Leu Phe Leu Gln Asn Lys Glu Gln Pro Ser
            325                 330
```

<210> SEQ ID NO 54
<211> LENGTH: 326
<212> TYPE: PRT
<213> ORGANISM: Arabidopsis thaliana

<400> SEQUENCE: 54

```
Met Gly Phe Cys Phe Cys Leu Ser Ser Gly Ser Thr Asp Lys Ser
1               5                   10                  15

Gln Ile Tyr Glu Ile Thr Asp Tyr Gly Gln Glu Asn Ala Val Leu Tyr
            20                  25                  30

Ser Asp His His Val Val Pro Gln Asn Leu Gly Ser Val Ser Ser Leu
            35                  40                  45

Ala Gly Gly Lys Gly Leu Asn Gln Asp Ala Ala Ile Leu His Leu Gly
50                  55                  60

Tyr Gly Thr Glu Glu Gly Ala Leu Cys Gly Val Phe Asp Gly His Gly
65                  70                  75                  80

Pro Arg Gly Ala Phe Val Ser Lys Asn Val Arg Asn Gln Leu Pro Ser
                85                  90                  95

Ile Leu Leu Gly His Met Asn Asn His Ser Val Thr Arg Asp Trp Lys
            100                 105                 110

Leu Ile Cys Glu Thr Ser Cys Leu Glu Met Asp Lys Arg Ile Leu Lys
            115                 120                 125

Val Lys Lys Ile His Asp Cys Ser Ala Ser Gly Thr Thr Ala Val Leu
130                 135                 140

Ala Val Lys His Gly Asn Gln Val Met Val Ala Asn Leu Gly Asp Ser
145                 150                 155                 160

Arg Ala Val Met Ile Gly Thr Ser Glu Asp Gly Glu Thr Lys Val Ala
                165                 170                 175

Gln Leu Thr Asn Asp Leu Lys Pro Ser Val Pro Ser Glu Ala Glu Arg
            180                 185                 190

Ile Arg Lys Arg Asn Gly Arg Val Leu Ala Leu Glu Ser Glu Pro His
            195                 200                 205

Ile Leu Arg Val Trp Leu Pro Thr Glu Asn Arg Pro Gly Leu Ala Met
210                 215                 220

Ser Arg Ala Phe Gly Asp Phe Leu Leu Lys Ser Tyr Gly Val Ile Ala
225                 230                 235                 240

Thr Pro Gln Val Ser Thr His Gln Ile Thr Ser Ser Asp Gln Phe Leu
                245                 250                 255

Leu Leu Ala Ser Asp Gly Val Trp Asp Val Leu Ser Asn Glu Glu Val
            260                 265                 270

Ala Thr Val Val Met Lys Ser Ala Ser Glu Ala Gly Ala Ala Asn Glu
            275                 280                 285

Val Ala Glu Ala Ala Thr Asn Ala Trp Ile Gln Lys Phe Pro Thr Val
            290                 295                 300

Lys Ile Asp Asp Ile Ser Val Val Cys Leu Ser Leu Asn Lys Lys His
305                 310                 315                 320

Asn Pro Gln Pro Gln Ile
                325
```

<210> SEQ ID NO 55
<211> LENGTH: 491
<212> TYPE: PRT

<213> ORGANISM: Arabidopsis thaliana

<400> SEQUENCE: 55

```
Met Gly Leu Cys His Ser Lys Ile Asp Lys Thr Thr Arg Lys Glu Thr
1               5                   10                  15

Gly Ala Thr Ser Thr Ala Thr Thr Val Glu Arg Gln Ser Ser Gly
            20                  25                  30

Arg Leu Arg Arg Pro Arg Asp Leu Tyr Ser Gly Gly Glu Ile Ser Glu
            35                  40                  45

Ile Gln Gln Val Val Gly Arg Leu Val Gly Asn Gly Ser Ser Glu Ile
        50                  55                  60

Ala Cys Leu Tyr Thr Gln Gln Gly Lys Lys Gly Thr Asn Gln Asp Ala
65                  70                  75                  80

Met Leu Val Trp Glu Asn Phe Cys Ser Arg Ser Asp Thr Val Leu Cys
                85                  90                  95

Gly Val Phe Asp Gly His Gly Pro Phe Gly His Met Val Ser Lys Arg
            100                 105                 110

Val Arg Asp Met Leu Pro Phe Thr Leu Ser Thr Gln Leu Lys Thr Thr
            115                 120                 125

Ser Gly Thr Glu Gln Ser Ser Lys Asn Gly Leu Asn Ser Ala Pro
        130                 135                 140

Thr Cys Val Asp Glu Glu Gln Trp Cys Glu Leu Gln Leu Cys Glu Lys
145                 150                 155                 160

Asp Glu Lys Leu Phe Pro Glu Met Tyr Leu Pro Leu Lys Arg Ala Leu
                165                 170                 175

Leu Lys Thr Cys Gln Gln Met Asp Lys Glu Leu Lys Met His Pro Thr
            180                 185                 190

Ile Asn Cys Phe Cys Ser Gly Thr Thr Ser Val Thr Val Ile Lys Gln
            195                 200                 205

Gly Lys Asp Leu Val Val Gly Asn Ile Gly Asp Ser Arg Ala Val Leu
        210                 215                 220

Ala Thr Arg Asp Gln Asp Asn Ala Leu Val Ala Val Gln Leu Thr Ile
225                 230                 235                 240

Asp Leu Lys Pro Asp Leu Pro Ser Glu Ser Ala Arg Ile His Arg Cys
                245                 250                 255

Lys Gly Arg Val Phe Ala Leu Gln Asp Glu Pro Glu Val Ala Arg Val
            260                 265                 270

Trp Leu Pro Asn Ser Asp Ser Pro Gly Leu Ala Met Ala Arg Ala Phe
        275                 280                 285

Gly Asp Phe Cys Leu Lys Asp Tyr Gly Leu Ile Ser Val Pro Asp Ile
290                 295                 300

Asn Tyr His Arg Leu Thr Glu Arg Asp Gln Tyr Ile Ile Leu Ala Thr
305                 310                 315                 320

Asp Gly Val Trp Asp Val Leu Ser Asn Lys Glu Ala Val Asp Ile Val
                325                 330                 335

Ala Ser Ala Pro Ser Arg Asp Thr Ala Ala Arg Ala Val Val Asp Thr
            340                 345                 350

Ala Val Arg Ala Trp Arg Leu Lys Tyr Pro Thr Ser Lys Asn Asp Asp
        355                 360                 365

Cys Ala Val Val Cys Leu Phe Leu Glu Asp Thr Ser Ala Gly Gly Thr
370                 375                 380

Val Glu Val Ser Glu Thr Val Asn His Ser His Glu Glu Ser Thr Glu
385                 390                 395                 400
```

```
Ser Val Thr Ile Thr Ser Lys Asp Ala Asp Lys Lys Glu Glu Ala
                405             410             415

Ser Thr Glu Thr Asn Glu Thr Val Pro Val Trp Glu Ile Lys Glu Glu
            420             425             430

Lys Thr Pro Glu Ser Cys Arg Ile Glu Ser Lys Lys Thr Thr Leu Ala
        435             440             445

Glu Cys Ile Ser Val Lys Asp Asp Glu Glu Trp Ser Ala Leu Glu Gly
    450             455             460

Leu Thr Arg Val Asn Ser Leu Leu Ser Ile Pro Arg Phe Phe Ser Gly
465             470             475             480

Glu Leu Arg Ser Ser Ser Trp Arg Lys Trp Leu
            485             490

<210> SEQ ID NO 56
<211> LENGTH: 504
<212> TYPE: PRT
<213> ORGANISM: Arabidopsis thaliana

<400> SEQUENCE: 56

Met Gly Leu Cys Tyr Ser Val Asp Arg Thr Thr Gly Lys Glu Pro Gly
1               5                   10                  15

Glu Ala Ser Ser Thr Ala Thr Ala Glu Thr Val Glu Glu Arg Ser
            20                  25                  30

Gly Ser Gly Arg Trp Arg Arg Pro Arg Asp Leu Lys Gly Gly Gly Asp
        35                  40                  45

Ile Glu Gly Ile Pro Gln Val Leu Gly Arg Leu Val Ser Asn Gly Ser
    50                  55                  60

Ser Lys Ile Ala Cys Leu Tyr Thr Gln Gln Gly Lys Lys Gly Thr Asn
65                  70                  75                  80

Gln Asp Ala Met Leu Val Phe Glu Asn Phe Cys Ser Arg Asp Asp Thr
                85                  90                  95

Val Phe Cys Gly Val Phe Asp Gly His Gly Pro Phe Gly His Met Val
            100                 105                 110

Ala Lys Lys Val Arg Asp Thr Leu Pro Phe Thr Leu Leu Thr Gln Leu
        115                 120                 125

Lys Met Thr Ser Glu Ser Asp Gln Ser Ser Leu Val Gly Ala Asn Gly
    130                 135                 140

Phe Gln Ile Lys Cys Thr Glu Glu Glu Val Gln Thr Thr Glu Ser
145                 150                 155                 160

Glu Gln Val Gln Lys Thr Glu Ser Val Thr Thr Met Asp Glu Gln Trp
                165                 170                 175

Cys Glu Leu Asn Pro Asn Val Asn Asn Asp Glu Leu Pro Glu Met Tyr
            180                 185                 190

Leu Pro Leu Lys His Ala Met Leu Lys Ser Cys Gln Gln Ile Asp Lys
        195                 200                 205

Glu Leu Lys Met His Pro Thr Ile Asp Cys Phe Cys Ser Gly Thr Thr
    210                 215                 220

Ser Val Thr Leu Ile Lys Gln Gly Glu Asp Leu Val Val Gly Asn Ile
225                 230                 235                 240

Gly Asp Ser Arg Ala Val Leu Ala Thr Arg Asp Glu Asp Asn Ala Leu
                245                 250                 255

Leu Ala Val Gln Leu Thr Ile Asp Leu Lys Pro Asp Leu Pro Gly Glu
            260                 265                 270

Ser Ala Arg Ile Gln Lys Cys Lys Gly Arg Val Phe Ala Leu Gln Asp
        275                 280                 285
```

```
Glu Pro Glu Val Ala Arg Val Trp Leu Pro Asn Ser Asp Ser Pro Gly
    290                 295                 300

Leu Ala Met Ala Arg Ala Phe Gly Asp Phe Cys Leu Lys Asp Tyr Gly
305                 310                 315                 320

Leu Ile Ser Val Pro Asp Ile Asn Tyr Arg Arg Leu Thr Glu Arg Asp
                325                 330                 335

Gln Phe Ile Ile Leu Ala Ser Asp Gly Val Trp Asp Val Leu Ser Asn
            340                 345                 350

Lys Glu Ala Val Asp Ile Val Ala Ser Ala Pro Ser Arg Ser Thr Ala
        355                 360                 365

Ala Arg Ala Leu Val Asp Thr Ala Val Arg Ser Trp Arg Ile Lys Tyr
    370                 375                 380

Pro Thr Ser Lys Asn Asp Asp Cys Thr Val Val Cys Leu Phe Leu Gln
385                 390                 395                 400

Asp Ser Ser Val Ala Met Glu Val Ser Thr Asn Val Lys Lys Asp Ser
                405                 410                 415

Pro Lys Glu Glu Ser Ile Glu Ser Val Thr Asn Ser Thr Ser Lys Glu
            420                 425                 430

Glu Asp Glu Ile Val Pro Val Lys Asp Glu Lys Ile Pro Glu Ser Cys
        435                 440                 445

Gly Ile Glu Ser Lys Met Met Thr Met Thr Leu Ala Glu Cys Ile Ser
    450                 455                 460

Val Ala Gln Asp Asp Glu Glu Trp Ser Ala Leu Glu Gly Leu Thr Arg
465                 470                 475                 480

Val Asn Ser Leu Leu Ser Ile Pro Arg Phe Leu Ser Gly Glu Leu Arg
                485                 490                 495

Ser Thr Ser Trp Arg Lys Trp Leu
            500

<210> SEQ ID NO 57
<211> LENGTH: 447
<212> TYPE: PRT
<213> ORGANISM: Arabidopsis thaliana

<400> SEQUENCE: 57

Met His Arg Pro Cys Leu Gly Met Gly Cys Cys Gly Ser Lys Met Gly
1               5                   10                  15

Lys Arg Gly Phe Ser Asp Arg Met Val Ser Leu His Asn Leu Val Ser
            20                  25                  30

Ile Pro Asn Arg Ile Ile Gly Asn Gly Lys Ser Arg Ser Ser Cys Ile
        35                  40                  45

Phe Thr Gln Gln Gly Arg Lys Gly Ile Asn Gln Asp Ala Met Ile Val
    50                  55                  60

Trp Glu Asp Phe Met Ser Lys Asp Val Thr Phe Cys Gly Val Phe Asp
65                  70                  75                  80

Gly His Gly Pro His Gly His Leu Val Ala Arg Lys Val Arg Asp Ser
                85                  90                  95

Leu Pro Val Lys Leu Leu Ser Leu Leu Asn Ser Ile Lys Ser Lys Gln
            100                 105                 110

Asn Gly Pro Ile Gly Thr Arg Ala Ser Lys Ser Asp Ser Leu Glu Ala
        115                 120                 125

Glu Lys Glu Glu Ser Thr Glu Glu Asp Lys Leu Asn Phe Leu Trp Glu
    130                 135                 140

Glu Ala Phe Leu Lys Ser Phe Asn Ala Met Asp Lys Glu Leu Arg Ser
```

His Pro Asn Leu Glu Cys Phe Cys Ser Gly Cys Thr Ala Val Thr Ile
145                 150                 155                 160

Ile Lys Gln Gly Ser Asn Leu Tyr Met Gly Asn Ile Gly Asp Ser Arg
            165                 170                 175

Ala Ile Leu Gly Ser Lys Asp Ser Asn Asp Ser Met Ile Ala Val Gln
        180                 185                 190

Leu Thr Val Asp Leu Lys Pro Asp Leu Pro Arg Glu Ala Glu Arg Ile
    195                 200                 205

Lys Gln Cys Lys Gly Arg Val Phe Ala Leu Gln Asp Glu Pro Glu Val
210                 215                 220

Ser Arg Val Trp Leu Pro Phe Asp Asn Ala Pro Gly Leu Ala Met Ala
225                 230                 235                 240

Arg Ala Phe Gly Asp Phe Cys Leu Lys Asp Tyr Gly Val Ile Ser Ile
            245                 250                 255

Pro Glu Phe Ser His Arg Val Leu Thr Asp Arg Asp Gln Phe Ile Val
        260                 265                 270

Leu Ala Ser Asp Gly Val Trp Asp Val Leu Ser Asn Glu Glu Val Val
    275                 280                 285

Glu Val Val Ala Ser Ala Thr Ser Arg Ala Ser Ala Ala Arg Leu Val
290                 295                 300

Val Asp Ser Ala Val Arg Glu Trp Lys Leu Lys Tyr Pro Thr Ser Lys
305                 310                 315                 320

Met Asp Asp Cys Ala Val Val Cys Leu Phe Leu Asp Gly Arg Met Asp
            325                 330                 335

Ser Glu Thr Ser Asp Asn Glu Glu Gln Cys Phe Ser Ser Ala Thr Asn
        340                 345                 350

Ala Val Glu Ser Asp Glu Ser Gln Gly Ala Glu Pro Cys Leu Gln Arg
    355                 360                 365

Asn Val Thr Val Arg Ser Leu Ser Thr Asp Gln Glu Asn Asn Ser Tyr
370                 375                 380

Gly Lys Val Ile Ala Glu Ala Asp Asn Ala Glu Lys Glu Lys Thr Arg
385                 390                 395                 400

Glu Gly Glu Gln Asn Trp Ser Gly Leu Glu Gly Val Thr Arg Val Asn
            405                 410                 415

Ser Leu Val Gln Leu Pro Arg Phe Pro Gly Glu Glu Pro Lys Thr
        420                 425                 430

<210> SEQ ID NO 58
<211> LENGTH: 527
<212> TYPE: PRT
<213> ORGANISM: Arabidopsis thaliana

<400> SEQUENCE: 58

Met Gly Ser Cys Leu Ser Ala Glu Ser Arg Ser Pro Arg Pro Gly Ser
1               5                   10                  15

Pro Cys Ser Pro Ala Phe Ser Val Arg Lys Arg Lys Asn Ser Lys Lys
            20                  25                  30

Arg Pro Gly Ser Arg Asn Ser Ser Phe Asp Tyr Arg Arg Glu Glu Pro
        35                  40                  45

Leu Asn Gln Val Pro Gly Arg Met Phe Leu Asn Gly Ser Thr Glu Val
    50                  55                  60

Ala Cys Ile Tyr Thr Gln Gln Gly Lys Lys Gly Pro Asn Gln Asp Ala
65                  70                  75                  80

```
Met Val Val Trp Glu Asn Phe Gly Ser Arg Thr Asp Thr Ile Phe Cys
                    85                  90                  95
Gly Val Phe Asp Gly His Gly Pro Tyr Gly His Met Val Ala Lys Arg
                100                 105                 110
Val Arg Asp Asn Leu Pro Leu Lys Leu Ser Ala Tyr Trp Glu Ala Lys
                115                 120                 125
Val Pro Val Glu Gly Val Leu Lys Ala Ile Thr Thr Asp Thr Val Asn
130                 135                 140
Asn Val Thr Asn Ile Asn Pro Glu Asp Ala Ala Ala Ala Ala Ala Ala
145                 150                 155                 160
Phe Val Thr Ala Glu Glu Pro Arg Thr Ser Ala Asp Met Glu Glu
                165                 170                 175
Glu Asn Thr Glu Thr Gln Pro Glu Leu Phe Gln Thr Leu Lys Glu Ser
                180                 185                 190
Phe Leu Lys Ala Phe Lys Val Met Asp Arg Glu Leu Lys Phe His Gly
                195                 200                 205
Ser Val Asp Cys Phe Cys Ser Gly Thr Thr Ala Val Thr Leu Ile Lys
                210                 215                 220
Gln Gly Gln Tyr Leu Val Val Gly Asn Val Gly Asp Ser Arg Ala Val
225                 230                 235                 240
Met Gly Thr Arg Asp Ser Glu Asn Thr Leu Val Ala Val Gln Leu Thr
                245                 250                 255
Val Asp Leu Lys Pro Asn Leu Pro Gly Trp Ile Ile Leu Cys Glu Cys
                260                 265                 270
Met Met Leu Ser Cys Gly Cys Met Met Asp Pro Leu Ile Met Phe Ile
                275                 280                 285
Gly Phe Phe Phe Ile Pro Ser Ile Glu Leu Ala Ala Glu Ala Glu Arg
                290                 295                 300
Ile Arg Lys Cys Arg Gly Arg Val Phe Ala Leu Arg Asp Glu Pro Glu
305                 310                 315                 320
Val Cys Arg Val Trp Leu Pro Asn Cys Asp Ser Pro Gly Leu Ala Met
                325                 330                 335
Ala Arg Ala Phe Gly Asp Phe Cys Leu Lys Asp Phe Gly Leu Ile Ser
                340                 345                 350
Val Pro Asp Val Ser Phe Arg Gln Leu Thr Glu Lys Asp Glu Phe Ile
                355                 360                 365
Val Leu Ala Thr Asp Gly Ile Trp Asp Val Leu Ser Asn Glu Asp Val
                370                 375                 380
Val Ala Ile Val Ala Ser Ala Pro Ser Arg Ser Ser Ala Ala Arg Ala
385                 390                 395                 400
Leu Val Glu Ser Ala Val Arg Ala Trp Arg Tyr Lys Tyr Pro Thr Ser
                405                 410                 415
Lys Val Asp Asp Cys Ala Ala Val Cys Leu Tyr Leu Asp Ser Ser Asn
                420                 425                 430
Thr Asn Ala Ile Ser Thr Ala Ser Ser Ile Ser Lys Leu Glu Asp Gly
                435                 440                 445
Glu Glu Glu Glu Leu Lys Ala Thr Thr Glu Asp Asp Ala Ser Gly
                450                 455                 460
Pro Ser Gly Leu Gly Arg Ser Ser Thr Val Arg Ser Gly Lys Glu Ile
465                 470                 475                 480
Ala Leu Asp Glu Ser Glu Thr Glu Lys Leu Ile Lys Glu Ala Asp Asn
                485                 490                 495
Leu Asp Ser Glu Pro Gly Thr Glu Tyr Ser Ala Leu Glu Gly Val Ala
```

```
                500                 505                 510
Arg Val Asn Thr Leu Leu Asn Leu Pro Arg Phe Val Pro Gly Lys
            515                 520                 525

<210> SEQ ID NO 59
<211> LENGTH: 448
<212> TYPE: PRT
<213> ORGANISM: Arabidopsis thaliana

<400> SEQUENCE: 59

Met Gly Ser Cys Leu Ser Ser Gly Gly Gly Ser Arg Arg Ser
1               5                   10                  15

Leu His Gly Ser Pro His Val Pro Gly Pro Gly Arg Arg Lys Arg Pro
            20                  25                  30

Pro Lys Arg Arg Pro Gly Ser Cys Ser Ser Ser Phe Asp Asn Thr Glu
        35                  40                  45

Glu Pro Leu Leu His Arg Ile Pro Gly Arg Met Phe Leu Asn Gly Ser
    50                  55                  60

Thr Asp Thr Val Ser Leu Phe Ser Gln Gln Gly Lys Lys Gly Pro Asn
65                  70                  75                  80

Gln Asp Ala Met Ile Val Trp Glu Asn Phe Gly Ser Met Glu Asp Thr
                85                  90                  95

Val Phe Cys Gly Val Phe Asp Gly His Gly Pro Tyr Gly His Ile Val
            100                 105                 110

Ala Lys Arg Val Arg Asp Leu Leu Pro Leu Lys Leu Gly Ser His Leu
        115                 120                 125

Glu Ser Tyr Val Ser Pro Glu Glu Val Leu Lys Glu Ile Ser Leu Asn
    130                 135                 140

Thr Asp Asp Arg Lys Ile Ser Glu Asp Leu Val His Ile Ser Ala Asn
145                 150                 155                 160

Gly Glu Ser Arg Val Tyr Asn Lys Asp Tyr Val Lys Asp Gln Asp Met
                165                 170                 175

Ile Gln Met Leu Ile Gly Ser Ile Val Lys Ala Tyr Arg Phe Met Asp
            180                 185                 190

Lys Glu Leu Lys Met Gln Val Asp Val Asp Cys Phe Cys Ser Gly Thr
        195                 200                 205

Thr Ala Val Thr Met Val Lys Gln Gly Gln His Leu Val Ile Gly Asn
    210                 215                 220

Ile Gly Asp Ser Arg Ala Val Leu Gly Val Arg Asn Lys Asp Asn Lys
225                 230                 235                 240

Leu Val Pro Phe Gln Leu Thr Glu Asp Leu Lys Pro Asp Val Pro Ala
                245                 250                 255

Glu Ala Glu Arg Ile Lys Arg Cys Arg Gly Arg Ile Phe Ala Leu Arg
            260                 265                 270

Asp Glu Pro Gly Val Ala Arg Leu Trp Leu Pro Asn His Asn Ser Pro
        275                 280                 285

Gly Leu Ala Met Ala Arg Ala Phe Gly Asp Phe Cys Leu Lys Asp Phe
    290                 295                 300

Gly Leu Ile Ser Val Pro Asp Val Ser Tyr Arg Arg Leu Thr Glu Lys
305                 310                 315                 320

Asp Glu Phe Val Val Leu Ala Thr Asp Gly Ile Trp Asp Ala Leu Thr
                325                 330                 335

Asn Glu Glu Val Val Lys Ile Val Ala Lys Ala Pro Thr Arg Ser Ser
            340                 345                 350
```

Ala Gly Arg Ala Leu Val Glu Ala Val Arg Asn Trp Arg Trp Lys
            355                 360                 365

Phe Pro Thr Ser Lys Val Asp Asp Cys Ala Val Val Cys Leu Phe Leu
    370                 375                 380

Asp Ser Glu Pro Asn Arg Leu Ser Thr Ala Ser Phe Ser Lys Glu Lys
385                 390                 395                 400

His Ile Asn Asn Gly Val Thr Glu Pro Glu Pro Asp Thr Ala Ser Ser
                405                 410                 415

Ser Thr Pro Asp Ser Gly Thr Gly Ser Pro Glu Leu Asn Gly Val Asn
            420                 425                 430

Arg Ile Asp Thr Leu Val Asn Leu Pro Val Tyr Val Pro Thr Lys Glu
            435                 440                 445

<210> SEQ ID NO 60
<211> LENGTH: 382
<212> TYPE: PRT
<213> ORGANISM: Arabidopsis thaliana

<400> SEQUENCE: 60

Met Gly Val Cys Cys Ser Lys Gly Thr Gly Ile Ile Val Glu His Gly
1               5                   10                  15

Ala Asp Asp Gly Asn Glu Cys Gly Asp Gly Glu Ala Glu Val Arg Asp
            20                  25                  30

Thr Asn Asp Gly Ala Val Val Arg Thr Arg Gly Ser Ser Lys His Val
        35                  40                  45

Ser Met Ser Ile Lys Gln Gly Lys Lys Gly Ile Asn Gln Asp Ala Met
    50                  55                  60

Thr Val Trp Glu Asn Phe Gly Glu Glu Asp Thr Ile Phe Cys Gly
65                  70                  75                  80

Val Phe Asp Gly His Gly Pro Met Gly His Lys Ile Ser Arg His Val
                85                  90                  95

Cys Glu Asn Leu Pro Ser Arg Val His Ser Lys Ile Arg Ser Ser Lys
            100                 105                 110

Ser Ala Gly Asp Glu Asn Ile Glu Asn Asn Ser Ser Gln Ser Gln Glu
        115                 120                 125

Glu Leu Phe Arg Glu Phe Glu Asp Ile Leu Val Thr Phe Phe Lys Gln
    130                 135                 140

Ile Asp Ser Glu Leu Gly Leu Asp Ser Pro Tyr Asp Ser Phe Cys Ser
145                 150                 155                 160

Gly Thr Thr Ala Val Thr Val Phe Lys Gln Ala Asp Cys Leu Val Ile
                165                 170                 175

Ala Asn Leu Gly His Ser Arg Ala Val Leu Gly Thr Arg Ser Lys Asn
            180                 185                 190

Ser Phe Lys Ala Val Gln Leu Thr Val Asp Leu Lys Pro Cys Val Gln
        195                 200                 205

Arg Glu Ala Glu Arg Ile Val Ser Cys Lys Gly Arg Val Phe Ala Met
    210                 215                 220

Glu Glu Glu Pro Asp Val Tyr Arg Val Trp Met Pro Asp Asp Asp Cys
225                 230                 235                 240

Pro Gly Leu Ala Met Ser Arg Ala Phe Gly Asp Phe Cys Leu Lys Asp
                245                 250                 255

Tyr Gly Leu Val Cys Ile Pro Asp Val Phe Cys Arg Lys Val Ser Arg
            260                 265                 270

Glu Asp Glu Phe Val Val Leu Ala Thr Asp Gly Ile Trp Asp Val Leu
        275                 280                 285

```
Ser Asn Glu Val Val Lys Val Gly Ser Cys Lys Asp Arg Ser
    290                 295                 300

Val Ala Ala Glu Met Leu Val Gln Arg Ala Ala Arg Thr Trp Arg Thr
305                 310                 315                 320

Lys Phe Pro Ala Ser Lys Ala Asp Asp Cys Ala Val Val Leu Tyr
                325                 330                 335

Leu Asn His Arg Pro Tyr Pro Arg Glu Gly Asn Val Ser Arg Ala Ile
                340                 345                 350

Ser Thr Ile Ser Trp Arg Ser Asn Lys Ser Asn Asn Glu Cys Tyr Gly
                355                 360                 365

Ala Ala Pro Leu Ser Pro Leu Gly Leu Ser Gln Arg Val Ser
                370                 375                 380

<210> SEQ ID NO 61
<211> LENGTH: 373
<212> TYPE: PRT
<213> ORGANISM: Arabidopsis thaliana

<400> SEQUENCE: 61

Met Gly His Phe Ser Ser Met Phe Asn Gly Leu Ala Arg Ser Phe Ser
1               5                   10                  15

Ile Lys Lys Val Lys Asn Asn Asn Gly Asn Cys Asp Ala Lys Glu Ala
                20                  25                  30

Ala Asp Glu Met Ala Ser Ala Lys Lys Glu Leu Ile Leu Lys
            35                  40                  45

Ser Ser Gly Tyr Val Asn Val Gln Gly Ser Asn Asn Leu Ala Ser Leu
    50                  55                  60

Phe Ser Lys Arg Gly Glu Lys Gly Val Asn Gln Asp Cys Ala Leu Val
65              70                  75                  80

Trp Glu Gly Phe Gly Cys Gln Glu Asp Met Ile Phe Cys Gly Ile Phe
                85                  90                  95

Asp Gly His Gly Pro Trp Gly His Tyr Val Ala Lys Gln Val Arg Asn
            100                 105                 110

Ser Met Pro Leu Ser Leu Leu Cys Asn Trp Gln Lys Ile Leu Ala Gln
            115                 120                 125

Ala Thr Leu Glu Pro Glu Leu Asp Leu Glu Gly Ser Asn Lys Lys Ile
    130                 135                 140

Ser Arg Phe Asp Ile Trp Lys Gln Ser Tyr Leu Lys Thr Cys Ala Thr
145                 150                 155                 160

Val Asp Gln Glu Leu Glu His His Arg Lys Ile Asp Ser Tyr Tyr Ser
                165                 170                 175

Gly Thr Thr Ala Leu Thr Ile Val Arg Gln Gly Glu Val Ile Tyr Val
            180                 185                 190

Ala Asn Val Gly Asp Ser Arg Ala Val Leu Ala Met Glu Ser Asp Glu
        195                 200                 205

Gly Ser Leu Val Ala Val Gln Leu Thr Leu Asp Phe Lys Pro Asn Leu
    210                 215                 220

Pro Gln Glu Lys Glu Arg Ile Ile Gly Cys Lys Gly Arg Val Phe Cys
225                 230                 235                 240

Leu Asp Asp Glu Pro Gly Val His Arg Val Trp Gln Pro Asp Ala Glu
                245                 250                 255

Thr Pro Gly Leu Ala Met Ser Arg Ala Phe Gly Asp Tyr Cys Ile Lys
            260                 265                 270

Glu Tyr Gly Leu Val Ser Val Pro Glu Val Thr Gln Arg His Ile Ser
```

```
            275                 280                 285
Thr Lys Asp His Phe Ile Ile Leu Ala Ser Asp Gly Ile Trp Asp Val
    290                 295                 300

Ile Ser Asn Gln Glu Ala Ile Glu Ile Val Ser Ser Thr Ala Glu Arg
305                 310                 315                 320

Pro Lys Ala Ala Lys Arg Leu Val Glu Gln Ala Val Arg Ala Trp Lys
                325                 330                 335

Lys Lys Arg Arg Gly Tyr Ser Met Asp Asp Met Ser Val Val Cys Leu
                340                 345                 350

Phe Leu His Ser Ser Ser Ser Ser Leu Ser Gln His His His Ala
                355                 360                 365

Met Thr Ile Leu Lys
                370

<210> SEQ ID NO 62
<211> LENGTH: 351
<212> TYPE: PRT
<213> ORGANISM: Arabidopsis thaliana

<400> SEQUENCE: 62

Met Val Leu Leu Pro Ala Phe Leu Asp Gly Leu Ala Arg Thr Val Ser
1               5                   10                  15

Thr Lys Lys Gly Lys Lys Leu Ser Glu Asp Glu Asp Gly Gly Arg Glu
                20                  25                  30

Ile Ala Lys Ser Met Ile Lys Asp Ser Lys Lys Asn Ser Thr Leu Leu
            35                  40                  45

Gly Thr Ser Gly Phe Val Ser Ser Glu Ser Ser Lys Arg Phe Thr Ser
    50                  55                  60

Ile Cys Ser Asn Arg Gly Glu Lys Gly Ile Asn Gln Asp Arg Ala Ile
65                  70                  75                  80

Val Trp Glu Gly Phe Gly Cys Gln Glu Asp Ile Thr Phe Cys Gly Met
                85                  90                  95

Phe Asp Gly His Gly Pro Trp Gly His Val Ile Ala Lys Arg Val Lys
                100                 105                 110

Lys Ser Phe Pro Ser Ser Leu Leu Cys Gln Trp Gln Gln Thr Leu Ala
            115                 120                 125

Ser Leu Ser Ser Ser Pro Glu Cys Ser Ser Pro Phe Asp Leu Trp Lys
    130                 135                 140

Gln Ala Cys Leu Lys Thr Phe Ser Ile Ile Asp Leu Asp Leu Lys Ile
145                 150                 155                 160

Ser Pro Ser Ile Asp Ser Tyr Cys Ser Gly Cys Thr Ala Leu Thr Ala
                165                 170                 175

Val Leu Gln Gly Asp His Leu Val Ile Ala Asn Ala Gly Asp Ser Arg
                180                 185                 190

Ala Val Ile Ala Thr Thr Ser Asp Asp Gly Asn Gly Leu Val Pro Val
            195                 200                 205

Gln Leu Ser Val Asp Phe Lys Pro Asn Ile Pro Glu Glu Ala Glu Arg
    210                 215                 220

Ile Lys Gln Ser Asp Gly Arg Leu Phe Cys Leu Asp Asp Glu Pro Gly
225                 230                 235                 240

Val Tyr Arg Val Gly Met Pro Asn Gly Gly Ser Leu Gly Leu Ala Val
                245                 250                 255

Ser Arg Ala Phe Gly Asp Tyr Cys Leu Lys Asp Phe Gly Leu Val Ser
                260                 265                 270
```

```
Glu Pro Glu Val Thr Tyr Arg Lys Ile Thr Asp Lys Asp Gln Phe Leu
            275                 280                 285

Ile Leu Ala Thr Asp Gly Met Trp Asp Val Met Thr Asn Asn Glu Ala
290                 295                 300

Val Glu Ile Val Arg Gly Val Lys Glu Arg Lys Ser Ala Lys Arg
305                 310                 315                 320

Leu Val Glu Arg Ala Val Thr Leu Trp Arg Arg Lys Arg Arg Ser Ile
            325                 330                 335

Ala Met Asp Asp Ile Ser Val Leu Cys Leu Phe Phe Arg Pro Ser
            340                 345                 350
```

<210> SEQ ID NO 63
<211> LENGTH: 514
<212> TYPE: PRT
<213> ORGANISM: Arabidopsis thaliana

<400> SEQUENCE: 63

```
Met Gly Cys Ala Tyr Ser Lys Thr Cys Ile Gly Gln Ile Cys Ala Thr
1               5                   10                  15

Lys Glu Asn Ser Ile Arg Gln Thr His Gln Gln Ala Pro Ser Arg Gly
            20                  25                  30

Gly Thr Arg Ala Thr Ala Ala Ala Ala Val Glu Asp Asn Pro
        35                  40                  45

Val Phe Asn Phe Ser Ser Asp Ala Val Asp Val Asp Asn Asp Glu
50                  55                  60

Ile His Gln Leu Gly Leu Ser Arg Asp Gln Glu Trp Gly Ile Thr Arg
65                  70                  75                  80

Leu Ser Arg Val Ser Ser Gln Phe Leu Pro Pro Asp Gly Ser Arg Val
                85                  90                  95

Val Lys Val Pro Ser Cys Asn Tyr Glu Leu Arg Cys Ser Phe Leu Ser
            100                 105                 110

Gln Arg Gly Tyr Tyr Pro Asp Ala Leu Asp Lys Ala Asn Gln Asp Ser
        115                 120                 125

Phe Ala Ile His Thr Pro Phe Gly Ser Asn Ser Asp Asp His Phe Phe
130                 135                 140

Gly Val Phe Asp Gly His Gly Glu Phe Gly Ala Gln Cys Ser Gln Phe
145                 150                 155                 160

Val Lys Arg Arg Leu Cys Glu Asn Leu Leu Arg His Gly Arg Phe Arg
                165                 170                 175

Val Asp Pro Ala Glu Ala Cys Asn Ser Ala Phe Leu Thr Thr Asn Ser
            180                 185                 190

Gln Leu His Ala Asp Leu Val Asp Asp Ser Met Ser Gly Thr Thr Ala
        195                 200                 205

Ile Thr Val Met Val Arg Gly Arg Thr Ile Tyr Val Ala Asn Ala Gly
210                 215                 220

Asp Ser Arg Ala Val Leu Ala Glu Lys Arg Asp Gly Asp Leu Val Ala
225                 230                 235                 240

Val Asp Leu Ser Ile Asp Gln Thr Pro Phe Arg Pro Asp Glu Leu Glu
                245                 250                 255

Arg Val Lys Leu Cys Gly Ala Arg Val Leu Thr Leu Asp Gln Ile Glu
            260                 265                 270

Gly Leu Lys Asn Pro Asp Val Gln Cys Trp Gly Thr Glu Glu Asp Asp
        275                 280                 285

Asp Gly Asp Pro Pro Arg Leu Trp Val Pro Asn Gly Met Tyr Pro Gly
290                 295                 300
```

```
Thr Ala Phe Thr Arg Ser Ile Gly Asp Ser Ile Ala Glu Thr Ile Gly
305                 310                 315                 320

Val Val Ala Asn Pro Glu Ile Ala Val Val Glu Leu Thr Pro Asp Asn
                325                 330                 335

Pro Phe Phe Val Val Ala Ser Asp Gly Val Phe Glu Phe Ile Ser Ser
            340                 345                 350

Gln Thr Val Val Asp Met Val Ala Lys His Lys Asp Pro Arg Asp Ala
        355                 360                 365

Cys Ala Ala Ile Val Ala Glu Ser Tyr Arg Leu Trp Leu Gln Tyr Glu
    370                 375                 380

Thr Arg Thr Asp Asp Ile Thr Ile Ile Val Val His Ile Asp Gly Leu
385                 390                 395                 400

Lys Asp Asp Ala Pro Arg Gln Leu Ser Ser Thr Gly Thr Gln Leu Gln
                405                 410                 415

Pro Pro Ile Pro Gln Val Val Glu Leu Thr Gly Ser Glu Ser Pro Ser
            420                 425                 430

Thr Phe Gly Trp Asn Ser Lys Asn Gln Arg Val Arg His Asp Leu Ser
        435                 440                 445

Arg Ala Arg Ile Arg Ala Ile Glu Asn Ser Leu Glu Asn Gly His Ala
    450                 455                 460

Trp Val Pro Ser Pro Ala His Arg Lys Thr Trp Glu Glu Val
465                 470                 475                 480

Arg Val Leu Val Cys Phe Val Phe Ala Gln Pro Ile Arg Asn Ala Ser
                485                 490                 495

Ser His Ser Tyr Ile Arg Arg Leu Asn Ala Gly Phe Ser Arg Ala Gly
            500                 505                 510

Thr His

<210> SEQ ID NO 64
<211> LENGTH: 348
<212> TYPE: PRT
<213> ORGANISM: Arabidopsis thaliana

<400> SEQUENCE: 64

Met Gly Cys Val Gln Cys Lys Cys Cys Ser Arg Tyr Pro Ser Ser Ser
1               5                   10                  15

Ser Asp Gly Asp Ser Arg Gly Pro Leu Glu Ala Asn Gly Val Leu Lys
                20                  25                  30

Gly Lys Asp Gln Lys Pro Leu Gly Ser Ile His Val Pro Ser Pro Asn
            35                  40                  45

Phe Asp Met Val Tyr Ser Val Leu Ser Gln Arg Gly Tyr Tyr Pro Asp
    50                  55                  60

Ser Pro Asp Lys Glu Asn Gln Asp Thr Tyr Cys Ile Lys Thr Glu Leu
65                  70                  75                  80

Gln Gly Asn Pro Asn Val His Phe Phe Gly Val Phe Asp Gly His Gly
                85                  90                  95

Val Leu Gly Thr Gln Cys Ser Asn Phe Val Lys Glu Arg Val Val Glu
            100                 105                 110

Met Leu Ser Glu Asp Pro Thr Leu Leu Glu Asp Pro Glu Lys Ala Tyr
        115                 120                 125

Lys Ser Ala Phe Leu Arg Val Asn Glu Glu Leu His Asp Ser Glu Ile
    130                 135                 140

Asp Asp Ser Met Ser Gly Thr Thr Ala Ile Thr Val Leu Val Val Gly
145                 150                 155                 160
```

```
Asp Lys Ile Tyr Val Ala Asn Val Gly Asp Ser Arg Ala Val Leu Ala
                165                 170                 175

Val Lys Asp Arg Asn Arg Ile Leu Ala Glu Asp Leu Ser Tyr Asp Gln
                180                 185                 190

Thr Pro Phe Arg Lys Asp Glu Cys Glu Arg Val Lys Ala Cys Gly Ala
                195                 200                 205

Arg Val Leu Ser Val Asp Gln Val Glu Gly Leu Lys Asp Pro Asn Ile
                210                 215                 220

Gln Thr Trp Ala Asn Glu Glu Ser Glu Gly Gly Asp Pro Pro Arg Leu
225                 230                 235                 240

Trp Val Gln Asn Gly Met Tyr Pro Gly Thr Ala Phe Thr Arg Ser Val
                245                 250                 255

Gly Asp Phe Thr Ala Glu Ser Ile Gly Val Ile Ala Glu Pro Glu Val
                260                 265                 270

Ser Met Val His Leu Ser Pro Asn His Leu Phe Phe Val Val Ala Ser
                275                 280                 285

Asp Gly Ile Phe Glu Phe Leu Pro Ser Gln Ala Val Val Asp Met Val
                290                 295                 300

Gly Arg Tyr Ala Asp Pro Arg Asp Gly Cys Ala Ala Ala Ala Ala Glu
305                 310                 315                 320

Ser Tyr Lys Leu Trp Leu Glu His Glu Asn Arg Thr Asp Asp Ile Thr
                325                 330                 335

Ile Ile Ile Val Gln Ile Lys Lys Leu Ser Asn Glu
                340                 345
```

GENE FOR INCREASING THE PRODUCTION OF PLANT BIOMASS AND/OR SEEDS AND METHOD FOR USE THEREOF

CROSS REFERENCE TO RELATED APPLICATIONS

This application is a National Stage of International Application No. PCT/JP2010/053939 filed Mar. 10, 2010, claiming priority based on Japanese Patent Application No. 2009-060154 filed Mar. 12, 2009, the contents of all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 9, 2014, is named Q126444_PH-3948PCT-USrev.txt and is 238,642 bytes in size.

TECHNICAL FIELD

The present invention relates to: a plant into which a given gene is introduced or an expression control region of an endogenous gene corresponding to the given gene is modified; a method for increasing the production of biomass and/or seeds through introduction of a given gene or modification of an expression control region of an endogenous gene corresponding to the given gene; and a method for producing a plant capable of producing an increased amount of biomass and/or seeds.

BACKGROUND ART

The term "biomass" generally refers to the total amount of organisms that inhabit or exist in a given area. When such term is used with regard to plants, in particular, it refers to dry weight per unit area. Biomass units are quantified in terms of mass or energy. The expression "biomass" is synonymous with "Seibutsutairyo" or "Seibutsuryo." In the case of plant biomass, the term "standing crop" is occasionally used for "biomass." Since plant biomass is generated by fixing atmospheric carbon dioxide with the use of solar energy, it can be regarded as so-called "carbon-neutral energy." Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

In particular, an energy crop such as sugar cane can be used as a raw material for biofuel. Hence, the increased production of the total mass of a plant itself (the amount of plant biomass) is expected. Under such circumstances, improvement in productivity per unit of cultivation area is required in order to increase the production of the amount of plant biomass. It has been found that if the number of cultivated plants is assumed to be constant per unit of cultivation area, improvement in the amount of biomass per plant would be necessary.

However, it is thought that since many genes are involved in the amount of plant biomass (a so-called "kind of quantitative trait"), individual gene introduction or individual genetic modification cannot lead to an effective increase in production. Meanwhile, a great deal of difficulties are associated with introduction of many genes in a desired state into a plant. Such gene introduction is also problematic in that if successful introduction takes place, desirable traits cannot always be acquired.

Various gene introduction techniques are known as techniques for increasing the production of plant biomass, as disclosed in Patent Documents 1-7, for example. However, none of these techniques can be said to exhibit sufficient effects of increasing the production of biomass.

Also, patent document 8 discloses a transformed plant with improved growth potential and disease resistance through overexpression of a glutathione-binding plastid-type fructose 1,6-bisphosphate aldolase gene (FBA1 gene).

PRIOR ART DOCUMENTS

Patent Documents

[Patent Document 1] JP Patent Publication (Kohyo) No. 2001-505410 A
[Patent Document 2] JP Patent Publication (Kohyo) No. 2001-519659 A
[Patent Document 3] JP Patent Publication (Kohyo) No. 2007-530063 A
[Patent Document 4] JP Patent Publication (Kokai) No. 2005-130770 A
[Patent Document 5] JP Patent Publication (Kohyo) No. 2000-515020 A
[Patent Document 6] JP Patent Publication (Kohyo) No. 9-503389 A (1997)
[Patent Document 7] JP Patent Publication (Kokai) No. 2005-52114 A
[Patent Document 8] WO2007/091634

SUMMARY OF THE INVENTION

Object to be Achieved by the Invention

In view of the above circumstances, an object of the present invention is to search for genes having novel functions of drastically improving the amount of plant biomass and thus to provide a technique with which the production of plant biomass can be drastically increased.

Means to Achieve the Object

As a result of intensive studies to achieve the above object, the present inventors have made the novel finding that the production of plant biomass can be drastically increased by introducing a gene encoding protein phosphatase 2C having characteristic consensus sequences and a gene encoding glutathione-binding plastid-type fructose 1,6-bisphosphate aldolase, or modifying an expression control region of endogenous genes corresponding to the genes. Thus, they have completed the present invention.

Specifically, the plant according to the present invention is a plant in which a gene encoding protein phosphatase 2C having 3 consensus sequences comprising the amino acid sequences shown in SEQ ID NOS: 1-3 from the N-terminal side in such order and a gene encoding glutathione-binding plastid-type fructose 1,6-bisphosphate aldolase are introduced, or an expression control region of endogenous genes corresponding to the genes is modified.

Also, the method for increasing the production of biomass according to the present invention comprises introducing a gene encoding protein phosphatase 2C having 3 consensus sequences comprising the amino acid sequences shown in SEQ ID NOS: 1-3 from the N-terminal side in such order and a gene encoding glutathione-binding plastid-type fructose 1,6-bisphosphate aldolase, or modifying an expression control region of endogenous genes corresponding to the genes.

Furthermore, the method for producing a plant according to the present invention comprises the steps of: preparing a transformed plant in which a gene encoding protein phosphatase 2C having 3 consensus sequences comprising the amino acid sequences shown in SEQ ID NOS: 1-3 from the N-terminal side in such order and a gene encoding glutathione-binding plastid-type fructose 1,6-bisphosphate aldolase are introduced, or an expression control region of endogenous genes corresponding to the genes is modified; and measuring the amount of biomass of a progeny plant of the transformed plant and then selecting a line in which the amount of biomass is significantly improved.

In the present invention, the above gene encoding protein phosphatase 2C can be at least one type of gene selected from the group consisting of At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270, or a gene functionally equivalent thereto.

In the present invention, the gene encoding protein phosphatase 2C preferably encodes any one of the following proteins (a) to (c):
(a) a protein comprising the amino acid sequence shown in SEQ ID NO: 5;
(b) a protein comprising an amino acid sequence that has a deletion, a substitution, an addition, or an insertion of one or a plurality of amino acids with respect to the amino acid sequence shown in SEQ ID NO: 5 and having protein phosphatase 2C activity; and
(c) a protein that is encoded by a polynucleotide hybridizing under stringent conditions to a polynucleotide comprising a nucleotide sequence complementary to the nucleotide sequence shown in SEQ ID NO: 4 and has protein phosphatase 2C activity.

Also, in the present invention, an example of the above functionally equivalent gene is a protein phosphatase 2C gene from an organism other than *Arabidopsis thaliana*. Another example of an organism other than *Arabidopsis thaliana* is one type of organism selected from the group consisting of rice (*Oryza sativa*), black cottonwood (*Populus trichocarpa*), European grape (*Vitis vinifera*), Medicago truncatula (*Medicago truncatula*), alfalfa (*Medicago sativa*), Physcomitrella patens (*Physcomitrella patens*), ice plant (*Mesembryanthemum crystallinum*), Chlamydomonas reinhardtii (*Chlamydomonas reinhardtii*), corn (*Zea mays*), rapeseed (*Brassica rapa*), tomato (*Solanum lycopersicum*), monkey flower (*Mimulus guttatus*), and monocellular red alga (*Cyanidioschyzon merolae*).

In the present invention, the above gene encoding glutathione-binding plastid-type fructose 1,6-bisphosphate aldolase can be an At2g01140 gene or a gene functionally equivalent to the gene.

In the present invention, the gene encoding glutathione-binding plastid-type fructose 1,6-bisphosphate aldolase preferably encodes any one of the following proteins (a) to (c):
(a) a protein comprising the amino acid sequence shown in SEQ ID NO: 32;
(b) a protein comprising an amino acid sequence that has a deletion, a substitution, an addition, or an insertion of one or a plurality of amino acids with respect to the amino acid sequence shown in SEQ ID NO: 32 and exhibiting fructose 1,6-bisphosphate aldolase activity as a result of binding of glutathione; and
(c) a protein that is encoded by a polynucleotide hybridizing under stringent conditions to a polynucleotide comprising a nucleotide sequence complementary to the nucleotide sequence shown in SEQ ID NO: 31 and exhibits fructose 1,6-bisphosphate aldolase activity as a result of binding of glutathione.

Also, in the present invention, an example of the above functionally equivalent gene is a glutathione-binding plastid-type fructose 1,6-bisphosphate aldolase gene from an organism other than *Arabidopsis thaliana*. Another example of an organism other than *Arabidopsis thaliana* is one type of organism selected from the group consisting of rice (*Oryza sativa*), European grape (*Vitis vinifera*), castor-oil plant (*Ricinus communis*), black cottonwood (*Populus trichocarpa*), sitka spruce (*Picea sitchensis*), and corn (*Zea mays*).

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

This description hereby incorporates the entire content of the description and/or the drawings of Japanese Patent Application No. 2009-060154, which is the basis of the priority claim of this application.

Effect of the Invention

The plant according to the present invention is a plant capable of producing significantly improved amount of biomass and/or seeds compared with wild-type plants. Also, the method for increasing the production of biomass and/or seeds according to the present invention can realize the significantly increased production of biomass and/or seeds compared with target wild-type plants. Furthermore, the method for producing a plant according to the present invention makes it possible to produce a plant capable of producing significantly improved amount of biomass and/or seeds compared with wild-type plants. Therefore, through application of the present invention, for example, productivity can be improved when the plant itself is a product and this can be achieved at lower cost. Also, through application of the present invention, for example, the productivity can be improved when seeds are directly products or ingredients contained in seeds are directly products and this can be achieved at lower cost.

BRIEF DESCRIPTION OF THE DRAWINGS

FIG. 1-1 is a characteristic diagram showing the results of alignment analysis using a CLUSTAL W (1.83) multiple sequence alignment program for amino acid sequences encoded by At1g03590-AtPP2C6-6 (SEQ ID NO:57), At1g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53), At4g32950 (SEQ ID NO:54), At3g16800 (SEQ ID NO:62), At3g05640 (SEQ ID NO: 5), At5g27930-AtPP2C6-7 (SEQ ID NO:61), At2g20050 (SEQ ID NO:63), and At3g06270 (SEQ ID NO:64).

FIG. 1-2 is a characteristic diagram showing the results of alignment analysis using a CLUSTAL W (1.83) multiple sequence alignment program for amino acid sequences encoded by At1g03590-AtPP2C6-6 ( SEQ ID NO:57), At1 g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53) At4g32950 (SEQ ID NO:54), At3g16800 (SEQ ID NO:62), At3g05640 (SEQ ID NO:5), At5g27930-AtPP2C6-7 (SEQ ID NO:61), At2g20050 (SEQ ID NO:63), and At3g06270 (SEQ ID NO:64).

FIG. 1-3 is a characteristic diagram showing the results of alignment analysis using a CLUSTAL W (1.83) multiple sequence alignment program for amino acid sequences encoded by At1g03590-AtPP2C6-6 (SEQ ID NO:57), At1g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53), At4g32950 (SEQ ID NO:54), At3g16800 (SEQ ID NO:62), At3g05640 (SEQ ID NO: 5), At5g27930-AtPP2C6-7 (SEQ ID NO:61), At2g20050 (SEQ ID NO:63), and At3g06270 (SEQ ID NO:64).

FIG. 2-1 is a characteristic diagram showing the results of alignment analysis using a CLUSTAL W (1.83) multiple sequence alignment program for amino acid sequences encoded by At1g03590-AtPP2C6-6 (SEQ ID NO:57), At1g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53), At4g32950 (SEQ ID NO:54), At3g16800 (SEQ ID NO:62), At3g05640 (SEQ ID NO: 5), At5g27930-AtPP2C6-7 (SEQ ID NO:61), At2g20050 (SEQ ID NO:63), and At3g06270 (SEQ ID NO:64).

FIG. 2-2 is a characteristic diagram showing the results of alignment analysis using a CLUSTAL W (1.83) multiple sequence alignment program for amino acid sequences encoded by At1g03590-AtPP2C6-6 (SEQ ID NO:57), At1g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53), At4g32950 (SEQ ID NO:54), At3g16800 (SEQ ID NO:62), At3g05640 (SEQ ID NO: 5), At5g27930-AtPP2C6-7 (SEQ ID NO:61), At2g20050 (SEQ ID NO:63), and At3g06270 (SEQ ID NO:64).

FIG. 2-3 is a characteristic diagram showing the results of alignment analysis using a CLUSTAL W (1.83) multiple sequence alignment program for amino acid sequences encoded by At1g03590-AtPP2C6-6 (SEQ ID NO:57), At1g16220 (SEQ ID NO:55), At1g79630 (SEQ ID NO:56), At5g01700 (SEQ ID NO:60), At3g02750 (SEQ ID NO:58), At5g36250 (SEQ ID NO:59), At5g26010 (SEQ ID NO:53), At4g32950 (SEQ ID NO:54), At3g16800 (SEQ ID NO:62), At3g05640 (SEQ ID NO: 5), At5g27930-AtPP2C6-7 (SEQ ID NO:61), At2g20050 (SEQ ID NO:63), and At3g06270 (SEQ ID NO:64).

FIG. 3-1 is a characteristic diagram showing the results of alignment analysis using a CLUSTAL W (1.83) multiple sequence alignment program for amino acid sequences encoded by EEF02079 (SEQ ID NO: 36), ABK94899 (SEQ ID NO: 37), EEE88847 (SEQ ID NO: 38), EEF36097 (SEQ ID NO: 39), CA042215 (SEQ ID NO: 40), At2g01140, ABK24286 (SEQ ID NO: 33), ABK25226 (SEQ ID NO: 34), ABK24568 (SEQ ID NO: 35), ACG47464 (SEQ ID NO: 41), ACG47669 (SEQ ID NO: 42), and Os01g0118000 (SEQ ID NO: 43).

FIG. 3-2 is a characteristic diagram showing the results of alignment analysis using a CLUSTAL W (1.83) multiple sequence alignment program for amino acid sequences encoded by EEF02079 (SEQ ID NO: 36), ABK94899 (SEQ ID NO: 37), EEE88847 (SEQ ID NO: 38), EEF36097 (SEQ ID NO: 39), CA042215 (SEQ ID NO: 40), At2g01140, ABK24286 (SEQ ID NO: 33), ABK25226 (SEQ ID NO: 34), ABK24568 (SEQ ID NO: 35), ACG47464 (SEQ ID NO: 41), ACG47669 (SEQ ID NO: 42), and Os01g0118000 (SEQ ID NO: 43)

BEST MODE FOR CARRYING OUT THE INVENTION

Figure 4:
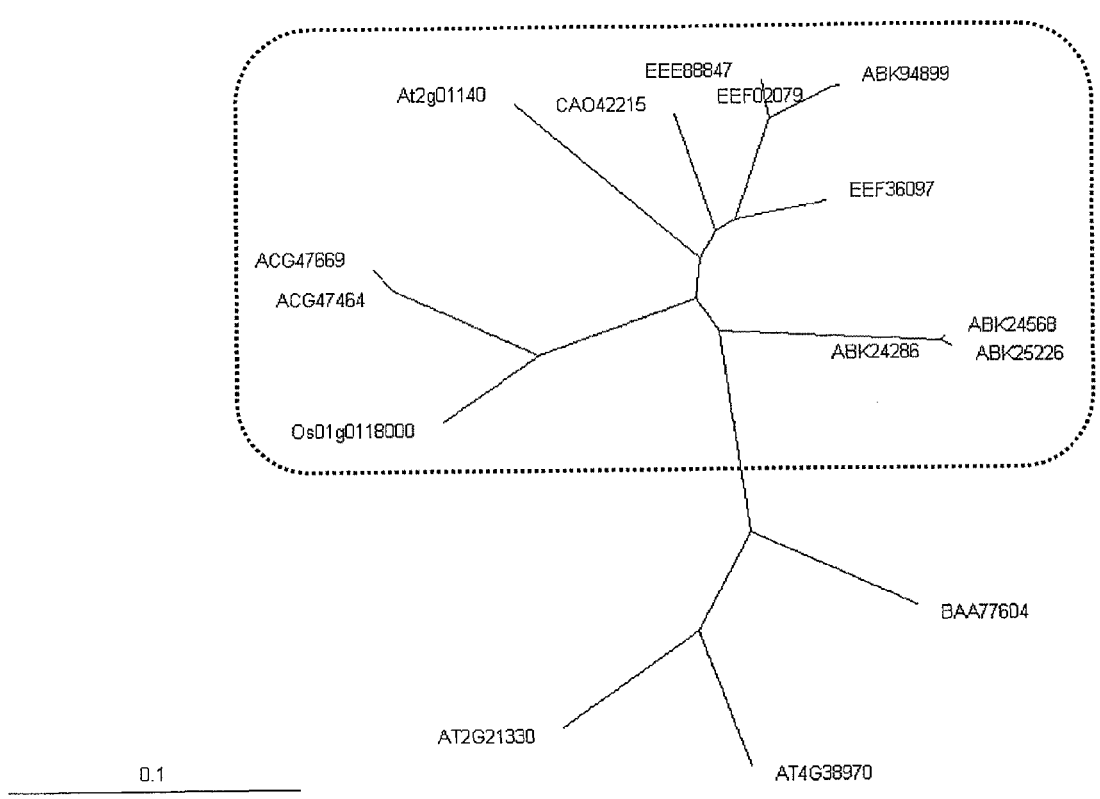
FIG. 4 is a phylogenetic tree created for EEF02079, ABK94899, EEE88847, EEF36097, CAO42215, At2g01140, ABK24286, ABK25226, ABK24568, ACG47464, ACG47669, Os01g0118000, At4g38970, At2g21330, and BAA77604.

The present invention will be described in detail as follows.

The plant according to the present invention is produced by introducing a gene encoding protein phosphatase 2C having characteristic consensus sequences and a gene encoding glutathione-binding plastid-type fructose 1,6-bisphosphate aldolase or modifying an expression control region of endogenous genes corresponding to the genes, wherein the amount of biomass is significantly improved compared with wild-type plants. The expression level of a target gene can be significantly increased compared with that in a wild-type plant by exogenously introducing the target gene into plants or modifying an expression control region of an endogenous gene corresponding to the gene. The plant according to the present invention may be produced by causing the expression of the protein phosphatase 2C gene and the glutathione-binding plastid-type fructose 1,6-bisphosphate aldolase gene in all plant tissues, or at least in some plant tissues. Here, the term "plant tissue(s)" is meant to include plant organ(s) such as leaves, stems, seeds, roots, and flowers.

Also, the term "expression control region" refers to a promoter region to which RNA polymerase binds and a region to which another transcription factor binds. A transcriptional regulatory region is preferably modified by substituting a promoter region, for example, among endogenous transcriptional regulatory regions with a promoter region that enables a higher expression level.

Protein Phosphatase 2C Gene

In the present invention, the protein phosphatase 2C gene encodes protein phosphatase 2C that has 3 consensus sequences comprising the amino acid sequences shown in SEQ ID NOS: 1-3 from the N-terminal side in such order. In addition, a gene group classified as Group E as in FIG. 1 of Topographic cladogram (on page 237 of Reference: TRENDS in Plant Science Vol. 9 No. 5 May 2004 pages 236-243) encodes protein phosphatase 2C having 3 consensus sequences comprising the amino acid sequences shown in SEQ ID NOS: 1-3 from the N-terminal side in such order. In addition, the reference predicts the presence of 76 protein phosphatase 2C genes in *Arabidopsis thaliana* and discloses the results of producing a phylogenetic tree of these genes using T-Coffee software (reference; Notredame, C. et al. 2000 T-Coffee: a novel method for fast and accurate multiple sequence alignment. J. Mol. Biol. 302, 205-247) as in FIG. 1. In this phylogenetic tree, protein phosphatase 2C genes classified as members of Group E encode protein phosphatase 2C that has 3 consensus sequences comprising the amino acid sequences shown in SEQ ID NOS: 1-3 from the N-terminal side in such order. The 3 consensus sequences comprising the amino acid sequences shown in SEQ ID NOS: 1-3 are characteristic sequences in Group E in the above-mentioned classification and serve as a basis for clear differentiation from other groups.

Group E in the above classification includes protein phosphatase 2C genes specified by Arabidopsis thaliana-derived At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270. FIG. 1 shows the results of alignment analysis using a CLUSTAL W (1.83) multiple sequence alignment program (which can be used with the DDBJ of the National Institute of Genetics (clustalw.ddbj.nig.ac.jp/top-j.html)) for the amino acid sequences encoded by these Arabidopsis thaliana-derived protein phosphatase 2C genes, Atp1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050 and At3g06270 (with the amino acid (sequence) substitution matrix used herein being a default matrix known as BLOSUM (Blocks of Amino Acid Substitution Matrix)). As shown in FIG. 1, these protein phosphatase 2C genes classified as members of Group E have consensus sequences characteristic in the regions denoted as I to III. These regions denoted as I to III are subjected with a rice-derived protein phosphatase 2C gene (described later) to alignment analysis, so that the 3 consensus sequences comprising the amino acid sequences shown in SEQ ID NOS: 1-3 can be defined.

Herein, in the amino acid sequence shown in SEQ ID NO: 1, which is an amino acid residue denoted as "Xaa," may be any amino acid, and it is not limited to any particular amino acid. However, the 1st amino acid residue from the N-terminal side in the amino acid sequence shown in SEQ ID NO: 1 is preferably leucine (three character code: Leu and single character code: L; the same applies to the following) or phenylalanine (Phe, F). The 4th amino acid residue from the N-terminal side in the amino acid sequence shown in SEQ ID NO: 1 is preferably valine (Val, V), isoleucine (Ile, I), or methionine (Met, M). The 16th amino acid residue from the N-terminal side in the amino acid sequence shown in SEQ ID NO: 1 is preferably serine (Ser, S) or alanine (Ala, A). The 17th amino acid residue from the N-terminal side in the amino acid sequence shown in SEQ ID NO: 1 is preferably lysine (Lys, K), arginine (Arg, R), glutamine (Gln, Q), or asparagine (Asn, N). More specifically, a consensus sequence comprising the amino acid sequence shown in SEQ ID NO: 1 is preferably (L/F)XG(V/I/M)FDGH-GXXGXXX(S/A)(K/R/Q/N)XV. In such amino acid sequence, pluralities of amino acids in parentheses represent possible variations of amino acid residues at the relevant positions. Also, in the following amino acid sequences, "X" means that any amino acid residue may be present at the relevant position.

Also, such a consensus sequence may be a sequence containing the following 3 amino acid residues on the N-terminal side of Region I in FIG. 1: (D/E/N)XX.

Here, in the amino acid sequence shown in SEQ ID NO: 2, an amino acid residue denoted as "Xaa," may be any amino acid, and it is not limited to any particular amino acid. However, the 5th amino acid residue from the N-terminal side in the amino acid sequence shown in SEQ ID NO: 2 is preferably glycine (Gly, G), alanine (Ala, A), or serine (Ser, S). The 6th amino acid residue from the N-terminal side in the amino acid sequence shown in SEQ ID NO: 2 is preferably valine (Val, V), leucine (Leu, L), or isoleucine (Ile, I). The 9th amino acid residue from the N-terminal side in the amino acid sequence shown in SEQ ID NO: 2 is preferably isoleucine (Ile, I), valine (Val, V), phenylalanine (Phe, F), methionine (Met, M), or leucine (Leu, L). The 12th amino acid residue from the N-terminal side in the amino acid sequence shown in SEQ ID NO: 2 is preferably glycine (Gly, G) or alanine (Ala, A). The 15th amino acid residue from the N-terminal side in the amino acid sequence shown in SEQ ID NO: 2 is preferably leucine (Leu, L), valine (Val, V), or isoleucine (Ile, I). The 17th amino acid residue from the N-terminal side in the amino acid sequence shown in SEQ ID NO: 2 is preferably isoleucine (Ile, I), valine (Val, V), or methionine (Met, M). The 18th amino acid residue from the N-terminal side in the amino acid sequence shown in SEQ ID NO: 2 is preferably glycine (Gly, G) or alanine (Ala, A). The 22nd amino acid residue from the N-terminal side in the amino acid sequence shown in SEQ ID NO: 2 is preferably aspartic acid (Asp, D) or histidine (His, H). The 26th amino acid residue from the N-terminal side in the amino acid sequence shown in SEQ ID NO: 2 is preferably valine (Val, V) or isoleucine (Ile, I). The 27th amino acid residue from the N-terminal side in the amino acid sequence shown in SEQ ID NO: 2 is preferably leucine (Leu, L), methionine (Met, M), or isoleucine (Ile, I). More specifically, a consensus sequence comprising the amino acid sequence shown in SEQ ID NO: 2 is preferably SGXT(G/A/S)(V/L/I)XX(I/V/F/M/L)XX(G/A)XX(L/V/I)X(I/V/M)(A/G)NXG(D/H)SRA(V/I)(L/M/I). In such amino acid sequence, pluralities of amino acids in parentheses represent possible variations of amino acid residues at the relevant positions. Also, in the following amino acid sequences, "X" means that any amino acid residue may be present at the relevant position.

Here, the amino acid sequence shown in SEQ ID NO: 3, an amino acid residue denoted as "Xaa," may be any amino acid, and it is not limited to any particular amino acid. However, the 4th amino acid residue from the N-terminal side in the amino acid sequence shown in SEQ ID NO: 3 is preferably methionine (Met, M), valine (Val, V), or phenylalanine (Phe, F). The 5th amino acid residue from the N-terminal side in the amino acid sequence shown in SEQ ID NO: 3 is preferably serine (Ser, S), alanine (Ala, A), or threonine (Thr, T). The 7th amino acid residue from the N-terminal side in the amino acid sequence shown in SEQ ID NO: 3 is preferably alanine (Ala, A) or serine (Ser, S). The 8th amino acid residue from the N-terminal side in the amino acid sequence shown in SEQ ID NO: 3 is preferably phenylalanine (Phe, F), isoleucine (Ile, I), or valine (Val, V). The 14th amino acid residue from the N-terminal side in the amino acid sequence shown in SEQ ID NO: 3 is preferably lysine (Lys, K) or glutamic acid (Glu, E). The 18th amino acid residue from the N-terminal side in the amino acid sequence shown in SEQ ID NO: 3 is preferably valine (Val, V) or leucine (Leu, L). The 19th amino acid residue from the N-terminal side in the amino acid sequence shown in SEQ ID NO: 3 is preferably isoleucine (Ile, I) or valine (Val, V). The 23rd amino acid residue from the N-terminal side in the amino acid sequence shown in SEQ ID NO: 3 is preferably glutamic acid (Glu, E), glutamine (Gln, Q), or aspartic acid (Asp, D). The 24th amino acid residue from the N-terminal side in the amino acid sequence shown in SEQ ID NO: 3 is preferably isoleucine (Ile, I), valine (Val, V), or phenylalanine (Phe, F). The 29th amino acid residue from the N-terminal side in the amino acid sequence shown in SEQ ID NO: 3 is preferably isoleucine (Ile, I), leucine (Leu, L), or valine (Val, V). The 30th amino acid residue from the N-terminal side in the amino acid sequence shown in SEQ ID NO: 3 is preferably serine (Ser, S), threonine (Thr, T), or asparagine (Asn, N). The 33rd amino acid residue from the N-terminal side in the amino acid sequence shown in SEQ ID NO: 3 is preferably aspartic acid (Asp, D), asparagine (Asn, N), or histidine (His, H). The 35th amino acid residue from the N-terminal side in the amino acid sequence shown in SEQ ID NO: 3 is preferably phenylalanine (Phe, F) or tyrosine (Tyr, Y). The 36th amino acid residue from the N-terminal side in the amino acid sequence shown in SEQ ID NO: 3 is preferably leucine (Leu, L), isoleucine (Ile, I), valine (Val, V), phenylalanine (Phe, F), or methionine (Met, M). The 37th amino acid residue from the N-terminal side in the amino acid sequence shown in SEQ ID NO: 3 is preferably valine (Val, V), leucine (Leu, L), or isoleucine (Ile, I). The 38th amino acid residue from the N-terminal side in the amino acid sequence shown in SEQ ID NO: 3 is preferably leucine (Leu, L) or valine (Val, V). The 40th amino acid residue from the N-terminal side in the amino acid sequence shown in SEQ ID NO: 3 is preferably threonine (Thr, T) or serine (Ser, S). The 43rd amino acid residue from the N-terminal side in the amino acid sequence shown in SEQ ID NO: 3 is preferably valine (Val, V), isoleucine (Ile, I), or methionine (Met, M). The 44th amino acid residue from the N-terminal side in the amino acid sequence shown in SEQ ID NO: 3 is preferably tryptophan (Trp, W) or phenylalanine (Phe, F). The 45th amino acid residue from the N-terminal side in the amino acid sequence shown in SEQ ID NO: 3 is preferably aspartic acid (Asp, D) or glutamic acid (Glu, E). The 47th amino acid residue from the N-terminal side in the amino acid sequence shown in SEQ ID NO: 3 is preferably leucine (Leu, L), isoleucine (Ile, I), or methionine (Met, M). The 48th amino acid residue from the N-terminal side in the amino acid sequence shown in SEQ ID NO: 3 is preferably serine (Ser, S), threonine (Thr, T), or proline (Pro, P). The 49th amino acid residue from the N-terminal side in the amino acid sequence shown in SEQ ID NO: 3 is preferably asparagine (Asn, N) or serine (Ser, S). The 52nd amino acid residue from the N-terminal side in the amino acid sequence shown in SEQ ID NO: 3 is preferably valine (Val, V) or alanine (Ala, A). The 55th amino acid residue from the N-terminal side in the amino acid sequence shown in SEQ ID NO: 3 is preferably leucine (Leu, L), valine (Val, V), isoleucine (Ile, I), or methionine (Met, M). The 56th amino acid residue from the N-terminal side in the amino acid sequence shown in SEQ ID NO: 3 is preferably isoleucine (Ile, I) or valine (Val, V). Preferably, an example of the consensus sequence comprising the amino acid sequence shown in SEQ ID NO: 3 is more specifically GXA(M/V/F)(S/A/T)R(A/S)(F/I/V)GDXXX(K/E)XXG(V/L)(I/V)XXP(E/Q/D)(I/V/F)XXXX (I/L/V)(T/S)XX(D/N/H)X(F/Y)(L/I/V/F)(V/L/I)(L/V)A(T/S)DG(V/I/M)(W/F)(D/E)X(L/I/M)(S/T/P)(N/S)XX(V/A)XX(L/V/I/M)(I/V). In such amino acid sequence, pluralities of amino acids in parentheses represent possible variations of amino acid residues at the relevant positions. Also, in the following amino acid sequences, "X" means that any amino acid residue may be present at the relevant position.

Here, the 20th amino acid residue from the N-terminal side in the amino acid sequence shown in SEQ ID NO: 3 is more preferably alanine (Ala, A), serine (Ser, S), or cysteine (Cys, C). Also, the 50th amino acid residue from the N-terminal side in the amino acid sequence shown in SEQ ID NO: 3 is more preferably aspartic acid (Asp, D), glutamic acid (Glu, E), lysine (Lys, K), glutamine (Gln, Q), or asparagine (Asn, N).

Variations of amino acid residues that can be present at given positions are determined based on the following reasons. As described in Reference (1) ("McKee Biochemistry," 3rd ed., Chapter 5 Amino Acid.Peptide Protein 5.1 Amino Acid; editorial supervisor: Atsushi Ichikawa; translation supervisor: Shinichi Fukuoka; publisher: Ryosuke Sone; publishing office: Kagaku-Dojin Publishing Company, INC <kagakudojin.co.jp/profile/english.html>, ISBN4-7598-0944-9), it is well known that amino acids are classified based on side chains having similar properties (e.g., chemical properties and physical sizes). Also, it is well known that molecular evolutionary substitution frequently takes place among amino acid residues classified in a given group, while retaining protein activity. Based on these concepts, a substitution (mutation) score matrix for amino acid residues (BLOSUM: Blocks of Amino Acid Substitution Matrix) is proposed in FIG. 2 of Reference (2): Henikoff S., Henikoff J. G., Amino-acid substitution matrices from protein blocks, Proc. Natl. Acad. Sci. U.S.A., 89, 10915-10919 (1992) and is broadly used. Reference (2) is based on a finding that amino acid substitutions that take place among amino acids with side chains having similar chemical properties result in less structural or functional changes in the entire protein. According to References (1) and (2) above, amino acid side chain groups to be used in multiple alignment can be considered based on indices such as chemical properties and physical sizes. They are shown as amino acid groups with a score of 0 or higher and preferably as amino acid groups with a score of 1 or higher through the use of the score matrix (BLOSUM) disclosed in Reference (2). Typical groups are the following 8 groups. Further precisely grouped amino acid groups may be amino acid groups with a score of 0 or higher, preferably a score of 1 or higher, and further preferably a score of 2 or higher.

1) Aliphatic Hydrophobic Amino Acid Group (ILMV Group)

This group is a group of amino acids having aliphatic hydrophobic side chains, among neutral nonpolar amino acids disclosed in Reference (1) above, which is composed of V (Val, valine), L (Leu, leucine), I (Ile, isoleucine), and M (Met, methionine). Among amino acids classified as neutral nonpolar amino acids according to Reference (1), FGACWP is not included in this "aliphatic hydrophobic amino acid group" because of the following reasons: G (Gly, glycine) and A (Ala, alanine) are the same size as that of or smaller in size than a methyl group and have weak non polar effects; C (Cys, cysteine) may play an important role in S—S bonds and has a property of forming a hydrogen bond with an oxygen atom or a nitrogen atom; F (Phe, phenylalanine) and W (Trp, tryptophan) have side chains with significantly large molecular weights and have strong aromatic effects; P (Pro, proline) has strong imino acid effects, so as to fix the angle of the main chain of the polypeptide.

2) Group Having Hydroxymethylene Group (ST Group)

This group is a group of amino acids (from among neutral polar amino acids) having hydroxymethylene groups in side chains, which is composed of S (Ser, serine) and T (Thr, threonine). Hydroxy groups existing in the side chains of S and T constitute sugar-binding sites, so that these sites are often important for a polypeptide (protein) to have specific activity.

3) Acidic Amino Acid (DE Group)

This group is a group of amino acids having acidic carboxyl groups in side chains, which is composed of D (Asp, aspartic acid) and E (Glu, glutamic acid).

4) Basic Amino Acid (KR Group)

This group is a group of basic amino acids, which is composed of K (Lys, lysine) and R (Arg, arginine). These K and R are positively charged within a wide pH range and have basic properties. On the other hand, H (His, histidine) classified in basic amino acids is almost never ionized at pH 7, so that His not classified in this group.

5) Methylene Group=Polar Group (DHN Group)

This group is characterized in that: in all cases, a methylene group as a side chain binds to an α-carbon element beyond which a polar group is present; and the physical sizes of methylene groups (nonpolar groups) closely resemble from each other. This group is composed of N (Asn, asparagine; polar group is an amide group), D (Asp, aspartic acid; polar groups are carboxyl groups), and H (His, histidine; polar groups are imidazole groups).

6) Dimethylene Group=Polar Group (EKQR Group)

This group is characterized in that: in all cases, linear hydrocarbon having a length longer than that of a dimethylene group binds as a side chain to an α-carbon element, beyond which a polar group is present; and the physical sizes of dimethylene groups that are nonpolar groups closely resemble from each other. This group is composed of E (Glu, glutamic acid, polar group is a carboxyl group), K (Lys, lysine; polar groups are amino groups), Q (Gln, glutamine; polar groups are amide groups), and R (Arg, arginine; polar groups are imino groups and amino groups).

7) Aromatic Series (FYW Group)

This group is a group of aromatic amino acids having benzene nuclei in the side chains and characterized by having chemical properties unique in aromatic series. This group is composed of F (Phe, phenylalanine), Y (Tyr, tyrosine), and W (Trp, tryptophan).

8) Ring & Polar (HY Group)

This group is a group of amino acids having both ring structures in the side chains and polarity, which is composed of H(H, histidine; Both ring structures and polar groups are imidazole groups), and Y (Tyr, tyrosine; Ring structures are benzene nuclei and polar groups are hydroxy groups).

As described above, it is understood that: in the given amino acid sequences shown in SEQ ID NOS: 1-3, an amino acid residue denoted as Xaa may be any amino acid; or amino acid residues denoted as Xaa may be substituted with each other within the above groups 1)-8). Hence, in the present invention, the protein phosphatase 2C gene to be introduced into a plant or subjected to modification of an expression control region may be a protein phosphatase 2C gene from any plant, as long as it has the 3 consensus sequences comprising the amino acid sequences shown in SEQ ID NOS: 1-3 from the N-terminal side in such order.

More specifically, examples of an *Arabidopsis thaliana* protein phosphatase 2C-coding gene having the 3 consensus sequences (comprising the amino acid sequences shown in SEQ ID NOS: 1-3) from the N-terminal side in such order include At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270. In the present invention, at least one type of gene selected from the gene group is introduced into a plant or an expression control region of an endogenous gene corresponding to the gene is modified. Particularly in the present invention, it is preferable to introduce at least one type of gene selected from among At1g03590-AtPP2C6-6, At1g16220, At1g79630, At5g01700, At3g02750, At5g36250, At5g26010, At4g32950, At3g16800, At3g05640, and At5g27930-AtPP2C6-7 into a plant, or to modify an expression control region of an endogenous gene corresponding to the gene. Particularly, in the present invention, it is more preferable to introduce at least one type of gene selected from among At3g16800, At3g05640, and At5g27930-AtPP2C6-7 into a plant, or to modify the expression control region of the endogenous gene corresponding to the gene. It is most preferable to introduce the gene specified by At3g05640 into a plant or to modify an expression control region of an endogenous gene corresponding to the gene.

In addition, FIG. 2 shows the results of alignment analysis using a CLUSTAL W (1.83) multiple sequence alignment program (that can be used with the DDBJ of the National Institute of Genetics (clustalw.ddbj.nig.ac.jp/top-j.html)) for amino acid sequences encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7 (amino acid (sequence) substitution matrix used herein is default matrix, BLOSUM (Blocks of Amino Acid Substitution Matrix)).

That is, FIG. 2 shows the 3 consensus sequences in protein phosphatase 2C encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7. Regions denoted as I-III in FIG. 2 are subjected with an ortholog of a rice-derived protein phosphatase 2C gene (described later) to alignment analysis, so that the 3 consensus sequences comprising the amino acid sequences shown in SEQ ID NOS: 1-3 above can be defined as the 3 consensus sequences comprising the amino acid sequences shown in SEQ ID NOS: 48-55, respectively.

The consensus sequence shown in SEQ ID NO: 48 is more specifically (L/F)CG(V/I/M)FDGHGXXGXX(V/I)(S/A)(K/R)XV. The consensus sequence shown in SEQ ID NO: 49 is more specifically SGXT(G/A/S)(V/L)XX(I/V/F/L)XX(G/A)XX(L/V/I)X(I/V/M)(A/G)NXG(D/H)SRA(V/I)(L/M/I). The consensus sequence shown in SEQ ID NO: 50 is more specifically GLA(M/V)(S/A)R(A/S)(F/L)GDXX(L/I/V)KX(Y/F/H)G(V/L)(I/V)XXP(E/Q/D)(I/V/F)XXX X(I/L/V)(T/S)XXDX(F/Y)(L/I/V/M)(V/L/I)LA(T/S)DG(V/I/M)WDX(L/I/M/V)(S/T)NX(E/D)(V/A)XX(L/V/I)(I/V).

In addition, in such amino acid sequences, pluralities of amino acids in parentheses represent possible variations of amino acid residues at the relevant positions. Also, in these amino acid sequences, "X" means that any amino acid residue may be present at the relevant position.

Here, the 9th amino acid residue from the N-terminal side in the amino acid sequence shown in SEQ ID NO: 49 is more preferably isoleucine (Ile, I), valine (Val, V), or phenylalanine (Phe, F). Also, the 11th amino acid residue from the N-terminal side in the amino acid sequence shown in SEQ ID NO: 49 is more preferably glutamine (Gln, Q) or histidine (His, H). Moreover, the 13th amino acid residue from the N-terminal side in the amino acid sequence shown in SEQ ID NO: 49 is more preferably lysine (Lys, K), glutamic acid (Glu, E), serine (Ser, S), glutamine (Gln, Q), aspartic acid (Asp, D), or asparagine (Asn, N).

Here, the 7th amino acid residue from the N-terminal side in the amino acid sequence shown in SEQ ID NO: 50 is more preferably alanine (Ala, A). Also, the 8th amino acid residue from the N-terminal side in the amino acid sequence shown in SEQ ID NO: 50 is more preferably phenylalanine (Phe, F). Moreover, the 11th amino acid residue from the N-terminal side in the amino acid sequence shown in SEQ ID NO: 50 is more preferably phenylalanine (Phe, F) or tyrosine (Tyr, Y). Furthermore, the 13th amino acid residue from the N-terminal side in the amino acid sequence shown in SEQ ID NO: 50 is more preferably leucine (Leu, L) or isoleucine (Ile, I). Moreover, the 15th amino acid residue from the N-terminal side in the amino acid sequence shown in SEQ ID NO: 50 is more preferably aspartic acid (Asp, D), serine (Ser, S), or glutamic acid (Glu, E). Furthermore, the 20th amino acid residue from the N-terminal side in the amino acid sequence shown in SEQ ID NO: 50 is more preferably serine (Ser, S), alanine (Ala, A), or cysteine (Cys, C). Moreover, the 27th amino acid residue from the N-terminal side in the amino acid sequence shown in SEQ ID NO: 50 is more preferably histidine (His, H) or arginine (Arg, R). Furthermore, the 34th amino acid residue from the N-terminal side in the amino acid sequence shown in SEQ ID NO: 50 is more preferably glutamine (Gln, Q), glutamic acid (Glu, E), or histidine (His, H). Furthermore, the 36th amino acid residue from the N-terminal side in the amino acid sequence shown in SEQ ID NO: 50 is more preferably leucine (Leu, L), isoleucine (Ile, I), or valine (Val, V). Furthermore, the 47th amino acid residue from the N-terminal side in the amino acid sequence shown in SEQ ID NO: 50 is more preferably leucine (Leu, L), isoleucine (Ile, I), or valine (Val, V). Furthermore, the 50th amino acid residue from the N-terminal side in the amino acid sequence shown in SEQ ID NO: 50 is more preferably lysine (Lys, K), glutamic acid (Glu, E), glutamine (Gln, Q), aspartic acid (Asp, D), or asparagine (Asn, N).

As examples, the nucleotide sequence of the coding region in the gene specified by At3g05640 is shown in SEQ ID NO: 4 and the amino acid sequence of protein phosphatase 2C encoded by the gene specified by At3g05640 is shown in SEQ ID NO: 5.

Also, in the present invention, genes functionally equivalent to genes listed above may also be introduced into a plant or the expression control regions of endogenous genes corresponding to the genes may be modified. Here, the term "functionally equivalent gene" refers to, for example, a gene (from an organism other than Arabidopsis thaliana) that: has the 3 consensus sequences (preferably, the 3 consensus sequences comprising the amino acid sequences shown in SEQ ID NOS: 48-50. The same applies to the following) comprising the amino acid sequences shown in SEQ ID NOS: 1-3 from the N-terminal side in such order; and encodes protein phosphatase 2C. Also, the term "functionally equivalent gene" refers to a gene that encodes a protein having protein phosphatase 2C activity. The term "protein phosphatase 2C activity" refers to $Mg^{2+}$ or $Mn^{2+}$-dependent serine/threonine phosphatase (Ser/Thr phosphatase) activity. Therefore, whether or not a gene encodes a protein having protein phosphatase 2C activity can be confirmed by examining whether or not the gene product has serine/threonine phosphatase activity in the presence of $Mg^{2+}$ or $Mn^{2+}$. Conventionally known techniques can be appropriately employed for determining serine/threonine phosphatase activity. For example, a commercially available activity determination kit ProFluor (registered trademark) Ser/Thr Phosphatase Assay (Promega) can be used.

Here, example of organisms other than Arabidopsis thaliana is not limited. For example, rice (Oryza sativa) is included. Specifically, an example of a functionally equivalent gene is a rice Os05g0358500 gene. The nucleotide sequence of a coding region of the Os05g0358500 gene is shown in SEQ ID NO: 6 and the amino acid sequence of the protein encoded by the gene is shown in SEQ ID NO: 7. Also, examples of the above-mentioned rice-derived functionally equivalent gene include Os11g0109000 (the nucleotide sequence and the amino acid sequence are shown in SEQ ID NOS: 8 and 9, respectively), Os12g0108600 (the nucleotide sequence and the amino acid sequence are shown in SEQ ID NOS: 10 and 11, respectively), Os02g0471500 (the nucleotide sequence and the amino acid sequence are shown in SEQ ID NOS: 12 and 13, respectively), Os04g0321800 (the nucleotide sequence and the amino acid sequence are shown in SEQ ID NOS: 14 and 15, respectively), Os11g0417400 (the nucleotide sequence and the amino acid sequence are shown in SEQ ID NOS: 16 and 17, respectively), Os07g0566200 (the nucleotide sequence and the amino acid sequence are shown in SEQ ID NOS: 18 and 19, respectively), Os08g0500300 (the nucleotide sequence and the amino acid sequence are shown in SEQ ID NOS: 20 and 21, respectively), Os02g0224100 (the nucleotide sequence and the amino acid sequence are shown in SEQ ID NOS: 22 and 23, respectively), and Os02g0281000 (the nucleotide sequence and the amino acid sequence are shown in SEQ ID NOS: 51 and 52, respectively).

Moreover, examples of the above-mentioned functionally equivalent genes from plants other than Arabidopsis thaliana and rice include genes (UniProt data base Accession Nos. A9P973, A9 PFS0, and A9P7U4) from black cottonwood (Populus trichocarpa), genes (UniProt data base Accession Nos. A7PRZ8, A7Q8H4, A7PV59, A5C3B0, A5BF43, A7QFG6, A7P4H7, A5C0C9, A5AP53, A7QQF9, and A5BDP5) from European grape (*Vitis vinifera*), genes (UniProt data base Accession Nos. Q2HW33 and Q4L0F8) from *Medicago truncatula* (*Medicago truncatula*), a gene (GenBank data base Accession No. AY651248) from alfalfa (*Medicago sativa*), genes (UniProt data base Accession Nos. A9SE70, A9SE69, and A9RFU1) from *Physcomitrella patens* (*Physcomitrella patens*), a gene (UniProt data base Accession No. 2511453C) from ice plant (*Mesembryanthemum crystallinum*), a gene (UniProt data base Accession No. A8HQG8) from *Chlamydomonas reinhardtii* (*Chlamydomonas reinhardtii*), genes (GenBank data base Accession Nos. BT024031, BT017414, and BT024134) from corn (*Zea mays*), genes (GenBank data base Accession Nos. AC189312 and AC189579) from rapeseed (*Brassica rapa*), genes (GenBank data base Accession Nos. AP009550, AP009302, and AP009278) from tomato (*Solanum lycopersicum*), a gene (GenBank data base Accession No. AC182571) from monkey flower (*Mimulus guttatus*), and a gene (GenBank data base Accession No. AP006489) from monocellular red alga (*Cyanidioschyzon inerolae*).

In these plants other than *Arabidopsis thaliana*, which are represented by the above examples, a gene encoding protein phosphatase 2C that has the 3 consensus sequences comprising the amino acid sequences shown in SEQ ID NOS: 1-3 from the N-terminal side in such order can be easily searched for and/or identified from a known database such as GenBank based on the above-listed nucleotide sequence of *Arabidopsis thaliana*-derived protein phosphatase 2C gene or amino acid sequence of protein phosphatase 2C.

In addition, a protein phosphatase 2C gene in the present invention is not limited to the above described protein phosphatase 2C genes comprising the nucleotide sequences and the amino acid sequences shown in SEQ ID NOS: 4-23. Hence, the protein phosphatase 2C gene may be a gene that contains an amino acid sequence having a deletion, a substitution, an addition, or an insertion of one or a plurality of amino acid sequences with respect to the amino acid sequences shown in odd numbers of SEQ ID NOS: 4-23, and, has protein phosphatase 2C activity. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by modifying a nucleotide sequence encoding the above protein phosphatase 2C gene by a technique known in the art. Mutation can be introduced into a nucleotide sequence by a known technique such as the Kunkel method or the Gapped duplex method or a method based thereof. For example, mutation is introduced with a mutagenesis kit using site-directed mutagenesis (e.g., Mutant-K or Mutant-G (both are trade names of Takara Bio)) or the like, or a LA PCR in vitro Mutagenesis series kit (trade name, Takara Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, protein phosphatase 2C genes to be used herein may be genes homologous to the protein phosphatase 2C genes comprising the nucleotide sequences and the amino acid sequences shown in SEQ ID NOS: 4-23. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes analogous to the protein phosphatase 2C genes comprising the nucleotide sequences and the amino acid sequences shown in SEQ ID NOS: 4-23 include genes encoding proteins having: amino acid sequences that have 70% or more, preferably 80% or more, more preferably 90% or more, and most preferably 95% or more similarity to these amino acid sequences; the 3 consensus sequences comprising the amino acid sequences shown in SEQ ID NOS: 1-3 from the N-terminal side in such order; and protein phosphatase 2C activity. Here, the value of similarity refers to a value that can be found based on default setting using a computer program mounted with a BLAST (Basic Local Alignment Search Tool) program and a database containing gene sequence information.

Also, genes analogous to protein phosphatase 2C genes comprising the nucleotide sequences and the amino acid sequences shown in SEQ ID NOS: 4-23 can be identified by, when the plant genome information remains unclarified, extracting the genome from a target plant or constructing a cDNA library for a target plant and then isolating a genomic region or cDNA hybridizing under stringent conditions to at least a portion of the protein phosphatase 2C genes comprising the nucleotide sequences and the amino acid sequences shown in SEQ ID NOS: 4-23. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

Examples of a technique for introducing such protein phosphatase 2C gene into a plant include a technique for introducing an expression vector in which an exogenous protein phosphatase 2C gene is arranged under control of a promoter that enables expression in a target plant. Examples of a technique for modifying an expression control region of an endogenous gene corresponding to the gene include a technique for modifying a promoter of an endogenous protein phosphatase 2C gene in a target plant.

A preferred example is a technique for introducing an expression vector in which the above protein phosphatase 2C gene is arranged under control of a promoter that enables expression in a target plant.

Glutathione-Binding Plastid-Type Fructose 1,6-bisphosphate Aldolase Gene

In the present invention, the glutathione-binding plastid-type fructose 1,6-bisphosphate aldolase gene is a gene which has activity that is controlled by its binding to glutathione and encodes an enzyme having activity of catalyzing a reaction (reversible reaction) for conversion of fructose 1,6-bisphosphate to dihydroxyacetone phosphate and glyceraldehyde-3-phosphate within a plastid such as chloroplast. The glutathione-binding plastid-type fructose 1,6-bisphosphate aldolase gene may be derived from any plant, as long as it encodes an enzyme having the above activity, or may also be a mutant gene resulting from introduction of mutation into a gene isolated from a plant.

As an example, *Arabidopsis thaliana*-derived glutathione-binding plastid-type fructose 1,6-bisphosphate aldolase gene can be used herein. The *Arabidopsis thaliana*-derived glutathione-binding plastid-type fructose 1,6-bisphosphate aldolase gene is disclosed as an FBA1 gene in WO2007/091634. The nucleotide sequence of the coding region in the FBA1 gene is shown in SEQ ID NO: 31, and the amino acid sequence of glutathione-binding plastid-type fructose 1,6-bisphosphate aldolase encoded by the FBA1 gene is shown in SEQ ID NO: 32. Also, the FBA1 gene in *Arabidopsis thaliana* is also referred to as an At2g01140 gene.

Also, in the present invention, a gene functionally equivalent to the above At2g01140 gene may be introduced into a plant or an expression control region of an endogenous gene corresponding to the gene may be modified. Here, the term "functionally equivalent gene" refers to a gene from an organism other than *Arabidopsis thaliana*, including a gene having glutathione-binding plastid-type fructose 1,6-bisphosphate aldolase activity, as an example. Also, fructose 1,6-bisphosphate aldolase activity can be measured by causing a protein to be measured for activity to act in a buffer containing fructose 1,6-bisphosphate as a substrate and then measuring the thus generated dihydroxyacetone phosphate and/or glyceraldehyde-3-phosphate. Alternatively, fructose 1,6-bisphosphate aldolase activity can also be measured as follows. Specifically, first, a protein to be measured for activity is caused to act in a buffer containing fructose 1,6-bisphosphate as a substrate. Triose phosphate isomerase is caused to act on the thus generated glyceraldehyde-3-phosphate, so that dihydroxyacetone phosphate is generated. When the dihydroxyacetone phosphate is altered to glycerol-3-phosphate in the presence of glycerol-3-phosphate dehydrogenase, NADH is converted to β-nicotinamide adenine dinucleotide (oxidized) (NAD). Hence, NADH-derived 340-nm absorbance decreases. Therefore, the protein to be measured for its aldolase activity can be evaluated by measuring the reduction rate of NADH.

Also, the glutathione binding property of a protein to be evaluated can be evaluated based on the presence or the absence of a glutathione binding sequence in the amino acid sequence of the protein or can also be evaluated by causing a protein to be evaluated to act in the presence of, glutathione transferase and glutathione and then measuring the presence or the absence of the binding of glutathione.

Moreover, whether a protein to be evaluated is of a plastid type can be evaluated based on the presence or the absence of a transit peptide sequence in the amino acid sequence of the protein, or can also be evaluated by producing a plant through introduction of a gene encoding a fusion protein of the protein and a reporter such as a fluorescent protein, detecting the reporter, and then detecting the localization of the plastid of the protein.

Here, examples of organisms other than *Arabidopsis thaliana* include, but are not limited to, rice (*Oryza sativa*). Specifically, an example of a functionally equivalent gene is a rice Os01g0118000 gene. The amino acid sequence of the protein encoded by the Os01g0118000 gene is shown in SEQ ID NO: 43.

Furthermore, examples of the above functionally equivalent genes from plants other than *Arabidopsis thaliana* and rice include a European grape (*Vitis vinifera*)-derived gene (NCBI Entrez Protein database Accession No. CAO42215 (SEQ ID NO: 40)), a castor-oil plant (*Ricinus communis*)-derived gene (NCBI Entrez Protein database Accession No. EEF36097 (SEQ ID NO: 39)), black cottonwood (*Populus trichocarpa*)-derived genes (NCBI Entrez Protein database Accession Nos. EEE88847 (SEQ ID NO: 38), EEF02079 (SEQ ID NO: 36) and ABK94899 (SEQ ID NO: 37)), Sitka Spruce (*Picea sitchensis*)-derived genes (NCBI Entrez Protein database Accession No. ABK24568 (SEQ ID NO: 35), ABK24286 (SEQ ID NO: 33), and ABK25226 (SEQ ID NO: 34)), and corn (*Zea mays*)-derived genes (NCBI Entrez Protein database Accession No. ACG47464 (SEQ ID NO: 41) and ACG47669 (SEQ ID NO: 42)).

In these plants other than *Arabidopsis thaliana*, which are represented by the above examples, a gene having glutathione-binding plastid-type fructose 1,6-bisphosphate aldolase activity can be easily searched for and/or identified from a known database such as GenBank based on the nucleotide sequence of above-listed *Arabidopsis thaliana*-derived FBA1 gene (At2g01140gene) or the amino acid sequence of the protein encoded by the gene.

FIG. 3 shows the results of alignment analysis using a CLUSTAL W (1.83) multiple sequence alignment program (which can be used with the DDBJ of the National Institute of Genetics (clustalw.ddbj.nig.ac.jp/top-j.html)) for the amino acid sequences shown in SEQ ID NOS: 32-43 (with the amino acid (sequence) substitution matrix used herein being a default matrix known as BLOSUM (Blocks of Amino Acid Substitution Matrix)). As shown in FIG. 3, glutathione-binding plastid-type fructose 1,6-bisphosphate aldolase genes exhibited very high homology. Also, FIG. 4 shows the result of creating a phylogenetic tree of the glutathione-binding plastid-type fructose 1,6-bisphosphate aldolase genes of the amino acid sequences shown in SEQ ID NOS: 32-43, *Arabidopsis thaliana* fructose 1,6-bisphosphate aldolase genes (FBA2 gene (At4g38970) and FBA3 gene (At2g21330)), and tobacco fructose 1,6-bisphosphate aldolase gene (BAA77604). As shown in the frame (broken line) in FIG. 4, the glutathione-binding plastid-type fructose 1,6-bisphosphate aldolase genes of the amino acid sequences shown in SEQ ID NOS: 32-43 form a group differing from those of the *Arabidopsis thaliana* FBA2 gene and FBA3 gene and the tobacco BAA77604 gene.

In addition, the fructose 1,6-bisphosphate aldolase proteins encoded by the *Arabidopsis thaliana* FBA2 gene and FBA3 gene do not have a characteristic of exhibiting fructose 1,6-bisphosphate aldolase activity due to glutathione.

In the present invention, examples of a glutathione-binding plastid-type fructose 1,6-bisphosphate aldolase gene are not limited to the above gene encoding the nucleotide sequence shown in SEQ ID NO: 31 and genes encoding proteins comprising the amino acid sequences shown in SEQ ID NOS: 32-43. Specifically, examples of the glutathione-binding plastid-type fructose 1,6-bisphosphate aldolase genes comprise amino acid sequences that have a deletion(s), a substitution(s), an addition(s), or an insertion(s) of one or a plurality of amino acid sequences with respect to the amino acid sequences shown in SEQ ID NOS: 32-43, and, have glutathione-binding plastid-type fructose 1,6-bisphosphate aldolase activity. Here, the term "a plurality of amino acids" refers to 1 to 20 amino acids, preferably 1 to 10 amino acids, more preferably 1 to 7 amino acids, further preferably 1 to 5 amino acids, and particularly preferably 1 to 3 amino acids. In addition, for deletion, substitution, or addition of an amino acid(s), techniques disclosed in the above column, "Protein phosphatase 2C gene" can be applied.

Also, the glutathione-binding plastid-type fructose 1,6-bisphosphate aldolase genes may be homologous to genes encoding the nucleotide sequence shown in SEQ ID NO: 31 and the proteins comprising the amino acid sequences shown in SEQ ID NOS: 32-43. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes analogous to the gene encoding the nucleotide sequence shown in SEQ ID NO: 31 and the genes encoding the proteins comprising the amino acid sequences shown in SEQ ID NOS: 32-43 include genes encoding proteins that have amino acid sequences having 70% or more, preferably 80% or more, more preferably 90% or more, and most preferably 95% or more similarity with respect to the amino acid sequences of SEQ ID NOS: 32-43 and have glutathione-binding plastid-type fructose 1,6-bisphosphate aldolase activity. Here, the values for similarity are obtained through application of techniques disclosed in the above column "Protein phosphatase 2C gene".

Also, genes analogous to a gene containing the nucleotide sequence shown in SEQ ID NO: 31 and the genes encoding the proteins comprising the amino acid sequences shown in SEQ ID NOS: 32-43 can be identified by, when the plant genome information remains unclarified, extracting the genome from a target plant or constructing a cDNA library for a target plant and then isolating a genomic region or cDNA hybridizing under stringent conditions to at least a portion of a gene containing the nucleotide sequence shown in SEQ ID NO: 31 and the genes encoding the proteins comprising the amino acid sequences shown in SEQ ID NOS: 32-43. Here, the term "stringent conditions" refers to conditions as disclosed in the above column "Protein phosphatase 2C gene". Techniques as disclosed in the above column "Protein phosphatase 2C gene" can be applied to hybridization.

As a technique for introducing the glutathione-binding plastid-type fructose 1,6-bisphosphate aldolase gene into a plant or modifying an expression control region of an endogenous gene corresponding to the gene, techniques disclosed in the above column "Protein phosphatase 2C gene" are applicable.

Expression Vector

An expression vector is constructed to contain a promoter that enables expression within plants and the above described protein phosphatase 2C gene and glutathione-binding plastid-type fructose 1,6-bisphosphate aldolase gene. In addition, an expression vector containing the protein phosphatase 2C gene and an expression vector containing the glutathione-binding plastid-type fructose 1,6-bisphosphate aldolase gene may be separately prepared.

As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of a protein phosphatase 2C gene and a glutathione-binding plastid-type fructose 1,6-bisphosphate aldolase gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase.oxidase small subunit gene promoter, and a napin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can also be used herein. As such promoter, any conventionally known promoter can be used. When the above described protein phosphatase 2C gene or glutathione-binding plastid-type fructose 1,6-bisphosphate aldolase gene is site-specifically expressed using such promoter, a plant organ in which the gene is expressed can be more increased than wild-type plant organs.

In addition, an expression vector may further contain other DNA segments in addition to a promoter, the above protein phosphatase 2C gene and the above glutathione-binding plastid-type fructose 1,6-bisphosphate aldolase gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a transcript after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector can contain various DNA segments depending on purposes.

A method for constructing a recombinant expression vector is not particularly limited. To an appropriately selected vector serving as a mother body, the above promoter, the above protein phosphatase 2C gene and/or the above glutathione-binding plastid-type fructose 1,6-bisphosphate aldolase gene, a transcription repressor converting polynucleotide, and if necessary, the above other DNA segments may be introduced in an predetermined order. For example, the above protein phosphatase 2C gene or the above glutathione-binding plastid-type fructose 1,6-bisphosphate aldolase gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the above protein phosphatase 2C gene or the above glutathione-binding plastid-type fructose 1,6-bisphosphate aldolase gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G. (1993) In Planta *Agrobacterium*-mediated gene transfer by infiltration of adult *Arabidopsis* plants. C.R. Acad. Sci. Paris Sci. Vie, 316, 1194-1199., or a method described in Zyprian E, Kado Cl, *Agrobacterium*-mediated plant transformation by novel mini-T vectors in conjunction with a high-copy vir region helper plasmid. Plant Molecular Biology, 1990, 15(2), 245-256. can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

Plants into which an expression vector is introduced or in other words, plants required to increase the production of biomass are not particularly limited. Specifically, through introduction of the above-described protein phosphatase 2C gene and the above glutathione-binding plastid-type fructose 1,6-bisphosphate aldolase gene, effects of increasing the production of biomass can be expected for all plants. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana* (*Arabidopsis thaliana*), rapeseed (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), komatsuna (*Brassica rapa* var. *peruviridis*), pak choi (*Brassica rapa* var. *chinensis*), daikon (*Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus*

*virgatum*), sorghum (*Sorghum*) and switch grass (*Panicum*), and the like

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. This is because the costs for biofuel such as bioethanol, biodiesel, biomethanol, bioDME, bioGTL (BTL), and biobutanol can be reduced by increasing the production of biomass using energy crops.

Also, as described above, protein phosphatase 2C genes that can be used in the present invention and the above glutathione-binding plastid-type fructose 1,6-bisphosphate aldolase gene can be isolated from various plants and used. Such protein phosphatase 2C genes and glutathione-binding plastid-type fructose 1,6-bisphosphate aldolase gene can be appropriately selected and used, depending on the types of target plant required to increase the biomass production.

Specifically, when a plant required to increase the biomass production is a monocotyledon, a protein phosphatase 2C gene that is isolated from a monocotyledon is preferably introduced. In particular, when a plant required to increase the biomass production is rice, the rice-derived protein phosphatase 2C gene (SEQ ID NO: 6) is preferably introduced. The above glutathione-binding plastid-type fructose 1,6-bisphosphate aldolase gene can be similarly selected depending on plants required to increase the biomass production.

In addition, in the present invention, even when a plant required to increase the biomass production is a monocotyledon, a dicotyledon-derived protein phosphatase 2C gene or glutathione-binding plastid-type fructose 1,6-bisphosphate aldolase gene may be introduced. Specifically, for example, the *Arabidopsis thaliana*-derived protein phosphatase 2C gene (SEQ ID NO: 4) and the glutathione-binding plastid-type fructose 1,6-bisphosphate aldolase gene (SEQ ID NO: 31) may be introduced into not only dicotyledons, but also a variety of plants that are classified as monocotyledons, so that the genes are expressed.

Meanwhile, when an expression vector containing a protein phosphatase 2C gene and an expression vector containing a glutathione-binding plastid-type fructose 1,6-bisphosphate aldolase gene are separately prepared, transformation may be performed using both expression vectors, or a transformed plant may be obtained by transformation using one of the expression vectors, following which such transformed plant may be further transformed with the other expression vector. For example, a transformed plant is obtained using one of the expression vectors, self-fertilized seeds of the transformed plant are harvested, the fixation of the introduced genes in the progeny plants is confirmed, and thus the progeny plants can be transformed with the other expression vector.

Also, a transformed plant introducing a protein phosphatase 2C gene and a transformed plant introducing a glutathione-binding plastid-type fructose 1,6-bisphosphate aldolase gene may be produced separately The thus separately produced transformed plants are crossed, and thus progeny plants having both the protein phosphatase 2C gene and the glutathione-binding plastid-type fructose 1,6-bisphosphate aldolase gene can be obtained.

Furthermore, through induction of mutation, introduction of a gene activating factor, and the like, plants in which the expression of the plants' own protein phosphatase 2C gene and glutathione-binding plastid-type fructose 1,6-bisphosphate aldolase gene is activated may be selected.

Other Steps and Methods

After the above transformation, a step of screening for proper transformants from plants can be performed by a conventionally known method. Such screening method is not particularly limited. For example, selection can be made based on drug resistance such as hygromycin resistance. Alternatively, after the growth of transformants, a transformant with a significant increase in biomass production compared with a wild type plant may be screened for by determining the weight of a plant itself or its arbitrary organ or tissue.

Also, progeny plants can be obtained from transformed plants obtained by transformation according to a conventional method. Progeny plants retaining a trait resulting from the introduction of the above protein phosphatase 2C gene and the above glutathione-binding plastid-type fructose 1,6-bisphosphate aldolase gene or a trait resulting from the modification of an expression control region of endogenous genes corresponding to the genes are selected based on their amounts of biomass. Therefore, because of having the above trait, a stable plant line exhibiting the increased production of biomass can be produced. Also, plant cells or reproductive materials, such as seeds, fruits, stocks, calluses, tubers, cut ears, or lumps, may be obtained from such a transformed plant or progeny plants thereof. Because of having the above trait, a stable plant line exhibiting the increased production of biomass can be mass-produced from such cells or materials.

In addition, the plant of the present invention may include a matter comprising at least any one of adult plants, plant cells, plant tissues, calli, and seeds. That is, according to the present invention, any matter in a state that allows it to eventually grow to become a plant can be regarded as a plant. In addition, the above plant cells include plant cells in various forms. Examples of such plant cells include suspension-cultured cells, protoplasts, and leaf sections. As a result of proliferation/differentiation of such plant cells, a plant can be obtained. In addition, a plant can be reproduced from plant cells by a conventionally known method depending on the types of plant cells.

As explained above, according to the present invention, plants capable of exhibiting the significantly increased production of biomass and/or seeds per plant compared with a wild-type plant can be provided by introducing the above protein phosphatase 2C gene and the above glutathione-binding plastid-type fructose 1,6-bisphosphate aldolase gene thereinto or modifying an expression control region of endogenous genes corresponding to the genes. Here, the term "significantly increased production of biomass" refers to a situation in which the total weight of each plant is statistically significantly increased compared with the same of a wild-type plant. In this case, even when some plant tissues become specifically large and the sizes of the other tissues are equivalent to those of a wild-type plant, it is concluded that the production of biomass is increased if the total weight of the entire plant is large. In addition, the term "significantly increased production of seeds" refers to a situation in which the total amount and/or total number of seeds harvested from each plant is statistically significantly increased compared with the same of a wild-type plant. Specifically, such a situation may be any of a situation in which the size of each seed (grain) is improved, a situation in which the size of each seed (grain) is equivalent to the other but the number of seeds is improved, or a situation in which the size of each seed (grain) is improved and the number of seeds is improved.

According to the present invention, the production of biomass and/or seeds by plants is increased. Hence, improvement in productivity can be achieved in both of the following cases: a case in which a purpose is to produce the whole plant; and a case in which a purpose is to produce some plant tissues (e.g., seeds) or components contained in plants. For example, when a purpose is to produce fats and oils contained in plant seeds, the amounts of fats and oils that can be harvested per area under cultivation can be greatly improved. Here, examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the thus produced fats and oils can be broadly used for household uses or industrial uses and can be further used as raw materials for biodiesel fuel. Hence, according to the present invention, the above fats and oils for household uses or industrial uses, biodiesel fuel, and the like can be produced at low cost with the use of plants into which the above protein phosphatase 2C gene and the above glutathione-binding plastid-type fructose 1,6-bisphosphate aldolase gene have been introduced or in which an expression control region of endogenous genes corresponding to the genes has been modified.

It is industrially very important to further enhance a useful trait through a combination of a plurality of techniques for modifying a gene exhibiting the useful trait via activation of gene expression. However, it cannot be said that the determination of gene modification techniques to be combined in such a way is always easy. When many genes are subjected to technical development, many combinations may need to be evaluated. The protein phosphatase 2C genes that are used in the present invention are assumed to be involved in signal transduction with which plant hormones and particularly gibberellic acid and abscisic acid are associated. Hence, we attempted to use a glutathione-binding plastid-type fructose 1,6-bisphosphate aldolase gene that is associated with photosynthesis in one combination and thought to have a weak association with the above signal transduction. This combination resulted in additive effects in increased production of biomass and/or seeds of a plant into which both genes had been introduced or in which an expression control region of the endogenous genes corresponding to the genes had been modified. These results indicate that additive effects can be expected when a gene associated with signal transduction (with which gibberellic acid or abscisic acid is associated) and a gene for which a change in the above signal transduction does not serve as a major factor for increased production of biomass and/or seeds are used in combination, as in the case of a protein phosphatase 2C gene. Examples of such a gene include AINTEGUMENTA (Proc. Natl. Acad. Sci. U.S.A., 97 942-947, (2000)), ARGOS (Plant Cell, 15, 1951-1961, (2003)), ARL (Plant J., 47, 1-9, (2006)), AVP1 (Science, 310, 121-125, (2005)), and ARF2 (Development, 133, 251-261, (2006)).

EXAMPLES

The present invention will be specifically described in the following reference examples and examples. However, the examples are not intended to limit the technical scope of the present invention.

Reference Example 1

1. Materials and Methods
1-1. Experimental Materials
As experimental materials, seeds of *Arabidopsis thaliana* mutants (Activation-tag lines: Weigel T-DNA lines, 20072 lines) were used. In addition, the seeds were purchased from the Nottingham *Arabidopsis* Stock Centre (NASC). Regarding the seeds used as experimental materials, Weigel, D. et al., 2000, Plant Physiol. 122, 1003-1013 can be referred to.

1-2. Methods
1-2-1. Selection of Salt-Resistant Mutants
Seeds of Weigel T-DNA lines were aseptically sowed on 125 mM or 150 mM NaCl-containing modified MS agar (1%) medium [vitamins in B5 medium, 10 g/l sucrose, and 8 g/L agar (for bacterial medium; Wako Pure Chemical Industries, Ltd.)] and then cultured at 22° C. under 30-100 µmol/m$^2$/sec illumination (a cycle of 16 hours in the light/8 hours in the dark). Two to 4 weeks after sowing, salt-resistant mutant candidates were selected. In addition, regarding MS medium, see Murashige, T. et al., 1962, Physiol. Plant. 15, 473-497. Also, regarding the B5 medium, see Gamborg, O. L. et al., 1968, Experimental Cell Research 50, 151-158.

1-2-2. DNA Preparation
A site for insertion of T-DNA into the genome of the thus selected salt-resistant *Arabidopsis thaliana* line was determined by a TAIL-PCR method. First, young leaves were harvested from the cultivated *Arabidopsis thaliana* plants and then crushed under liquid nitrogen freezing. DNA was prepared using a DNA preparation kit (DNeasy Plant Mini Kit, QIAGEN) according to the standard protocols included with the kit.

1-2-3. TAIL-PCR Method and Presumption of T-DNA Insertion Site
Three (3) types of specific primer, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR reaction solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Liu, Y. G. and Whttier, R. F., 1995, Genomics 25, 674-681; Liu, Y. G. et al., Plant J., 8, 457-463, 1995) was performed, so that genomic DNA adjacent to T-DNA was amplified.

The specific sequences of the primers TL1, TL2, TL3, and P1 are as follows.

```
                                          (SEQ ID NO: 24)
TL1:    5'-TGC TTT CGC CAT TAA ATA GCG ACG G-3'

(SEQ ID NO: 25)
TL2:    5'-CGC TGC GGA CAT CTA CAT TTT TG-3'

(SEQ ID NO: 26)
TL3:    5'-TCC CGG ACA TGA AGC CAT TTA C-3'

(SEQ ID NO: 27)
P1:     5'-NGT CGA SWG ANA WGA A-3'
```

In addition, in SEQ ID NO: 25, "n" represents "a," "g," "c," or "t" (location: 1 and 11), "s" represents "g" or "c" (location: 7), and "w" represents "a" or "t" (location: 8 and 13).

The 1st PCR reaction solution composition and reaction conditions are shown in Table 1 and Table 2, respectively.

TABLE 1

| Template (genomic DNA) | 10 ng |
|---|---|
| 10xPCR buffer (Takara Bio) | 2 µl |
| 2.5 mM dNTPs (Takara Bio) | 1.6 µl |

TABLE 1-continued

| | |
|---|---|
| 1st specific primer (TL1: SEQ ID NO: 24) | 0.5 pmol |
| Arbitrary primer 1 (SEQ ID NO: 27) | 100 pmol |
| TaKaRa Ex Taq (Takara Bio) | 1.0 unit |
| Total | 20 µl |

TABLE 2

| | |
|---|---|
| #1: | 94° C. (30 seconds)/95° C. (30 seconds) |
| #2: | 5 cycles of 94° C. (30 seconds)/65° C. (30 seconds)/72° C. (1 minute) |
| #3: | 1 cycle of 94° C. (30 seconds)/25° C. (1 minute) raised to 72° C. within 3 minutes/72° C. (3 minutes) |
| #4: | 94° C. (15 seconds)/65° C. (30 seconds)/72° C. (1 minute) 94° C. (15 seconds)/68° C. (30 seconds)/72° C. (1 minute) 15 cycles of 94° C. (15 seconds)/44° C. (30 seconds)/72° C. (1 minute) |
| #5: | 72° C. (3 minutes) |

The 2nd PCR reaction solution composition and reaction conditions are shown in Table 3 and Table 4, respectively.

TABLE 3

| | |
|---|---|
| Template (50-fold dilution of the 1st PCR product) | 1 µl |
| 10xPCR buffer (Takara Bio) | 2 µl |
| 2.5 mM dNTPs (Takara Bio) | 1.5 µl |
| 2nd specific primer (TL2: SEQ ID NO: 25) | 5 pmol |
| Arbitrary primer 1 (SEQ ID NO: 27) | 100 pmol |
| TaKaRa Ex Taq (Takara Bio) | 0.8 unit |
| Total | 20 µl |

TABLE 4

| | |
|---|---|
| #6: | 94° C. (15 seconds)/64° C. (30 seconds)/72° C. (1 minute) 94° C. (15 seconds)/64° C. (30 seconds)/72° C. (1 minute) 12 cycles of 94° C. (15 seconds)/44° C. (30 seconds)/72° C. (1 minute) |
| #5: | 72° C. (5 minutes) |

The 3rd PCR reaction solution composition and reaction conditions are shown in Table 5 and Table 6, respectively.

TABLE 5

| | |
|---|---|
| Template (50-fold dilution of the 2nd PCR product) | 1 µl |
| 10xPCR buffer (Takara Bio) | 5 µl |
| 2.5 mM dNTPs (Takara Bio) | 0.5 µl |
| 3rd specific primer (TL3: SEQ ID NO: 26) | 10 pmol |
| Arbitrary primer 1 (SEQ ID NO: 27) | 100 pmol |
| TaKaRa Ex Taq (Takara Bio) | 1.5 unit |
| Total | 50 µl |

TABLE 6

| | |
|---|---|
| #7: | 20 cycles of 94° C. (30 seconds)/44° C. (30 seconds)/72° C. (1 minute) |
| #5: | 72° C. (3 minutes) |

Subsequently, the 2nd and the 3rd reaction products were subjected to agarose gel electrophoresis and then the presence or the absence of amplification and the specificity of reaction products were confirmed. Also, the 3rd amplification products were subjected to a sequencing reaction directly using a BigDye Terminator Cycle Sequencing Kit Ver. 3. 1 (Applied Biosystems) and the specific primer TL3.

Thus, a nucleotide sequence was determined using an ABI PRISM 3100 Genetic Analyzer (Applied Biosystems). As a result, 498-bp sequence information was obtained (SEQ ID NO: 28).

The Arabidopsis Information Resource (TAIR:arabidopsis.org/) was subjected to a BLAST search for the thus obtained sequence. Thus, the insertion site was found to be the gene of [AGI (Arabidopsis Genome Initiative gene code) code: At3g05630] of *Arabidopsis thaliana* chromosome 3.

1-2-4. Prediction of Activated Genes

Activated genes were predicted from the sequence of a presumed open reading frame (ORF) gene existing within a 10-Kb range near the T-DNA insertion site (At3g05630) revealed in 1-2-3.

1-2-5. Obtainment of Predicted Genes

For amplification of a fragment containing the ORF region of PP2C (protein phosphatase 2C) gene (At3g05640) predicted to be activated in 1-2-4, PCR primers 5640PF1 and 5640PR1 were designed and synthesized based on the sequence information disclosed at the TAIR (<arabidopsis.org/home.html>). In addition, these primers were designed, so that a restriction enzyme site (BsrG I or Sal I) required for introduction into expression vectors was added to the terminus of each primer.

```
5640PF1(SEQ ID NO: 29):
5'-ACG CGT CGA CAT GGG ACA TTT CTC TTC CAT GTT
CAA CGG-3'

5640PR1(SEQ ID NO: 30):
5'-TGT ACA TGT ACA CTA TAG AGA TGG CGA CGA CGA
TGA AGA ATG G-3'
```

According to the method described in 1-2-2, a template DNA was prepared from wild-type *Arabidopsis thaliana* (ecotype Col-0). Phusion High-Fidelity DNA Polymerase (New England BioLabs: NEB) was used as an enzyme and the above 5640 PF1 and 5640PR1 were used as primers. The relevant PCR reaction solution composition and reaction conditions are shown in Table 7 and Table 8, respectively.

TABLE 7

| | |
|---|---|
| Template (genomic DNA) | 60 ng |
| 10xHF buffer (NEB) | 5 µl |
| 10 mM dNTPs (NEB) | 1.0 µl |
| Each primer | 20 pmol |
| Phusion High-Fidelity DNA Polymerase | 1.0 unit |
| Total | 50 µl |

TABLE 8

| | |
|---|---|
| #1: | 98° C. (30 seconds) |
| #2: | 15 cycles of 98° C. (10 seconds)/55° C. (30 seconds)/72° C. (30 seconds) |
| #5: | 72° C. (10 minutes) |

PCR amplification products were subjected to electrophoresis with 2% agarose gel (TAE buffer) and then fragments were stained with ethidium bromide. A gel containing target fragments was excised using a scalpel. Target DNA fragments were eluted and purified using GFX PCR DNA and a GEL Band Purification Kit (Amersham). Adenin was added to the thus obtained DNA fragment using an A-Addition Kit (QIAGEN). The amplified DNA to which adenine had been added was ligated to a TA-Cloning pCR2.1 vector using a TOPO TA Cloning Kit (Invitrogen) and then transformed into competent cells (*E. coli* TOP 10) included with the kit. After transformation, cells were cultured in LB medium supplemented with 50 µl/ml kanamycin and then transformants were selected. Colonies that had appeared were subjected to liquid culture in LB medium supplemented with 50 µl/ml kanamycin. Plasmid DNA was prepared from the thus obtained microorganisms using a Plasmid Mini Kit (QIAGEN). The thus obtained fragment containing ORF of the PP2C (protein phosphatase 2C) gene (At3g05640) was cloned into a vector, followed by determination of the nucleotide sequence and sequence analysis.

1-2-6. Construction of Plant Expression Vector

A fragment containing ORF of the PP2C (protein phosphatase 2C) gene (At3g05640) was inserted into a plant expression vector pBI121 containing an omega sequence from tobacco mosaic virus. Thus, a construct was prepared.

First, the pCR2.1 vector, in which a fragment containing ORF of the PP2C (protein phosphatase 2C) gene (At3g05640) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 2700 by containing ORF of the PP2C (protein phosphatase 2C) gene (At3g05640) and pBI121 containing the omega sequence were each fractioned and purified from the gel using GFX PCR DNA and a GEL Band Purification Kit (Amersham).

For introduction of a fragment containing ORF of the PP2C (protein phosphatase 2C) gene (At3g05640) using a pBI121 fragment containing the omega sequence as a vector, the vector and the insert were mixed at a ratio of 1:10, followed by an overnight ligation reaction at 16° C. using an equivalent amount of a TaKaRa Ligation kit ver. 2 (Takara Bio Inc.).

The total amount of the reaction solution was added to 100 µl of competent cells (*E. coli* strain DH5α, TOYOBO), so that transformation was performed according to protocols included with the kit. Cells were applied to LB agar medium containing 50 µg/ml kanamycin and then cultured overnight. Colonies that had appeared were subjected to liquid culture in LB medium supplemented with 50 µg/ml kanamycin. Plasmid DNA was prepared from the thus obtained microorganisms using a Plasmid Mini Kit (QIAGEN).

The thus obtained fragment containing ORF of the PP2C (protein phosphatase 2C) gene (At3g05640) was subcloned into an expression vector, followed by determination of the nucleotide sequence and sequence analysis.

1-2-7. Gene Introduction into *Arabidopsis thaliana* Using *Agrobacterium* Method The plant expression vector constructed in 1-2-6 was introduced into *Agrobacterium tumefaciens* C58C1 strain by electroporation (Plant Molecular Biology Mannal, Second Edition, B. G. Stanton and A. S. Robbert, Kluwer Acdemic Publishers 1994). Subsequently, *Agrobacterium tumefaciens* in which the plant expression vector had been introduced was introduced into wild-type *Arabidopsis thaliana* (ecotype Col-0) by an infiltration method described by Clough et al. (Steven J. Clough and Andrew F. Bent, 1998, The Plant Journal 16, 735-743).

Transformants were selected using kanamycin-containing medium. T1 generation plants were produced by self-pollination from the transformants, so that T2 seeds were obtained.

1-2-8. Confirmation of the Phenotype of Transformant

T2 seeds produced in 1-2-7 were aseptically sowed and then the resulting plants were transplanted into pots (each with a diameter of 50 mm) containing vermiculite mixed soil. As control plants for comparison, *Arabidopsis* plants that had not undergone recombination were transplanted. They were cultivated under conditions of 22° C. and 16 hours in the light/8 hours in the dark, and with a light intensity ranging from about 30 to 45 $\mu mol/m^{-2}/s^{-1}$, for a total of 11 weeks after transplantation. After cultivation, above-ground parts of the plants were placed in paper bags and dried under conditions of 22° C. and humidity of 60% for 2 weeks. The total amounts of biomass and seeds were weighed using an electronic balance.

1-3. Results

Figure 5:
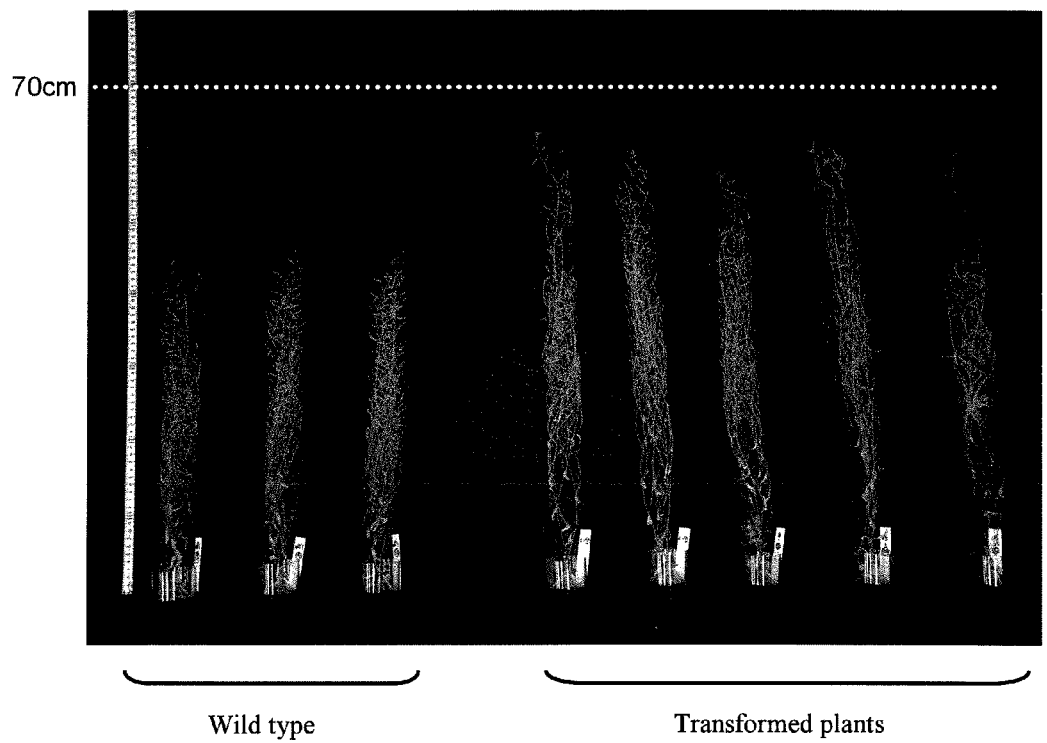
FIG. 5 is a photo showing the above-ground parts of wild-type plants and transformed plants into which a fragment containing ORF of PP2C (protein phosphatase 2C) gene (At3g05640) was introduced.

Regarding the results of 1-2-8, FIG. 5 shows a photo of the above-ground parts of wild-type plants and transformed plants into which a fragment containing ORF of the PP2C (protein phosphatase 2C) gene (At3g05640) had been introduced. Also, FIG. 6 and FIG. 7 show the results of measuring the total amounts of biomass and seeds of the above-ground parts of the plants.

Figure 6:
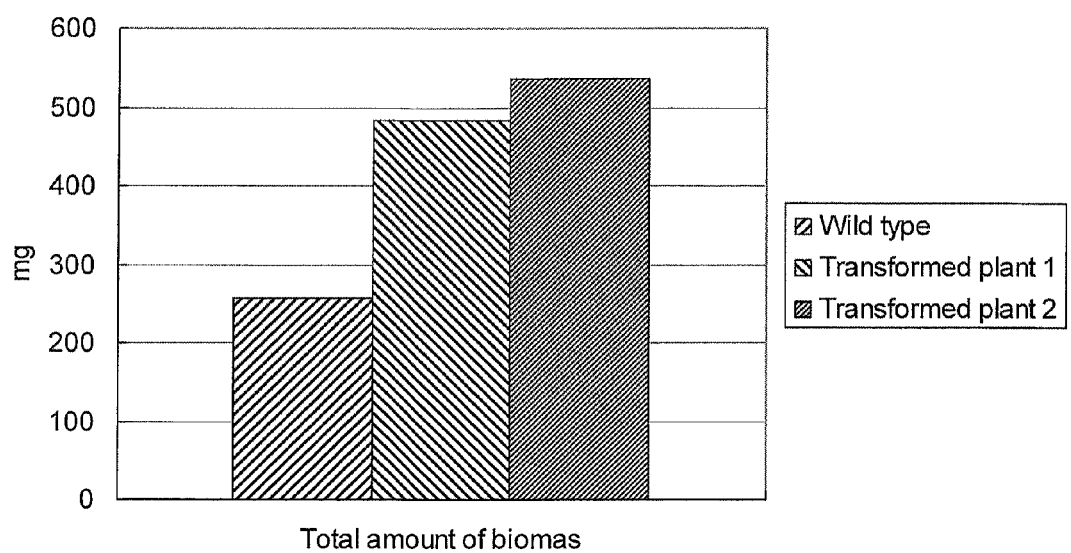
FIG. 6 is a characteristic diagram showing the results of measuring the amounts of biomass of the above-ground parts of wild-type plants and transformed plants into which a fragment containing ORF of the PP2C (protein phosphatase 2C) gene (At3g05640) was introduced. The result for the wild-type plants is the average value for 12 individual wild-type plants and each result for the transformed plants is the average value for 5 individual transformed plants.
Figure 7:
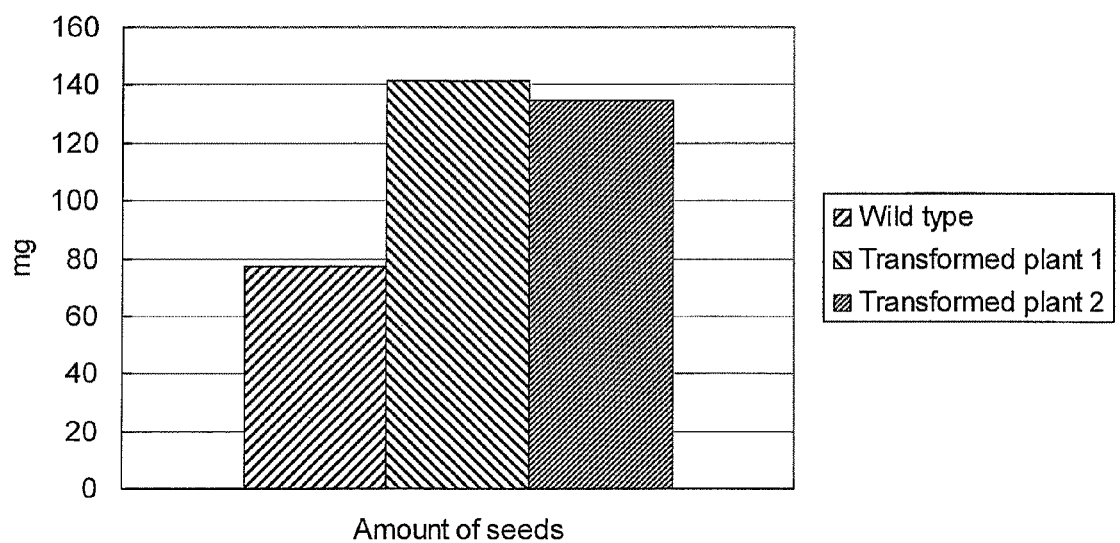
FIG. 7 is a characteristic diagram showing the results of measuring the amounts of seeds of wild-type plants and transformed plants into which a fragment containing ORF of the PP2C (protein phosphatase 2C) gene (At3g05640) was introduced. The result for the wild-type plants is the average value for 12 individual wild-type plants and each result for the transformed plants is the average value for 5 individual transformed plants.

As shown in FIGS. 5, 6, and 7, it was revealed that in the case of transformed plants into which the fragment containing ORF of the PP2C (protein phosphatase 2C) gene (At3g05640) had been introduced, the total amounts of biomass of the above-ground parts were much higher (about 1.9 to 2.1 times) than the amounts of the same in the cases of wild-type plants. In addition, the amounts of seeds were much greater (by about 1.7 to 1.8 times) than the same in the cases of wild-type plants.

Example 1

In Example 1, transformed plants were produced by introducing a glutathione-binding plastid-type fructose 1,6-bisphosphate aldolase gene (hereinafter, FBA1 gene) into transformed plants into which the PP2C (protein phosphatase 2C) gene (At3g05640) had been introduced.

2. Materials and Methods 2-1. Experimental Materials

As experimental materials, the seeds of T3 (or later) plants of transformed plants into which a fragment containing ORF of the PP2C (protein phosphatase 2C) gene (At3g05640) prepared in 1-2-7 had been introduced, were used. Wild-type *Arabidopsis thaliana* (ecotype Col-0) was used.

The plants were transplanted into square plastic pots (6.5×6.5×5 cm) containing, from the bottom, vermiculite (Asahi Kogyo), Kureha culture soil (Kureha gardening culture soil, Kureha Corporation), and vermiculite at a ratio of 2:2:1 to form 3 layers. They were grown under long-day conditions of 22° C. (growth temperature) and 16 hours in the light/8 hours in the dark.

2-2. Methods 2-2-1. Obtainment of FBA1 Gene (At2g01140)

Total RNA was isolated from 4-week-old *Arabidopsis thaliana* (wild-type Columbia (Col-0)), RT-PCR (amount of template RNA; 5.0 µg) was performed using a Prost arfirst-strand RT-PCR kit (Stratagene), and thus cDNA was constructed.

PCR was performed using the following specific primers that had been designed based on the cDNA sequence (SEQ ID NO: 31) of the FBA1 gene (At2g01140), so as to amplify the full-length cDNA as two fragments. The thus amplified fragments were each TA-cloned into a pGEM-T vector (Promega).

| | | (SEQ ID NO: 44) |
|---|---|---|
| 1F-1: | 5'-GGATCCTATGGCGTCTGCTAG-3' | |
| | | (SEQ ID NO: 45) |
| 1R-1: | 5'-ATCTGCAACGGTCTCGGGAGA-3' | |
| | | (SEQ ID NO: 46) |
| 1F-2: | 5'-GTGTGGTCCGAGGTGTTCTTCT-3' | |
| | | (SEQ ID NO: 47) |
| 1R-2: | 5'-GAGCTCGAGTAGGTGTAACCCTTG-3' | |

Two fragments were fused at the Bstp I site, and thus a vector (pGEM-FBA1) containing the full-length cDNA was constructed. For production of transformed plants, pGEM-FBA1 was treated with restriction enzymes BamH I and Sac I and then the resulting fragment was introduced into a pBI121 vector.

2-2-2. Construction of Plant Expression Vector

The fragment containing the FBA1 gene (At2g01140) obtained in 2-2-1 was inserted into a pMAT137-HM plant expression vector (Matsuoka K. and Nakamura K., 1991, Proc. Natl. Acad. Sci. U.S.A. 88, 834-838), so that a construct was prepared.

First, the fragment containing the FBA1 gene and a NOS terminator incorporated into the pBI121 vector was excised with Xba I and EcoR I and then incorporated into a pBluscriptII (SK+) vector (Stratagene) that had been treated with Xba I and EcoR I. Subsequently, the fragment containing the FBA1 gene and the NOS terminator was excised with Xba I and Kpn I and then incorporated into a pMAT137-Hm vector that had been treated with Xba I and Kpn I.

2-2-3. Gene Introduction into *Arabidopsis thaliana* Using *Agrobacterium* Method The pMAT137-Hm plant expression vector constructed in 2-2-2 was introduced into the *Agrobacterium tumefaciens* C58C1 strain by electroporation (Plant Molecular Biology Mannal, Second Edition, B. G. Stanton and A. S. Robbert, Kluwer Academic Publishers 1994). Subsequently, *Agrobacterium tumefaciens* into which the plant expression vector had been introduced was introduced into wild-type *Arabidopsis thaliana* (ecotype Col-0) by an infiltration method described by Clough et al. (Steven J. Clough and Andrew F. Bent, 1998, The Plant Journal 16, 735-743).

Transformants were selected using hygromycin-containing medium. T1 generation plants were produced by self-pollination from the transformants, so that T2 seeds were obtained.

2-2-4. Confirmation of the Phenotype of Transformant

T2 seeds produced in 2-2-3 were sowed into square plastic pots (6.5×6.5×5 cm) containing, from the bottom, vermiculite (Asahi Kogyo), Kureha culture soil (Kureha gardening culture soil, Kureha Corporation), and vermiculite at a ratio of 2:2:1 to form 3 layers. They were grown under long-day conditions of 22° C. (growth temperature) and 16 hours in the light/8 hours in the dark. As control plants, transformed plants produced with the introduction of the PP2C gene prepared in Reference example 1 (1-2-7) were used. They were cultivated under conditions of 22° C., 16 hours in the light/8 hours in the dark, and a light intensity ranging from about 70 to 100 µmol/m$^{-2}$/s$^{-1}$, for a total of 11 weeks after transplantation. After cultivation, above-ground parts of the plants were placed in paper bags and dried under conditions of 22° C. and humidity of 60% for 2 weeks. The total amounts of biomass were weighed using an electronic balance.

2-3. Results

Figure 8:
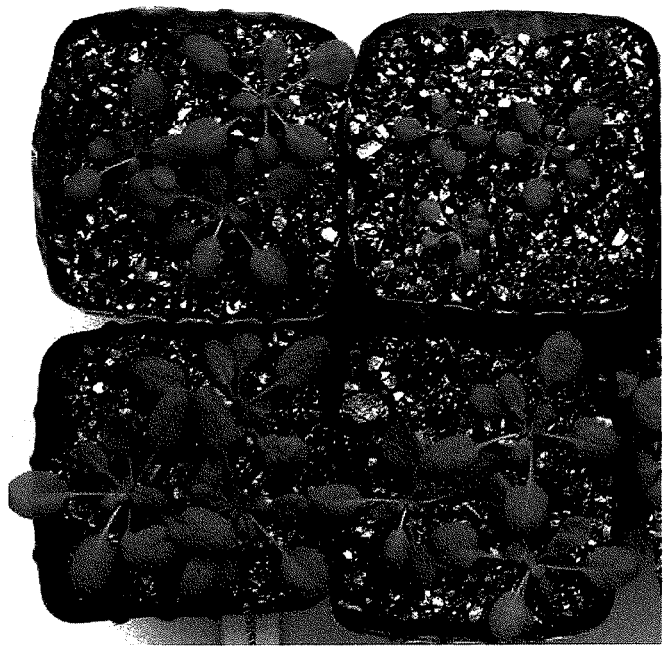
FIG. 8 is a photo showing the above-ground parts of wild-type plants, transformed plants produced by introducing a fragment containing ORF of the PP2C (protein phosphatase 2C) gene (At3g05640), and transformed plants produced by introducing an FBA1 gene (At2g01140) into the above-mentioned transformed plants (into which a fragment containing ORF of the PP2C (protein phosphatase 2C) gene (At3g05640) had been introduced).
Figure 9:
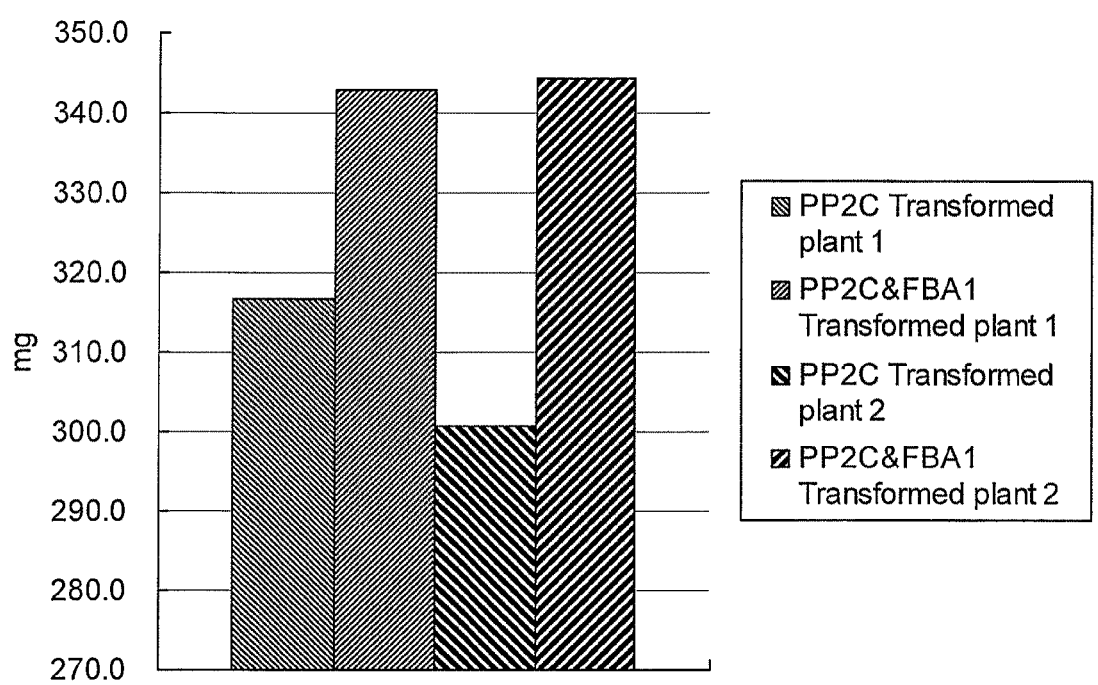
FIG. 9 is a characteristic diagram showing the results of measuring the amounts of biomass of the above-ground parts of transformed plants produced by introducing a fragment containing ORF of the PP2C (protein phosphatase 2C) gene (At3g05640), as well as transformed plants produced by introducing an FBA1 gene (At2g01140) into the aforementioned transformed plants (into which a fragment containing ORF of the PP2C (protein phosphatase 2C) gene (At3g05640) had been introduced).

FIG. 8 is a photo showing the results of 2-2-4 above and specifically the above-ground parts of wild-type plants, transformed plants produced with the introduction of a fragment containing ORF of the PP2C (protein phosphatase 2C) gene (At3g05640), and transformed plants produced by introducing the FBA1 gene (At2g01140) into the above-mentioned transformed plants (into which a fragment containing ORF of the PP2C (protein phosphatase 2C) gene (At3g05640) had been introduced). FIG. 9 shows the results of measuring the total amounts of biomass of the above-ground parts. In addition, each amount of biomass shown in FIG. 9 is the average value for 6 pots each containing 3 individual plants.

As revealed in FIG. 8, in the case of transformed plants produced with the introduction of the FBA1 gene (At2g01140) into transformed plants that had been produced with the introduction of the fragment containing ORF of the PP2C (protein phosphatase 2C) gene (At3g05640), the sizes of above-ground parts had improved over those of wild-type plants and the transformed plants produced with the introduction of the fragment containing ORF of the PP2C (protein phosphatase 2C) gene (At3g05640).

Also, as revealed in FIG. 9, in the case of the transformed plants produced by introducing the FBA1 gene (At2g01140) into the transformed plants that had been produced with the introduction of the fragment containing ORF of the PP2C (protein phosphatase 2C) gene (At3g05640), the total amount of biomass of the above-ground parts had improved by about 8% to 14% compared with the transformed plants produced with the introduction of a fragment containing ORF of the PP2C (protein phosphatase 2C) gene (At3g05640).

All publications, patents, and patent applications cited herein are incorporated herein by reference in their entirety.
[Sequence Listing]

The invention claimed is:

1. A modified plant exhibiting increased production of biomass and/or seeds as compared to a wild-type plant, said modified plant having been produced by a method selected from the group consisting of (i) to (iv):
    (i) introducing, into a plant, a polynucleotide encoding protein (a) and a polynucleotide encoding protein (b);
    (ii) introducing, into a plant, a polynucleotide encoding protein (a); and activating, in said plant, an expression control region of an endogenous gene encoding protein (b), by genetically modifying the expression control region;
    (iii) activating, in a plant, an expression control region of an endogenous gene encoding protein (a), by genetically modifying the expression control region; and activating, in said plant, an expression control region of an endogenous gene encoding protein (b), by genetically modifying the expression control regions; and
    (iv) activating, in a plant, an expression control region of an endogenous gene encoding protein (a), by genetically modifying the expression control region; and introducing, into said plant, (a) polynucleotide encoding protein (b),
    wherein protein (a) is selected from the group consisting of (1) and (2):
        (1) a protein comprising the amino acid sequence of SEQ ID NO: 5; and
        (2) a protein comprising the amino acid sequence of SEQ ID NO: 5 but in which 1-5 amino acids have been deleted, substituted, and/or added in the sequence of SEQ ID NO: 5,
    and wherein protein (b) is selected from the group consisting of (3) and (4):
        (3) a protein comprising the amino acid sequence of SEQ ID NO: 32; and
        (4) a protein comprising the amino acid sequence of SEQ ID NO: 32 but in which 1-5 amino acids have been deleted, substituted, and/or added in the sequence of SEQ ID NO: 32,
    wherein said plant exhibits increased expression of proteins (a) and (b), and increased production of biomass and/or seeds, as compared to a wild-type plant,
    and wherein said plant exhibits increased production of biomass and/or seeds as compared to a plant which exhibits increased expression of only one of proteins (a) and (b).

2. A method for increasing the production of biomass and/or seeds in a plant, as compared to a wild-type plant, wherein said method comprises a step selected from the group consisting of (i) to (iv):
    (i) introducing, into a plant, a polynucleotide encoding protein (a) and a polynucleotide encoding protein (b);
    (ii) introducing, into a plant, a polynucleotide encoding protein (a); and activating, in said plant, an expression control region of an endogenous gene encoding protein (b), by genetically modifying the expression control region;
    (iii) activating, in a plant, an expression control region of an endogenous gene encoding protein (a), by genetically modifying the expression control region; and activating, in said plant, an expression control region of an endogenous gene encoding protein (b), by genetically modifying the expression control region; and
    (iv) activating, in a plant, an expression control region of an endogenous gene encoding protein (a), by genetically modifying the expression control region; and introducing, into said plant, a. polynucleotide encoding protein (b), wherein protein (a) is selected from the group consisting of (1) and (2):
  (1) a protein comprising the amino acid sequence of SEQ ID NO: 5; and
  (2) a protein comprising the amino acid sequence of SEQ ID NO: 5 but in which 1-5 amino acids have been deleted, substituted, and/or added in the sequence of SEQ ID NO: 5, and wherein protein (b) is selected from the group consisting of (3) and (4):
  (3) a protein comprising the amino acid sequence of SEQ ID NO: 32; and
  (4) a protein comprising the amino acid sequence of SEQ ID NO: 32 but in which 1-5 amino acids have been deleted, substituted, and/or added in the sequence of SEQ ID NO: 32,
  wherein said plant exhibits increased expression of proteins (a) and (b), and increased production of biomass and or seeds, as compared to a wild-type plant,
  and wherein said plant exhibits increased production of biomass and/or seeds as compared to a plant which exhibits increased expression of only one of proteins (a) and (b).

3. A method for producing a plant, comprising the steps of:
  (A) preparing a transformed plant by 1 step selected from the group consisting of (i) to (iv):
    (i) introducing, into a plant, a polynucleotide encoding protein (a) and a polynucleotide encoding protein (b);
    (ii) introducing, into a plant a polynucleotide encoding protein (a); and activating, in said plant an expression control region of an endogenous gene encoding protein {b), by genetically modifying the expression control region;
    (iii) activating, in a plant, an expression control region of an endogenous gene encoding protein (a), by genetically modifying the expression control region; and
    activating, in said plant, an expression control region of an endogenous gene encoding protein (b), by genetically modifying the expression control region; and
    (iv) activating, in a plant an expression control region of an endogenous gene encoding protein (a), by genetically modifying the expression control region; and introducing, into said plant. a polynucleotide encoding protein (b),
  wherein protein (a) is selected from the group consisting of (1) and (2):
    (1) a protein comprising the amino acid sequence of SEQ ID NO: 5; and
    (2) a protein comprising the amino acid sequence of SEQ ID NO:5 but in which 1-5 amino acids have been deleted, substituted, and/or added in the sequence of SEQ ID NO: 5,
  and wherein protein (b) is selected from the group consisting of (3) and (4):
    (3) a protein comprising the amino acid sequence of SEQ ID NO: 32; and
    (4) a protein comprising the amino acid sequence of SEQ ID NO: 32 but in which 1-5 amino acids have been deleted, substituted, and/or added in the sequence of SEQ ID NO: 32,
  (B) measuring the amount of biomass and/or seeds of a progeny plant of the transformed plant, and
  (C) selecting a line in which the amount of biomass and/or seeds is increased as compared to a wild-type plant; and in which the amount of biomass and/or seeds is increased as compared to a plant which exhibits increased expression of only one of proteins (a) and (b).

4. The plant according to claim 1,
wherein protein (a) is a protein comprising the amino acid sequence of SEQ ID NO: 5,
and wherein protein (b) is a protein comprising the amino acid sequence of SEQ ID NO: 32.

5. The method according to claim 2,
wherein protein (a) is a protein comprising the amino acid sequence of SEQ ID NO: 5,
and wherein protein (b) is a protein comprising the amino acid sequence of SEQ ID NO: 32.

6. The method according to claim 3,
wherein protein (a) is a protein comprising the amino acid sequence of SEQ ID NO: 5, and wherein protein (b) is a protein comprising the amino acid sequence of SEQ ID NO: 32.

* * * * *